US012509446B2

(12) United States Patent
Rovati et al.

(10) Patent No.: US 12,509,446 B2
(45) Date of Patent: Dec. 30, 2025

(54) FYN AND VEGFR2 KINASE INHIBITORS

(71) Applicant: ROTTAPHARM BIOTECH S.R.L., Monza (IT)

(72) Inventors: Lucio Claudio Rovati, Monza (IT); Gianfranco Caselli, Milan (IT); Roberto Artusi, Rho (IT); Laura Mennuni, Carnate (IT); Fabrizio Colace, Monza (IT); Stefano Mandelli, Casatenovo (IT); Clara Bovino, Gessate (IT); Filippo Magaraci, Monza (IT); Benedetta Buzzi, Meda (IT)

(73) Assignee: Rottapharm Biotech S.R.L., Monza (IT)

( * ) Notice: Subject to any disclaimer, the term of this patent is extended or adjusted under 35 U.S.C. 154(b) by 762 days.

(21) Appl. No.: 17/783,338

(22) PCT Filed: Dec. 7, 2020

(86) PCT No.: PCT/EP2020/084847
§ 371 (c)(1),
(2) Date: Jun. 8, 2022

(87) PCT Pub. No.: WO2021/116005
PCT Pub. Date: Jun. 17, 2021

(65) Prior Publication Data
US 2023/0061118 A1 Mar. 2, 2023

(30) Foreign Application Priority Data
Dec. 9, 2019 (WO) ................. PCT/EP2019/084287

(51) Int. Cl.

| | |
|---|---|
| *C07D 403/12* | (2006.01) |
| *A61P 19/02* | (2006.01) |
| *A61P 29/00* | (2006.01) |
| *C07D 231/40* | (2006.01) |
| *C07D 295/155* | (2006.01) |
| *C07D 401/12* | (2006.01) |
| *C07D 401/14* | (2006.01) |
| *C07D 403/14* | (2006.01) |
| *C07D 413/14* | (2006.01) |
| *C07D 417/12* | (2006.01) |
| *C07D 417/14* | (2006.01) |
| *C07D 471/04* | (2006.01) |

(52) U.S. Cl.
CPC ............ *C07D 403/12* (2013.01); *A61P 19/02* (2018.01); *A61P 29/00* (2018.01); *C07D 231/40* (2013.01); *C07D 295/155* (2013.01); *C07D 401/12* (2013.01); *C07D 401/14* (2013.01); *C07D 403/14* (2013.01); *C07D 413/14* (2013.01); *C07D 417/12* (2013.01); *C07D 417/14* (2013.01); *C07D 471/04* (2013.01)

(58) Field of Classification Search
CPC .............. C07D 403/12; C07D 295/155; C07D 231/40; C07D 401/14; C07D 403/14; C07D 413/14; C07D 417/12; C07D 417/14; C07D 471/04; A61P 19/02; A61P 29/00; A61P 35/00
See application file for complete search history.

(56) References Cited

U.S. PATENT DOCUMENTS

2006/0161645 A1* 7/2006 Moriwaki .............. G06Q 10/06
707/E17.005

FOREIGN PATENT DOCUMENTS

| | | | |
|---|---|---|---|
| EP | 3070084 | A1 | 9/2016 |
| WO | 0027822 | A2 | 5/2000 |
| WO | 2008157131 | A1 | 12/2008 |
| WO | 2009076140 | A1 | 6/2009 |

* cited by examiner

*Primary Examiner* — Joseph K Mckane
*Assistant Examiner* — Anna Grace Kuckla
(74) *Attorney, Agent, or Firm* — Elmore Patent Law Group, P.C.; Joseph C. Zucchero; Carolyn S. Elmore

(57) ABSTRACT

The invention relates to a N-phenylcarbamoyl compound of Formula (I) or a pharmaceutically acceptable salt thereof for use in the inhibition of at least one of tyrosine kinase selected from Fyn and VEGFR2 in the treatment of diseases and disorders involved with one or both kinases.

(I)

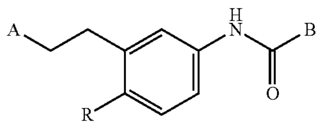

32 Claims, 1 Drawing Sheet

FYN AND VEGFR2 KINASE INHIBITORS

FIELD OF THE INVENTION

The present invention N-phenylcarbamoyl compound of Formula (I) as FYN and VEGFR2 kinase inhibitors.

BACKGROUND OF THE INVENTION

Protein kinases are promising drug targets for the treatment of several disorders ranging from cancer, autoimmune pathologies, inflammation, or neurodegenerative diseases. Fyn is an intracellular tyrosine kinase belonging to Src Family Kinases (SFKs), which is involved in several biological processes (e.g. growth factor and cytokine receptor signalling, T cell and B-cell receptor signalling, ion channel function, platelet activation, and differentiation of natural killer cells).

Many literature data demonstrated that Fyn has a major role in mediating pain. The phosphorylation of NMDA receptors, that is essential for maintenance of neuropathic pain, is mainly dependent on Fyn activation. This role for Fyn has been further deepened, indicating that Fyn dependent phosphorylation of NMDA and AMPA is heavily implicated also in an inflammatory pain experimental model and is critical for the development of tactile allodynia in the state of prediabetic neuropathy in mice.

In a recent study, it is demonstrated that among SFKs family, only Fyn is the most strongly up-regulated protein in the degenerated and damaged articular cartilage of ageing mice. Moreover, Fyn levels resulted elevated either in cartilage of mice with experimental OA and in human OA cartilage, from subjects undergoing total knee replacement. (Li, K. et al. Tyrosine kinase Fyn promotes osteoarthritis by activating the β-catenin pathway. Ann. Rheum. Dis. annrheumdis-2017-212658, 2018).

During later stages of OA in affected patients, the expression of a potent angiogenic factor, the Vascular Endothelial Growth Factor (VEGF) has been found to be increased in the articular cartilage, synovium, synovial fluid, subchondral bone and serum. Assessment of VEGF as a biomarker in patients with OA demonstrates that increased synovial fluid VEGF is not only correlated with grade of OA severity but also with the degree of OA pain. VEGF signalling is mediated by the three kinase insert domain receptors (receptor tyrosine kinase or RTKs) VEGFR-1, -2 and -3, and VEGFA/VEGFR2 is the most prominent ligand-receptor complex in the VEGF system having a key role in angiogenesis. In endothelial cells, VEGF/VEGFR2 binding provokes Fyn activation that triggers a series of downstream signaling pathways and the results are actin polymerization, stress fibers formation and endothelial cell migration, essential to promote the growth of new vessels. (Lamalice et al, Phosphorylation of Tyr1214 within VEGFR-2 Triggers the Recruitment of Nck and Activation of Fyn Leading to SAPK2/p38 Activation and Endothelial Cell Migration in Response to VEGF, 281, 34009-34020, 2006).

Furthermore, a wide number of studies have discovered that VEGF signalling at chondrocytes influences pro-catabolic mediators (i.e matrix metalloproteinases, aggrecanases) and the dual effects of VEGF and inflammatory cytokines on chondrocytes may potentiate cartilage degeneration. Inflammatory pathways are tied to OA progression, angiogenesis stimulates inflammation and inflammation promotes angiogenesis. (Hamilton, J. L. et al. Targeting VEGF and Its Receptors for the Treatment of Osteoarthritis and Associated Pain. J. Bone Miner. Res. 31, 911-924 (2016)). Furthermore, inflammation is a classical mediator of sensitization of fine un-myelinated sensory nerves, which mediates OA pain.

Angiogenesis is an important component of both inflammation and pathogenesis in inflammatory bowel diseases (IBD), which has two major types, ulcerative colitis (UC) and Crohn's disease (CD). Chronic inflammation and angiogenesis are closely related processes, in fact immune/inflammatory cells secrete multiple angiogenic factors (i.e. growth factors, cytokines).

The level of VEGF was found to be increased in serum of IBD patients and the source are inflamed intestinal tissue and peripheral blood mononuclear cells. In IBD, physiological angiogenesis turns to pathological angiogenesis at early stages of the disease and the factor or factors causing conversion of physiological angiogenesis to pathological angiogenesis are still unknown (Angiogenesis in Inflammatory Bowel Disease—C. Alkim et al.—International Journal of Inflammation, Volume 2015, Article ID 970890)

SUMMARY OF THE INVENTION

The inventors surprisingly found a novel class of chemical compounds exhibiting a yet undescribed dual profile in selectively and potently inhibiting both the VEGF receptor VEGFR-2 (frequently referred to as the KDR receptor) and Fyn, a member of Src family.

The invention hence concerns a N-phenylcarbamoyl compound of Formula (1) or salt thereof (I)

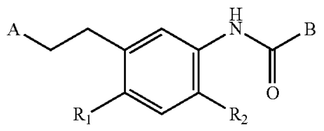

wherein

A is

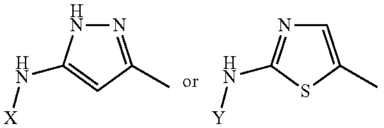

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring;

Y is an optionally substituted 5- or 6-membered heteroaryl ring;

B is an optionally substituted group selected from the group consisting of a phenyl, a 5- or 6-membered heteroaryl ring, 5- or 6-membered saturated heterocyclic ring, azaspiro($C_7$-$C_{10}$)alkyl and saturated ($C_3$-$C_6$) cycloalkyl-NH—;

$R_1$ and $R_2$ are optionally and not simultaneously present and independently selected from ($C_1$-$C_3$)alkyl and halogen.

This unprecedented profile candidates this series as very promising compounds in treating diseases, such as osteoarthritis and others, in which the two kinases acting in synergy has a detrimental role. The series is endowed of a peculiar and surprising pharmacokinetic profile that favours topical treatment with high doses without parallel increased concentrations in blood or unaffected tissues, thus assuring an unprecedented safety profile.

Therefore the invention concerns also a N-phenylcarbamoyl compound of Formula (I)

(I)

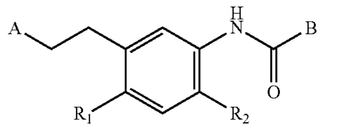

or a pharmaceutically acceptable salt thereof wherein

A is

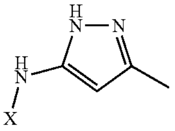 or 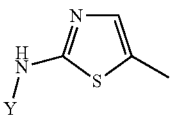

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring;

Y is an optionally substituted ($C_5$-$C_6$)heteroaryl ring;

B is an optionally substituted group selected from the group consisting of a phenyl, a 5- or 6-membered heteroaryl ring, 5- or 6-membered saturated heterocyclic ring, azaspiro($C_7$-$C_{10}$)alkyl and saturated ($C_3$-$C_6$) cycloalkyl-NH—;

$R_1$ and $R_2$ are optionally and not simultaneously present and independently ($C_1$-$C_3$)alkyl or halogen for use as a medicament.

In another aspect the invention relates also a N-phenylcarbamoyl compound of Formula (I)

(I)

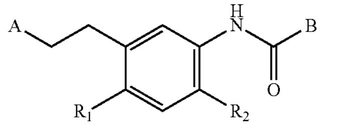

or a pharmaceutically acceptable salt thereof for use in the inhibition of at least one of tyrosine kinase selected from Fyn and VEGFR2 in the treatment of diseases and disorders involved with one or both kinases, wherein A is

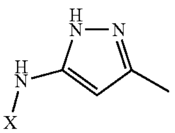 or 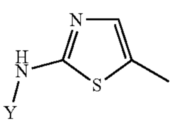

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring;

Y is an optionally substituted ($C_5$-$C_6$)heteroaryl ring;

B is an optionally substituted group selected from the group consisting of a phenyl, a 5- or 6-membered heteroaryl ring, 5- or 6-membered saturated heterocyclic ring, azaspiro($C_7$-$C_{10}$)alkyl and saturated ($C_3$-$C_6$) cycloalkyl-NH—;

$R_1$ and $R_2$ are optionally and not simultaneously present and independently ($C_1$-$C_3$)alkyl or halogen.

Therefore the compound of Formula (I) acts also as a tyrosine kinase inhibitor of two kinases, Fyn and VEGFR being hence a dual kinases inhibitor. This multi-target treatment has therapeutic potential for the treatment of osteoarthritis and other pathologies and diseases involved with both kinases.

Specifically the compound of the invention is disclosed for use in the treatment of a disorder/disease/pathology selected from the group consisting osteoarthritis; eye diseases such as intraocular neovascular disorders, such as age-related macular degeneration, diabetic macular oedema and other ischaemia-related retinopathies, or immune-mediated corneal graft rejection; skin disorders such as psoriasis or rosacea; acute or chronic pain; lung diseases such as acute respiratory distress syndrome (ARDS), Idiopathic Pulmonary Fibrosis (IPF), Hypersensitivity Pneumonitis (HP) and Systemic Sclerosis (SSc); cancer such as metastatic colorectal cancer, non-squamous non-small cell lung cancer, metastatic renal cell carcinoma, recurrent glioblastoma multiforme, gynaecological malignancies, metastatic breast cancer.

In a preferred aspect the compound of the invention is disclosed for use in the treatment of acute and chronic pain selected from neuropathic pain, inflammatory pain, osteoarthritis pain, ocular pathology pain.

DETAILED DESCRIPTION OF THE INVENTION

Figure 1:
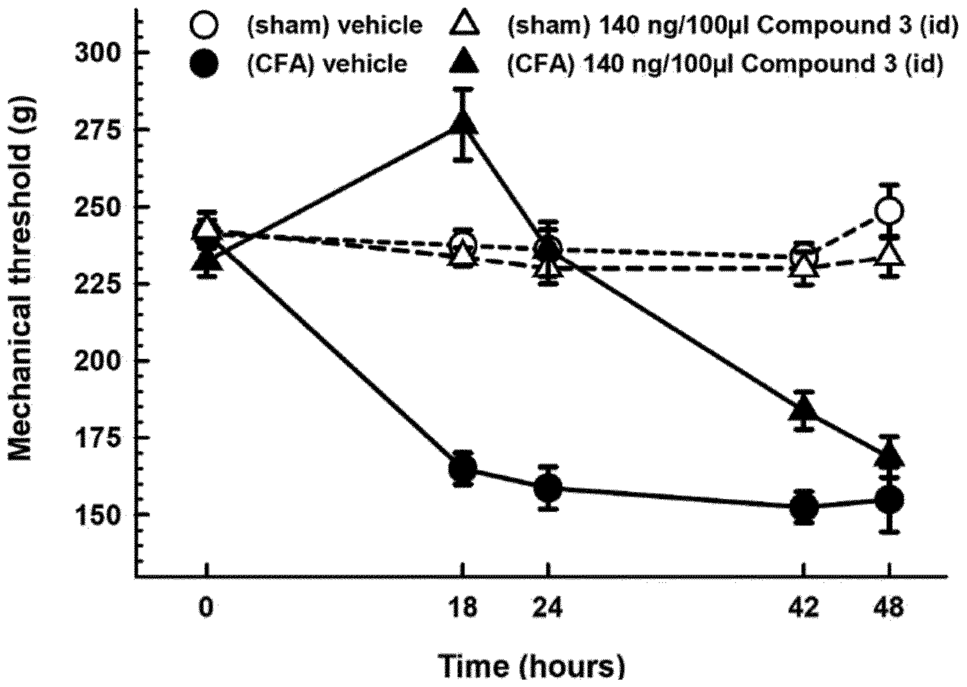
FIG. 1: Local analgesic efficacy of compound 3 in the rat CFA assay. The activity is reported as the mechanical threshold (weight borne by the CFA inflamed paw). The data for naïve animals treated with vehicle of with the test substance are also shown, to demonstrate the lack of effect on normal pain threshold.

The invention relates to a pharmaceutical composition containing a dual VEGF2/Fyn inhibitor able to act locally in resolving diseases otherwise resistant to other drugs, without producing a general systemic toxicity.

The invention hence concerns a N-phenylcarbamoyl compound of Formula (I)

(I)

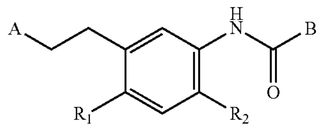

or a salt thereof wherein

A is

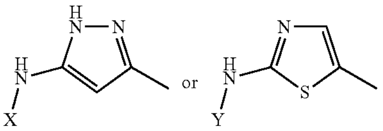

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring;

Y is an optionally substituted ($C_5$-$C_6$)heteroaryl ring;

B is an optionally substituted group selected from the group consisting of a phenyl, a 5- or 6-membered heteroaryl ring, 5- or 6-membered saturated heterocyclic ring, azaspiro($C_7$-$C_{10}$)alkyl and saturated ($C_3$-$C_6$) cycloalkyl-NH—;

$R_1$ and $R_2$ are optionally and not simultaneously present and independently ($C_1$-$C_3$)alkyl or halogen.

In the present invention, when the following terms are used:

"compound(s) of the invention" or "compound(s) of this invention" mean a compound of Formula (I), as defined above, in any form, i.e., any salt or non-salt form (e.g., as a free acid or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi- hydrates)), and mixtures of various forms;

"optionally substituted" means unsubstituted groups or rings or groups or rings substituted with one or more specified substituents;

"saturated 5- or 6-membered heterocyclic ring" means a saturated carbocyclic ring wherein one or two atoms of carbon are replaced by heteroatoms such as nitrogen, oxygen or sulphur; non-limiting examples are tetrahydropyrane, pyrrolidine, imidazolidine, pyrazolidine, thiazolidine, tetrahydrofuran, 1,3-dioxolane, piperidine, piperazine and morpholine;

"($C_1$-$C_3$)alkyl" means a linear or branched saturated hydrocarbon group containing from 1 to 3 carbon atoms;

"($C_1$-$C_4$)alkyl" means a linear or branched saturated hydrocarbon group containing from 1 to 4 carbon atoms;

"saturated ($C_3$-$C_6$)cycloalkyl" means saturated 3- to 6-membered all-carbon monocyclic rings; non-limiting examples are cyclopropane, cyclobutane, cyclopentane, cyclohexane;

"azaspiro($C_7$-$C_{10}$)alkyl" means saturated 8-10-membered ring of carbon atoms and one N atom, forming a cyclic ring with spiro atom;

"halogen" means an atom of chloro, fluoro, bromo and iodo;

"5- or 6-membered heteroaryl ring" means an unsaturated carbocyclic ring wherein one to three carbon atoms are replaced by heteroatoms such as nitrogen, oxygen or sulphur; non-limiting examples are pyridyl, pyrazinyl, pyrimidinyl, pyridazinyl, indolyl, imidazolyl, thiazolyl, pyrrolyl, furyl, oxazolyl, isoxazolyl, pyrazolyl, thienyl, thiadiazolyl, isoxazolyl, isothiazolyl, oxadiazolyl, indazolyl.

According to the invention A is

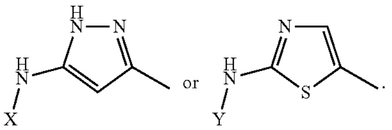

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring.

X can be an optionally substituted 5- or 6-membered heteroaryl ring. The 5- or 6-membered heteroaryl ring is preferably pyrazine or pyridine or pyrimidine, optionally substituted with one or more substituent selected from the group consisting of ($C_1$-$C_3$)alkyl, (morpholino)methyl, (dimethylmorpholino)methyl, pyrrolidine-1-ylmethyl, 4-ethylpiperazin-1-yl, 4-(2-hydroxyethyl)piperazin-1-yl, 3-hydroxyazetidin-1-yl, 3-(dimethylamino)pyrrolidin-1-yl, (2-hydroxyethyl)-1H-pyrazol-4-yl, morpholine-1-yl and cyano. More preferably the substituent ($C_1$-$C_3$)alkyl is methyl.

X can be an optionally substituted 2,3-dihydro-1H-pyrrolo[3,4-c]pyridinyl. When it is substituted it is preferably substituted with a with one or more substituent selected from the group consisting of ($C_1$-$C_3$)alkyl, hydroxy($C_1$-$C_3$)alkyl and (($C_1$-$C_3$)alkyl)CO—, more preferably ethyl, 2-hydroxyethyl and acetyl.

X can an optionally substituted (5- or 6-membered heteroaryl)CO—. Preferably (5- or 6-membered heteroaryl) CO— is (pyridine)CO— or (pyrimidine)CO—. When it is substituted it is preferably substituted with a with one or more ($C_1$-$C_3$)alkyl.

X can an optionally substituted (phenyl)CO—. When it is substituted it is preferably substituted with one or more substituent selected from the group consisting of halogen, (1-isopropylazetidin-3-yl)oxy, 4-methylpiperazin-1-yl, and 1-methylpiperidin-4-yl. When it is halogen, it is more preferably fluoro.

Y is an optionally substituted ($C_5$-$C_6$)heteroaryl ring. The optionally substituted ($C_5$-$C_6$)heteroaryl ring is preferably an optionally substituted pyrazine, more preferably unsubstituted. When pyrazine is substituted, it is preferably substituted with one or more ($C_1$-$C_3$)alkyl, still more preferably methyl.

$R_1$ and $R_2$ are optionally and not simultaneously present and independently ($C_1$-$C_3$)alkyl or halogen. Preferably $R_1$ is ($C_1$-$C_3$)alkyl, more preferably methyl. Preferably $R_2$ is H or halogen. When $R_1$ is halogen it is preferably fluoro or chloro, more preferably fluoro. When $R_2$ is halogen it is preferably fluoro.

B can be an optionally substituted phenyl. When B is a substituted phenyl it is preferably substituted with one or more substituent selected from the group consisting of ($C_1$-$C_3$)alkyl, R'$SO_2$—, R'R"N($C_1$-$C_3$)alkyl, R'NH($C_1$-$C_3$)alkyl-, R'R"N—, trifluoromethyl, difluoromethyl, halogen, R'R"$NSO_2$—, ($C_3$-$C_6$)cycloalkyl, ($C_3$-$C_6$)cycloalkyl-NH—, NR'($C_3$-$C_6$)cycloalkyl- where R' and R" are, independently each other, ($C_1$-$C_3$)alkyl, more preferably methyl. Among the preferred substituents for phenyl, the following can be cited: $CH_3SO_2$—, —$CH_2N(CH_3)_2$, $CH_3$, $CF_3$, $CHF_2$, fluoro, —$SO_2N(CH_3)_2$, (N-ethyl)aminocyclopropyl.

B can be an optionally substituted 5- or 6-membered heteroaryl ring. The optionally substituted 5- or 6-membered heteroaryl ring is preferably pyridine or oxazole. When ($C_5$-$C_6$)heteroaryl ring is substituted, it is preferably substituted with one or more hydroxy($C_1$-$C_3$)alkyl, $CF_3$, ($C_1$-$C_4$)alkyl, cyano($C_1$-$C_3$)alkyl and ($C_3$-$C_6$)cycloalkyl-$SO_2$—. Among the preferred substituents for ($C_5$-$C_6$)heteroaryl ring, preferably for pyridine and oxazole, the following can be cited: 2-cyanopropan-2-yl, 2-cyanopropan-2-yl, $CH_3$, $CF_3$, fluoro, isobutyl or cyclopropylsulphonyl.

B can be azaspiro($C_7$-$C_{10}$)alkyl. Preferably it is azaspiro[3,4]octane or azaspiro[4,5]decane.

B can be an optionally substituted 5- or 6-membered saturated heterocyclic ring. Preferably it is pyrrolidine, more preferably substituted with one or more ($C_1$-$C_3$)alkyl, still more preferably ethyl.

B can be an optionally substituted saturated ($C_3$-$C_6$)cycloalkyl-NH—. Preferably it is 4,4-(dimethylciclohexyl)-NH—, cyclopentyl-NH—.

In a preferred embodiment A is

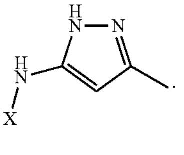

In this preferred embodiment X is preferably an optionally substituted 5- or 6-membered heteroaryl ring, more preferably an optionally substituted pyrazine.

B is preferably an optionally substituted phenyl, preferably substituted with $CF_3$.

In a preferred aspect the compound of Formula (I) is selected from the group consisting of:

1) N-(4-methyl-3-(2-(5-(pyrazin-2-ylamino)-1H-pyrazol-3-yl)ethyl)phenyl)-3-(methyl sulfonyl)benzamide,
2) 2-(2-cyanopropan-2-yl)-N-(4-methyl-3-(2-(5-(pyrazin-2-ylamino)-1H-pyrazol-3-yl) ethyl)phenyl) isonicotinamide,
3) N-(4-methyl-3-(2-(5-(pyrazin-2-ylamino)-1H-pyrazol-3-yl)ethyl)phenyl)-3-(trifluoro methyl)benzamide,
4) 4-(1-(ethylamino)cyclopropyl)-N-(4-methyl-3-(2-(5-(pyrazin-2-ylamino)-1H-pyrazol-3-yl)ethyl)phenyl) benzamide,
5) 2-(2-hydroxypropan-2-yl)-N-(4-methyl-3-(2-(5-(pyrazin-2-ylamino)-1H-pyrazol-3-yl)ethyl)phenyl) isonicotinamide,
6) 2-methyl-N-(4-methyl-3-(2-(5-(pyrazin-2-ylamino)-1H-pyrazol-3-yl)ethyl)phenyl)-5-(trifluoromethyl)oxazole-4-carboxamide,
7) 2-fluoro-N-(4-methyl-3-(2-(5-(pyrazin-2-ylamino)-1H-pyrazol-3-yl)ethyl)phenyl)-5-(trifluoromethyl) benzamide,
8) 4-(cyclopropylsulfonyl)-N-(4-methyl-3-(2-(5-(pyrazin-2-ylamino)-1H-pyrazol-3-yl) ethyl)phenyl)picolinamide,
9) N-(3-(2-fluoro-5-(6-isobutylnicotinamido)phenethyl)-1H-pyrazol-5-yl)pyrimidine-2-carboxamide
10) N-(4-fluoro-3-(2-(5-((2-(2-hydroxyethyl)-2,3-dihydro-1H-pyrrolo[3,4-c]pyridin-6-yl)amino)-1H-pyrazol-3-yl) ethyl)phenyl)-3-(trifluoromethyl)benzamide
11) 2-(2-cyanopropan-2-yl)-N-(4-fluoro-3-(2-(5-(pyrazin-2-ylamino)-1H-pyrazol-3-yl) ethyl)phenyl) isonicotinamide,
12) N-(4-fluoro-3-(2-(5-(pyrazin-2-ylamino)-1H-pyrazol-3-yl)ethyl)phenyl)-3-(methyl sulfonyl)benzamide,
13) N-(4-fluoro-3-(2-(5-(pyrazin-2-ylamino)-1H-pyrazol-3-yl)ethyl)phenyl)-3-(trifluoro methyl)benzamide,
14) N-(3-(2-(5-((3,5-dimethylpyrazin-2-yl)amino)-1H-pyrazol-3-yl)ethyl)-4-fluoro phenyl)-3-(trifluoromethyl) benzamide,
15) N-(4-fluoro-3-(2-(5-((3-methylpyrazin-2-yl)amino)-1H-pyrazol-3-yl)ethyl)phenyl)-3-(trifluoromethyl) benzamide,
16) N-(4-chloro-3-(2-(5-(pyrazin-2-ylamino)-1H-pyrazol-3-yl)ethyl)phenyl)-3-(trifluoro methyl)benzamide,
17) N-(3-(2-(5-((2-ethyl-2,3-dihydro-1H-pyrrolo[3,4-c]pyridin-6-yl)amino)-1H-pyrazol-3-yl)ethyl)-4-methylphenyl)-3-(trifluoromethyl)benzamide,
18) N-(5-(2-methyl-5-(3-(trifluoromethyl)benzamido)phenethyl)-1H-pyrazol-3-yl) picolinamide,
19) N-(3-(2-(3-(4-fluorobenzamido)-1H-pyrazol-5-yl) ethyl)-4-methylphenyl)-3-(trifluoro methyl)benzamide,
20) N-(4-methyl-3-(2-(5-((3-methylpyrazin-2-yl)amino)-1H-pyrazol-3-yl)ethyl)phenyl)-6-azaspiro[3.4]octane-6-carboxamide,
21) 3,3-diethyl-N-(4-methyl-3-(2-(5-((3-methylpyrazin-2-yl)amino)-1H-pyrazol-3-yl) ethyl)phenyl) pyrrolidine-1-carboxamide,
22) 3,3-diethyl-N-(4-methyl-3-(2-(5-(pyrazin-2-ylamino)-1H-pyrazol-3-yl)ethyl)phenyl) pyrrolidine-1-carboxamide,
23) N-(3-(5-(3-(4,4-dimethylcyclohexyl)ureido)-2-methylphenethyl)-1H-pyrazol-5-yl)-4-((1-isopropylazetidin-3-yl)oxy)benzamide,
24) N-(3-(5-(3-cyclopentylureido)-2-methylphenethyl)-1H-pyrazol-5-yl)-4-(4-methyl piperazin-1-yl)benzamide, 25) N-(3-(5-(3-(4,4-dimethylcyclohexyl)ureido)-2-methylphenethyl)-1H-pyrazol-5-yl)-4-(l-methylpiperidin-4-yl) benzamide,
26) N-(4-fluoro-3-(2-(3-((2-methyl-6-(morpholinomethyl) pyrimidin-4-yl)amino)-1H-pyrazol-5-yl)ethyl)phenyl)-3-(trifluoromethyl)benzamide,
27) N-(3-(2-(3-((6-(((2S,6R)-2,6-dimethylmorpholino) methyl)-2-methylpyrimidin-4-yl) amino)-1H-pyrazol-5-yl)ethyl)-4-fluorophenyl)-3-(trifluoromethyl)benzamide,
28) N-(4-fluoro-3-(2-(3-((2-methyl-6-(pyrrolidin-1-ylmethyl)pyrimidin-4-yl)amino)-1H-pyrazol-5-yl)ethyl)phenyl)-3-(trifluoromethyl)benzamide,
29) N-(3-(2-(3-((6-(4-ethylpiperazin-1-yl)-2-methylpyrimidin-4-yl)amino)-1H-pyrazol-5-yl)ethyl)-4-fluorophenyl)-3-(trifluoromethyl)benzamide,
30) N-(4-fluoro-3-(2-(3-((6-(4-(2-hydroxyethyl)piperazin-1-yl)-2-methylpyrimidin-4-yl) amino)-1H-pyrazol-5-yl) ethyl)phenyl)-3-(trifluoromethyl)benzamide,
31) N-(4-fluoro-3-(2-(3-((6-(3-hydroxyazetidin-1-yl)-2-methylpyrimidin-4-yl)amino)-1H-pyrazol-5-yl)ethyl) phenyl)-3-(trifluoromethyl)benzamide,
32) (S)-N-(3-(2-(3-((6-(3-(dimethylamino)pyrrolidin-1-yl)-2-methylpyrimidin-4-yl)amino)-1H-pyrazol-5-yl)ethyl)-4-fluorophenyl)-3-(trifluoromethyl)benzamide,
33) 3-(difluoromethyl)-N-(4-methyl-3-(2-(5-(pyrazin-2-ylamino)-1H-pyrazol-3-yl)ethyl) phenyl)benzamide,
34) N-(3-(2-(5-((2-acetyl-2,3-dihydro-1H-pyrrolo[3,4-c] pyridin-6-yl)amino)-1H-pyrazol-3-yl)ethyl)-4-methylphenyl)-3-(trifluoromethyl)benzamide,
35) 3-(isopropylsulfonyl)-N-(4-methyl-3-(2-(5-((3-methylpyridin-2-yl)amino)-1H-pyrazo 1-3-yl)ethyl) phenyl) benzamide,
36) 2-(2-cyanopropan-2-yl)-N-(4-methyl-3-(2-(5-((3-methylpyridin-2-yl)amino)-1H-pyrazol-3-yl)ethyl)phenyl) isonicotinamide,
37) N-(3-(2-(5-((6-cyano-2-methylpyrimidin-4-yl)amino)-1H-pyrazol-3-yl)ethyl)-4-methylphenyl)-3-(N,N-dimethylsulfamoyl)benzamide,
38) N-(3-(2-(5-((6-cyano-2-methylpyrimidin-4-yl)amino)-1H-pyrazol-3-yl)ethyl)-4-methylphenyl)-8-azaspiro [4.5] decane-8-carboxamide,
39) N-(3-(2-(5-((6-cyano-2-methylpyrimidin-4-yl)amino)-1H-pyrazol-3-yl)ethyl)-4-fluoro phenyl)-4-((dimethylamino) methyl)-3-(trifluoromethyl)benzamide,
40) N-(4-fluoro-3-(2-(5-((2-methylpyrimidin-5-yl)amino)-1H-pyrazol-3-yl)ethyl)phenyl)-3-(trifluoromethyl) benzamide,
41) 4-(2-cyanopropan-2-yl)-N-(4-methyl-3-(2-(5-(pyrazin-2-ylamino)-1H-pyrazol-3-yl) ethyl)phenyl)picolinamide,
42) N-(4-fluoro-3-(2-(3-((6-(1-(2-hydroxyethyl)-1H-pyrazol-4-yl)-2-methylpyrimidin-4-yl)amino)-1H-pyrazol-5-yl)ethyl)phenyl)-3-(trifluoromethyl)benzamide,
43) N-(2-fluoro-5-(2-(5-((2-methyl-6-morpholinopyrimidin-4-yl)amino)-1H-pyrazol-3-yl) ethyl)phenyl)-3-(trifluoromethyl)benzamide,
44) N-(2-fluoro-5-(2-(3-((6-(4-(2-hydroxyethyl)piperazin-1-yl)-2-methylpyrimidin-4-yl) amino)-1H-pyrazol-5-yl) ethyl)phenyl)-3-(trifluoromethyl)benzamide,
45) N-(5-(2-(3-((6-(4-ethylpiperazin-1-yl)-2-methylpyrimidin-4-yl)amino)-1H-pyrazol-5-yl)ethyl)-2-fluorophenyl)-3-(trifluoromethyl)benzamide,
46) N-(2-fluoro-5-(2-(3-((6-(3-hydroxyazetidin-1-yl)-2-methylpyrimidin-4-yl)amino)-1H-pyrazol-5-yl)ethyl) phenyl)-3-(trifluoromethyl)benzamide,
47) 4-((dimethylamino)methyl)-N-(3-(2-(5-(4-morpholinobenzamido)-1H-pyrazol-3-yl) ethyl) phenyl)benzamide,
48) N-(4-methyl-3-(2-(2-(pyrazin-2-ylamino)thiazol-5-yl) ethyl)phenyl)-3-(methyl sulfonyl)benzamide,
49) N-(4-methyl-3-(2-(2-(pyrazin-2-ylamino)thiazol-5-yl) ethyl)phenyl)-3-(trifluoro methyl)benzamide, and
50) 2-(2-cyanopropan-2-yl)-N-(4-methyl-3-(2-(2-(pyrazin-2-ylamino)thiazol-5-yl)ethyl) phenyl)isonicotinamide.

More preferably, the compound of Formula (I) is selected from the group consisting of:
3) N-(4-methyl-3-(2-(5-(pyrazin-2-ylamino)-1H-pyrazol-3-yl)ethyl)phenyl)-3-(trifluoro methyl)benzamide,
6) 2-methyl-N-(4-methyl-3-(2-(5-(pyrazin-2-ylamino)-1H-pyrazol-3-yl)ethyl)phenyl)-5-(trifluoromethyl)oxazole-4-carboxamide,
8) 4-(cyclopropylsulfonyl)-N-(4-methyl-3-(2-(5-(pyrazin-2-ylamino)-1H-pyrazol-3-yl) ethyl)phenyl)picolinamide,
13) N-(4-fluoro-3-(2-(5-(pyrazin-2-ylamino)-1H-pyrazol-3-yl)ethyl)phenyl)-3-(trifluoro methyl)benzamide,
15) N-(4-fluoro-3-(2-(5-((3-methylpyrazin-2-yl)amino)-1H-pyrazol-3-yl)ethyl)phenyl)-3-(trifluoromethyl) benzamide,
34) N-(3-(2-(5-((2-acetyl-2,3-dihydro-1H-pyrrolo[3,4-c] pyridin-6-yl)amino)-1H-pyrazol-3-yl)ethyl)-4-methylphenyl)-3-(trifluoromethyl)benzamide,
49) N-(4-methyl-3-(2-(2-(pyrazin-2-ylamino)thiazol-5-yl) ethyl)phenyl)-3-(trifluoro methyl)benzamide, and Still more preferably the compound of the invention is 3) N-(4-methyl-3-(2-(5-(pyrazin-2-ylamino)-1H-pyrazol-3-yl) ethyl)phenyl)-3-(trifluoromethyl)benzamide.

The compound of the invention can be a salt, preferably a pharmaceutically acceptable salt. Therefore, any acid addition salt or a salt with a base is included in the present invention, as long as they are pharmaceutically acceptable salts.

As examples salts derived from inorganic bases can be cited, including aluminum, ammonium, calcium, copper, ferric, ferrous, lithium, magnesium, manganese salts, manganous, potassium, sodium, zinc, and the like. Preferred are the ammonium, calcium, magnesium, lithium, potassium, and sodium salts. Salts derived from pharmaceutically acceptable organic non-toxic bases can also di included such as salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

Pharmaceutically acceptable salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

A general scheme for preparing the compounds of the invention is outlined below:

b) conversion of compounds III into compounds IV by adding an halo-heterocycle X-$R_2$ in the presence of organometallic catalyst, such as for example tris(dibenzylidene acetone) dipalladium(0), or amide coupling using standard coupling agents such as N-ethyl-N'-(3-dimethylaminopropyl)carbodiimide hydrochloride and dimethylamino pyridine in dichloromethane as solvent;

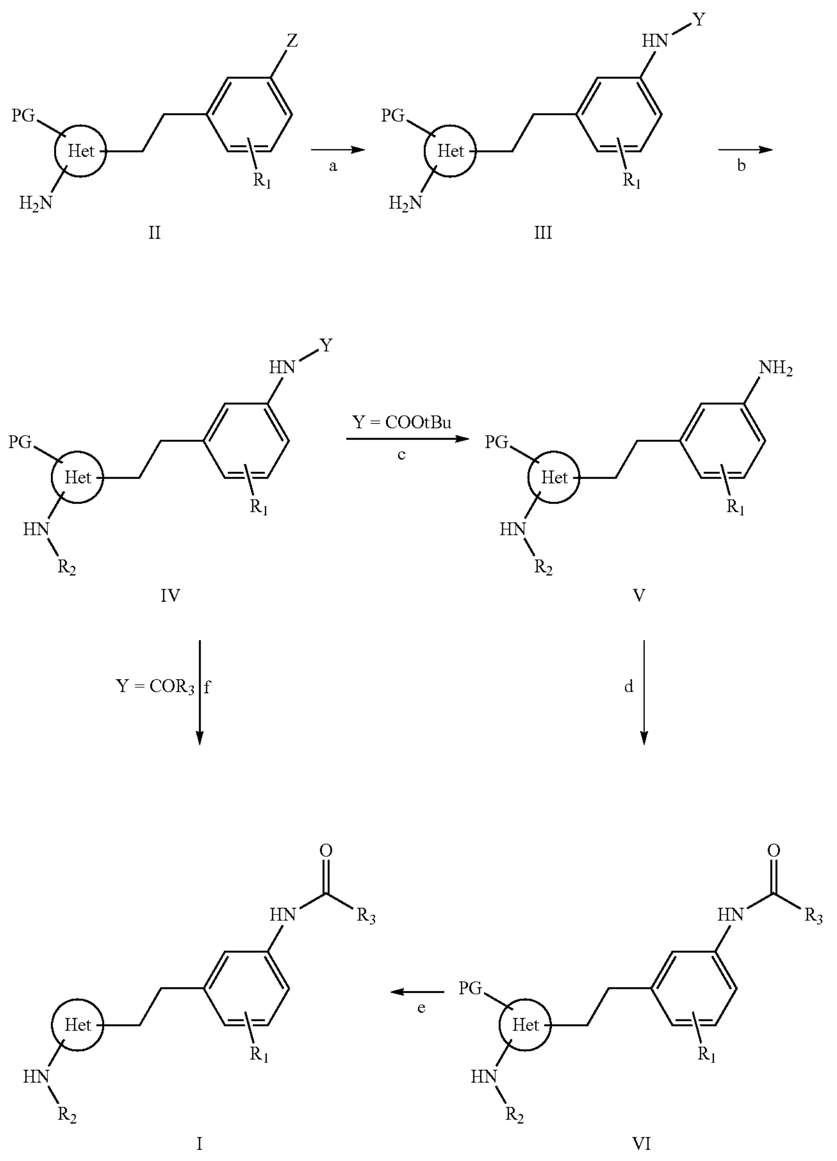

The process as outlined in scheme 1 includes the following steps:

a) conversion of compounds II (Z=Br) into compounds III (Y=H) by adding ammonia in the presence of copper iodide; or compounds II (Z=Br) into compounds III (Y=$COR_3$) by adding benzamide $NH_2COR_3$ in the presence of organometallic catalyst, such as for example tris(dibenzylidene acetone) dipalladium(0); or compounds II (Z=$NH_2$) into compounds III (Y=COOtBu) by adding di-tert-butyl dicarbonate in dichloromethane as solvent;

c) when Y=COOtBu, removal of the tert-butyl oxy carbonyl protecting group using HCl or trifluoro acetic acid in dichloromethane as solvent;

d) amide coupling using standard coupling agents or urea formation using reagents as carbonyl diimidazole in tetrahydrofuran to obtain compounds VI;

e) removal of the protecting group using formic acid to obtain compounds I; and f) when Y=$COR_3$, removal of the protecting group using formic acid to obtain compounds of Formula (I).

Specifically, general syntheses used for preparing compounds of Formula (I) are described in schemes from 1 to 4.

Steps of scheme 1 are reported below:

Scheme 1

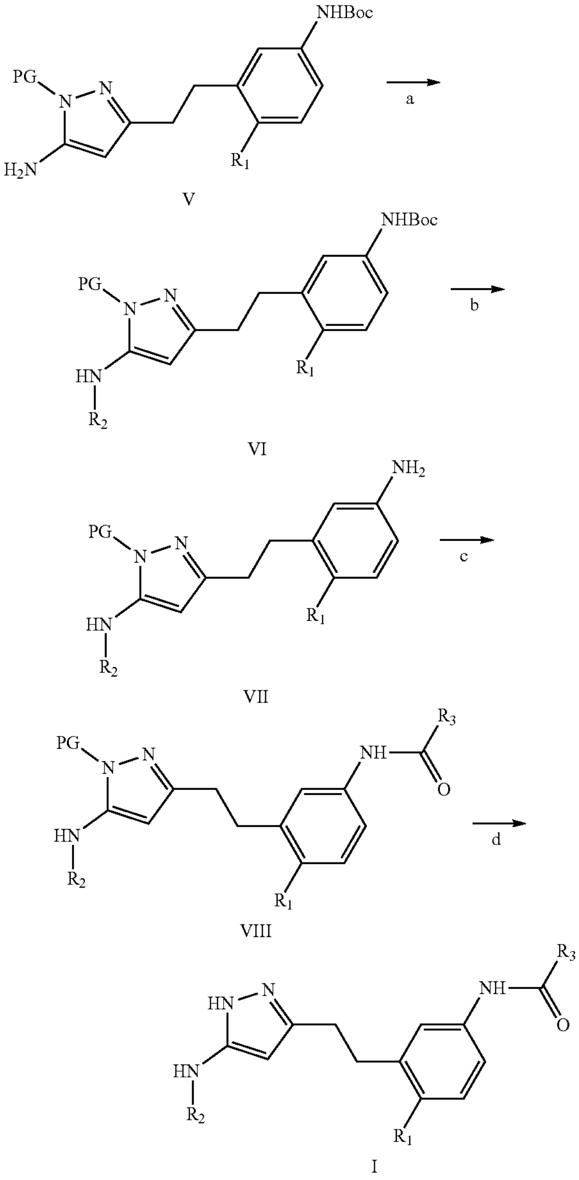

The process as outlined in scheme 1 comprises the following steps:

a1) conversion of compounds V into compounds VI by adding an halo-heterocycle in the presence of organometallic catalyst, such as for example tris(dibenzylidene acetone) dipalladium(0), or amide coupling using standard coupling agents such as N-ethyl-N'-(3-dimethylaminopropyl)carbodiimide hydrochloride and dimethylamino pyridine in dichloromethane as solvent;

b1) removal of the tert-butyl oxy carbonyl protecting group using HCl or trifluoro acetic acid in dichloromethane as solvent;

c1) amide coupling using standard coupling agents or urea formation using reagents as carbonyl diimidazole in tetrahydrofuran to obtain compounds VIII; and d1) removal of the protecting group using formic acid to obtain compounds I Steps of scheme 2 are reported below:

Scheme 2

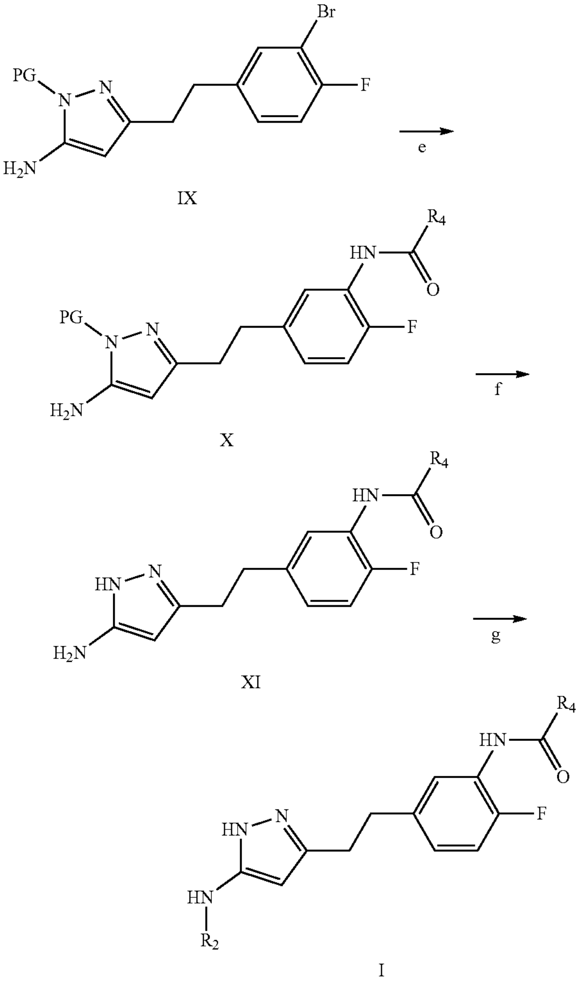

a2) conversion of compounds IX into compounds X by adding a benzamide in the presence of organometallic catalyst, such as for example tris(dibenzylidene acetone) dipalladium(0);

b2) removal of the protecting group using formic acid to obtain compounds XI;

c2) conversion of compounds XI into compounds I by adding an halo-heterocycle in the presence of organometallic catalyst, such as for example tris(dibenzylidene acetone) dipalladium(0).

Another embodiment of the invention to obtain compound of formula (I) is described in scheme 3 below:

Scheme 3

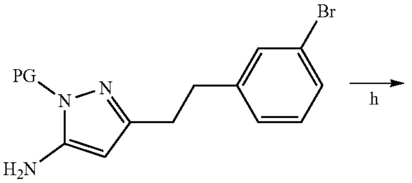

XII

-continued

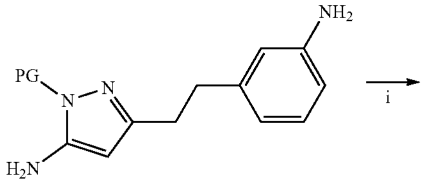

XIII

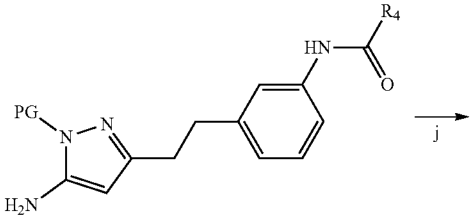

XIV

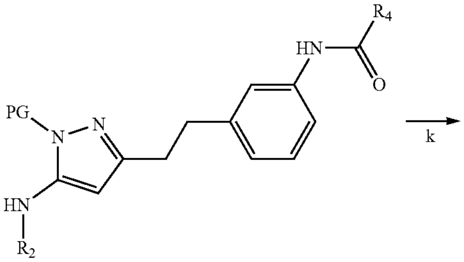

XV

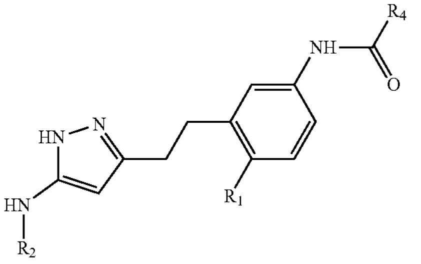

I

The process as outlined in scheme 3 comprises the following steps:

a3) conversion of compounds XII to amines XIII using ammonia in the presence of Copper Iodide as catalyst at 100° C. in a sealed tube;

b3) amide coupling using standard coupling agents to obtain compounds XIV; c3) conversion of compounds XV into compounds XV by adding an halo-heterocycle in the presence of organometallic catalyst, such as for example tris(dibenzylidene acetone) dipalladium(0), or amide coupling using standard coupling agents such as N-ethyl-N'-(3-dimethylaminopropyl)carbodiimide hydrochloride and dimethylamino pyridine in dichloromethane as solvent; and d3) removal of the protecting group using formic acid to obtain compounds I.

Steps of scheme 4 are reported below:

Scheme 4

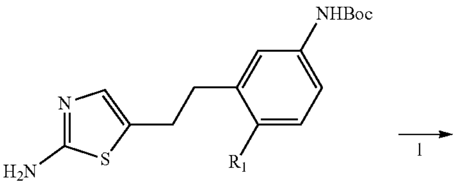

XVI

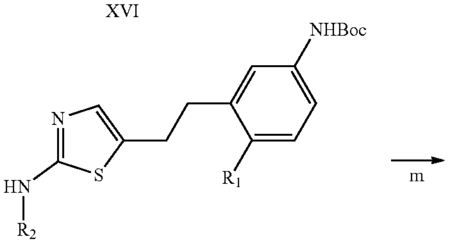

XVII

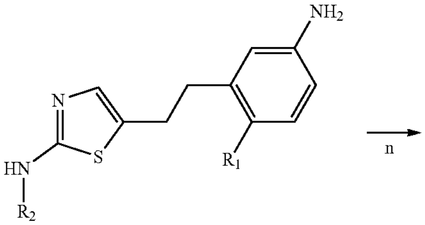

XVIII

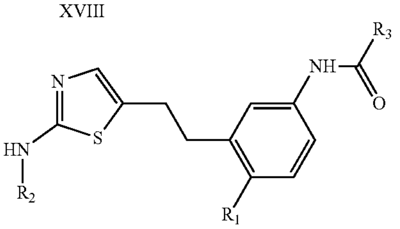

I

The process as outlined in scheme 4 comprises the following steps:

a4) conversion of compounds XVI into compounds XVII by adding an halo-heterocycle in the presence of organometallic catalyst, such as for example tris(dibenzylidene acetone) dipalladium(0), or amide coupling using standard coupling agents such as N-ethyl-N'-(3-dimethylaminopropyl)carbodiimide hydrochloride and dimethylamino pyridine in dichloromethane as solvent;

b4) removal of the BOC protecting group using HCl or trifluoro acetic acid in dichloromethane as solvent;

c4) Amide coupling using standard coupling agents to obtain compounds I.

The compounds of Formula (I) as above described can be used as medicament.

In another aspect the invention relates to a N-phenylcarbamoyl compound of Formula (I)

(I)

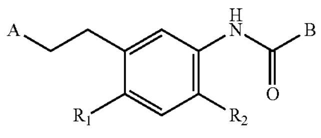

or a pharmaceutically acceptable salt thereof wherein

A is

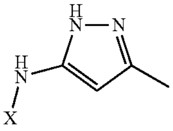

or

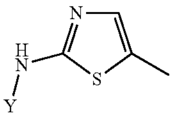

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and saturated $(C_5\text{-}C_6)$heterocyclic ring;

Y is an optionally substituted $(C_5\text{-}C_6)$heteroaryl ring;

B is an optionally substituted group selected from the group consisting of a phenyl, a 5- or 6-membered heteroaryl ring, 5- or 6-membered saturated heterocyclic ring, azaspiro$(C_7\text{-}C_{10})$alkyl and saturated $(C_3\text{-}C_6)$cycloalkyl-NH—;

$R_1$ and $R_2$ are optionally and not simultaneously present and independently selected from $(C_1\text{-}C_3)$alkyl and halogen for use as a medicament.

A current trend in the development of tyrosine kinase inhibitors is the assumption that multi targeted therapy, which targets several signalling pathways simultaneously, is more effective than single targeted therapy. In cancer, the considerations to determine whether multiple single kinase inhibitors or a single multi kinase inhibitor is preferable are based on aspects concerning efficacy, resistance, pharmacokinetics, selectivity and tumour environment. The clinical features of OA are symptoms, mainly pain, and pathological changes in joint structure, both determining the functional impairment then a tyrosine kinase inhibitors multi-target treatment has therapeutic potential for the treatment of OA.

Therefore, in another aspect the invention relates also a N-phenylcarbamoyl compound of Formula (I)

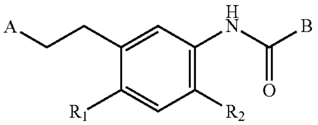

(I)

or a pharmaceutically acceptable salt thereof for use in the inhibition of at least one of tyrosine kinase selected from Fyn and VEGFR2 in the treatment of diseases and disorders involved with one or both kinases, wherein A is

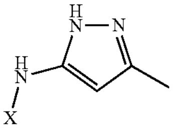

or

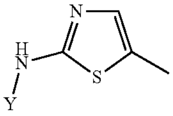

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring;

Y is an optionally substituted $(C_5\text{-}C_6)$heteroaryl ring;

B is an optionally substituted group selected from the group consisting of a phenyl, a 5- or 6-membered heteroaryl ring, 5- or 6-membered saturated heterocyclic ring, azaspiro$(C_7\text{-}C_{10})$alkyl and saturated $(C_3\text{-}C_6)$cycloalkyl-NH—;

$R_1$ and $R_2$ are optionally and not simultaneously present and independently $(C_1\text{-}C_3)$alkyl or halogen.

Specifically, and surprisingly the compounds of Formula (I) are used for treating osteoarthritis. Without being bound to any theory, the inventors deem that a compound targeting two kinases, Fyn and VEGFR2, that seem pivotal for determining both the symptoms and the progression of OA, appears the ideal candidate, allowing to overcome the classical dichotomy between structure and symptom modifying agents. Furthermore, an intra-articular way of action of the compound, providing the maximal concentration at the peripheral site, together with a poor systemic availability, allows to predict a good efficacy without possible systemic safety issues. Reduced systemic drug exposure may be of particular relevance in patients with complex or severe comorbidities.

According to the invention the compounds are used for treating other pathologies in which the local and concomitant inhibition of VEGF- and Fyn would produce benefits.

In particular, they comprise the eye diseases such as intraocular neovascular disorders, such as age-related macular degeneration, diabetic macular oedema and other ischaemia-related retinopathies, or immune-mediated corneal graft rejection; skin disorders such as psoriasis, a common autoimmune disease, which is characterized as hyperplastic epidermis and hyper-angiogenesis dermis; or rosacea, a common chronic condition affecting mainly the facial skin and characterised by visible blood vessels, central facial erythema and often papules and pustule; acute or chronic pain, lung diseases such as acute respiratory distress syndrome (ARDS), Idiopathic Pulmonary Fibrosis (IPF), Hypersensitivity Pneumonitis (HP) and Systemic Sclerosis (SSc); and certain cancers such as metastatic colorectal cancer, non-squamous non-small cell lung cancer, metastatic renal cell carcinoma, recurrent glioblastoma multiforme, gynaecological malignancies, metastatic breast cancer.

In a preferred aspect the compound of the invention is disclosed for use in the treatment of acute and chronic pain selected from neuropathic pain, inflammatory pain, osteoarthritis pain, ocular pathology pain.

Preferably the composition of the invention is used in a pharmaceutical composition together with pharmaceutically acceptable carriers and excipients.

The composition hence can comprise also pharmaceutically acceptable excipients and can be administered in a pharmaceutical form suitable for the desired administration route.

Pharmaceutically acceptable additives can be excipients, ligands, dispersing agents, colorants, humectants, commonly used for the preparation of tablets, capsules, pills, solutions, suspensions, emulsions for oral administration. Injectable solutions are also contemplated for parental administration, comprising subcutaneous, spinal and transdermal administration.

The pharmaceutical composition according to the present invention is preferably for intra-articular, intravenous, oral, transdermal, intrathecal, intranasal, intraperitoneal or intramuscular administration, more preferably intra-articular administration.

The compound of Formula (I) of the invention is preferably in a dose in the range from 0.25 to 500 mg/knee, more preferably is in a dose in the range from 1 to 200 mg/knee. These doses can be dissolved in a volume in the range from 0.5 mL/knee to 6 mL/knee, The pharmaceutical compositions according to the present invention can be used alone or in combination with or can comprise one or more further drugs. These drugs could include, but are not limited to, hyaluronic acid, chondroitin sulphate and glucosamine, glucosamine sulphate, and steroidal or non-steroidal anti-inflammatory drugs.

The invention will be now detailed with reference to the preparative examples of the compounds of the invention and examples for testing the inhibitory activity with illustrative and not limitative purposes.

Experimental Part

Reagents used in the following examples were commercially available from various suppliers and used without further purifications. Solvents were used in dry form. Reactions in anhydrous environment were run under a positive pressure of dry $N_2$.

Proton Nuclear Magnetic Resonance ($^1H$ NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH $C_{18}$ column (1.7 μM, 50×2.1 mm).

Chiral-HPLC spectra were performed using Agilent 1200 apparatus equipped UV-Vis detector.

Preparative HPLC was performed on Waters GX-281 HPLC system equipped with a UV-detector.

Flash silica gel chromatography was performed on Biotage automatic flash chromatography systems (Sp1 and Isolera systems) using Biotage SNAP HP silica cartridges or Biotage SNAP KP-NH cartridges.

Reverse phase chromatography was performed on Biotage automatic flash chromatography systems (Isolera systems) using RediSep Gold C-18Aq cartridges.

Purifications of some basic compounds were performed using Phenomenex Strata SCX cartridges (55 μm, 70A).

Thin layer chromatography was carried out using Merck TLC plates Kieselgel 60F-254, visualized with UV light, aqueous permanganate solution, iodine vapours.

Microwave reactions were performed on a Biotage Initiator apparatus.

The following abbreviations are used herein: CAN: acetonitrile; AcOH: acetic acid; CDI: carbonyldiimidazole; cHex: cyclohexane; DIAD: diisopropyl (E)-diazene-1,2-dicarboxylate; Boc: terbutyloxycarbonyl; $Boc_2O$: di tert-buthyl dicarbonate; DCM: dichloromethane; DCE: 1,2-dichloroethane; TFA: trifluoroacetic acid; DMF: dimethylformamide; THF: tetrahydrofuran; RT: room temperature; DMAP: dimethylamino pyridine; AcOEt: ethyl acetate; NaOH: sodium hydroxyde; KOH: potassium hydroxyde; DIPEA: N,N-diisopropylethylamine; TEA: triethyl amine; $NaHCO_3$: sodium bicarbonate; $Na_2SO_4$: sodium sulphate; $PdCl_2(PPh_3)_2$: bis(triphenylphosphine)palladium(II)chloride; $Cs_2CO_3$: cesium carbonate; DIBAL-H: diisobutylaluminium hydride; LAH: lithium aluminum hydride; tBuOK: potassium tert-buthoxide; $iPr_2O$: di-isopropyl ether; DIBAL-H: di iso buthyl aluminium hydride.

In the following schemes (5, 6, 7 and 8), the general synthetic pathways to obtain the intermediates (V, IX, XII, XVI) of schemes 1, 2, 3 and 4 are described.

Scheme 5 for obtaining intermediates (V) is reported below:

Scheme 5

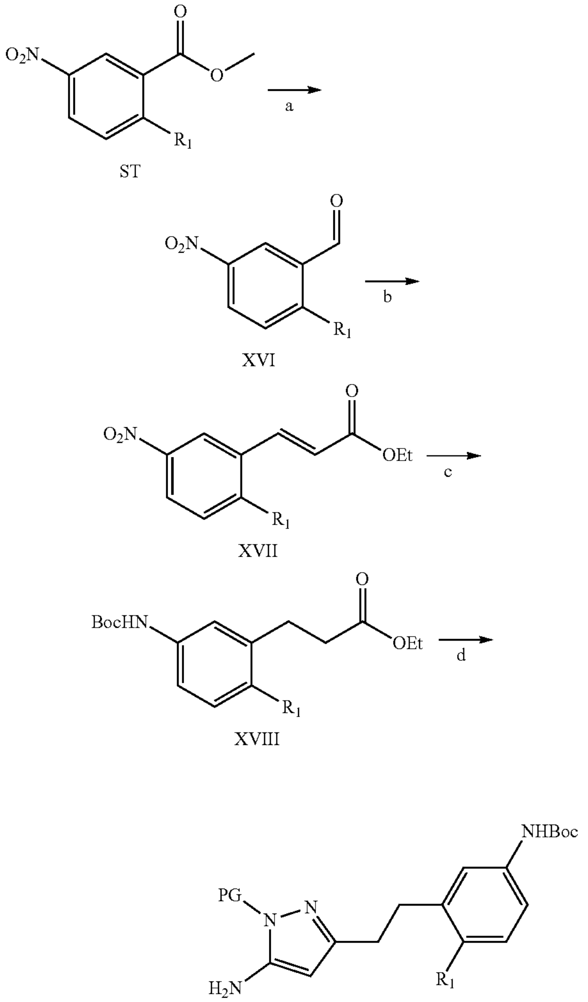

ST
XVI
XVII
XVIII
V

Scheme 5 provides the following steps:

a) Conversion of starting materials in compounds of formula XVI using a reducing agent such as DIBAL-H in DCM as solvent; $R_1$ could be=F, Cl, Me b) Wittig reaction using ethyl 2-(triphenylphosphoranylidene)acetate in water to obtain intermediates XVII;

c) Reduction of double bond and nitro group under hydrogen atmosphere and amine protection to obtain intermediates of formula XVIII;

d) Formation of the amino pyrazole derivatives (V) using tert butyl hydrazine in polar solvent such as for example ethanol.

Scheme 6

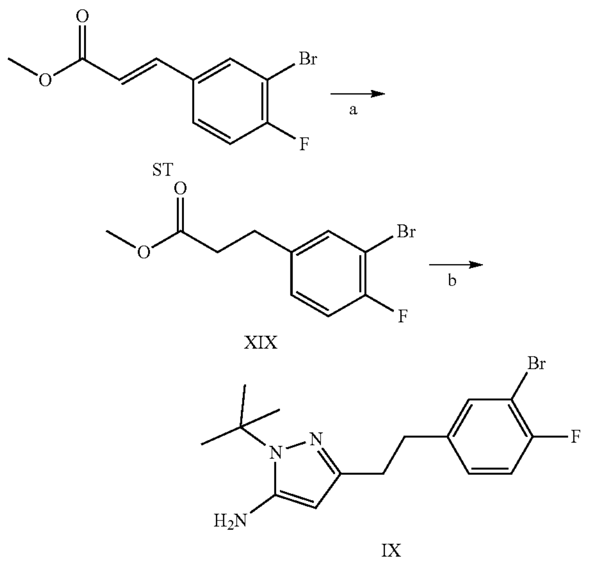

ST
XIX
IX

Scheme 6 provides the following steps:
a) Reduction of double bond under hydrogen atmosphere to obtain intermediate XIX;
b) Formation of the amino pyrazole derivative IX using tert butyl hydrazine in polar solvent such as for example ethanol.

Scheme 7

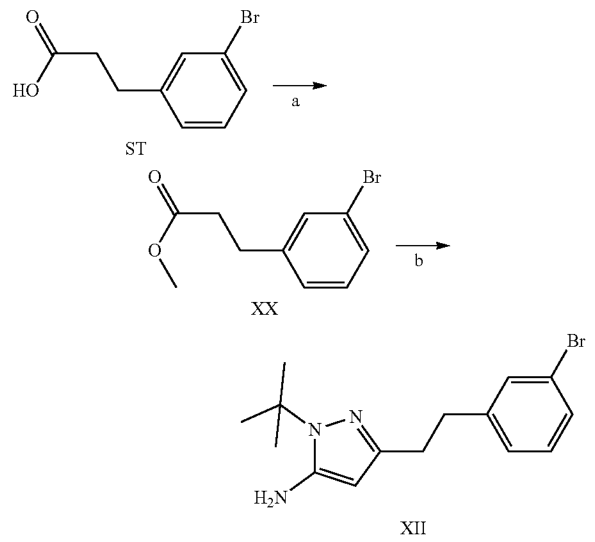

ST
XX
XII

Scheme 7 provides the following steps:
a) Ester formation using thionyl chloride in MeOH;
b) Formation of the amino pyrazole derivative (XII) using tert butyl hydrazine in polar solvent such as for example ethanol.

Scheme 8

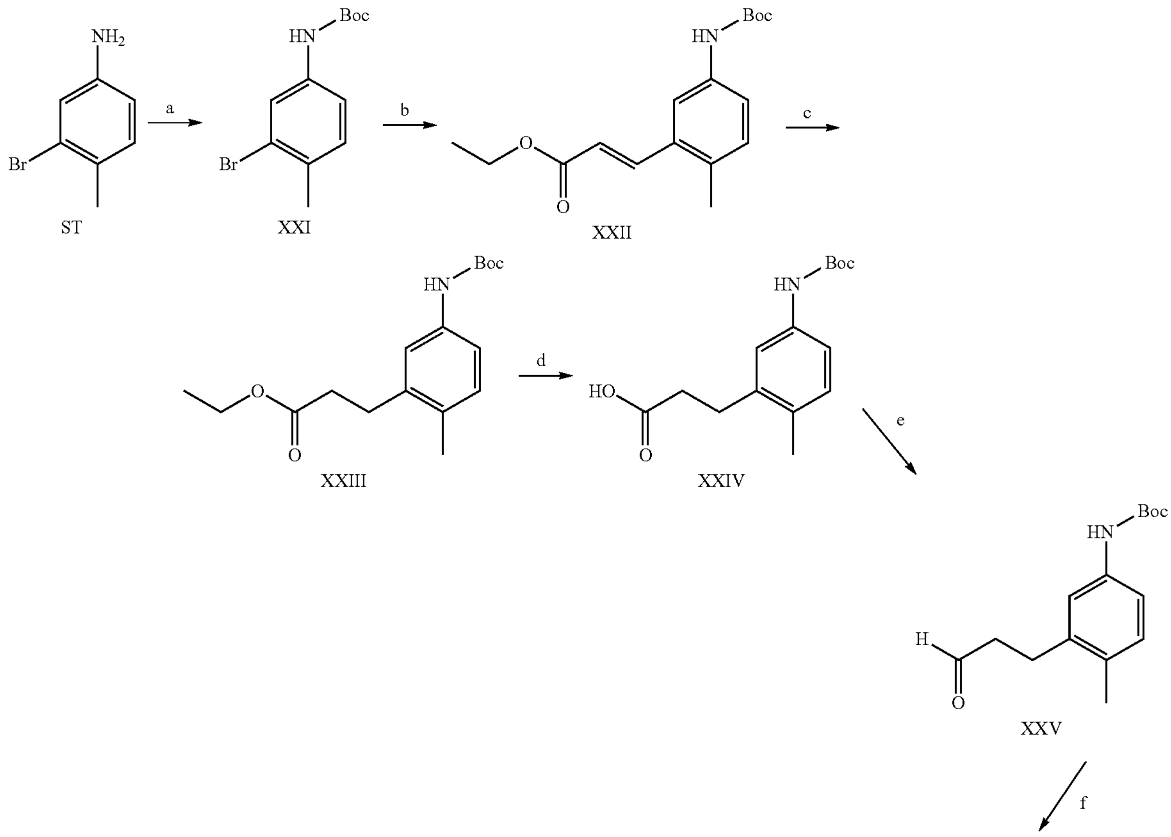

ST
XXI
XXII
XXIII
XXIV
XXV

-continued

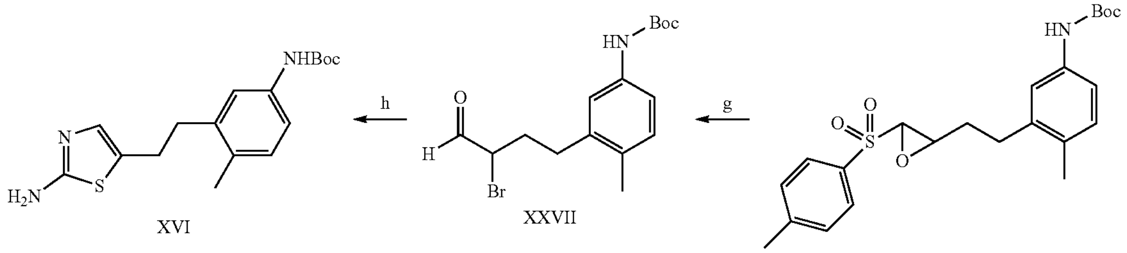

XVI XXVII XXVI

Scheme 8 provides the following steps:

a) Starting material amine protection to obtain intermediates XXI;

b) Conversion of intermediates of formula XXI into compounds XXII using ethyl acrylate in the presence of palladium catalyst and triphenylphosphine;

c) Reduction of double bond under hydrogen atmosphere in EtOH/Ethyl acetate;

d) Reduction of ester group using a reducing agent such as LAH in THF;

e) Oxidation of intermediates XXIV using oxidant such as $MnO_2$ to obtain aldehydes XXV;

f) Reaction of intermediates XXV with 1-((chloromethyl) sulfonyl)-4-methyl benzene in a base such as tBuOK in THF to obtain intermediates XXVI;

g) Formation of bromo aldehydes XXVII using $MgBr_2$;

h) Formation of intermediates XVI by reaction of intermediates XXVII with thiourea in THF/water.

Example 1

Preparation of Intermediate (XVI) (Intermediates 1-3) of Scheme 5

General Procedure 1

DIBAL-H 1M in DCM (67.6 ml, 67.6 mmol) was added dropwise to a stirred solution of the nitrobenzoate (56.4 mmol) in DCM (300 ml) at −78° C. After 20 min stirring at −78° C., a mixture of DCM (150 mL) and the saturated Rochelle salt solution (250 mL) were added. After being stirred vigorously at room temperature for 1 hour, the resulting mixture was separated. The organic layer was washed with brine and dried over $Na_2SO_4$, filtered, and concentrated under reduced pressure to afford title compounds as clear oils.

Intermediates 1-3: Intermediate (XVI) of scheme 5

| Intermediate | Structure | MS | Yields (%) |
|---|---|---|---|
| 1 | 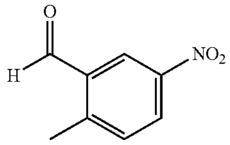 | ESI + m/z 166[M + H] | 55 |
| 2 | 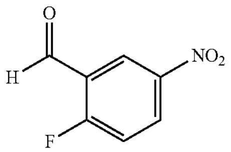 | ESI + m/z 170[M + H] | 72 |
| 3 | 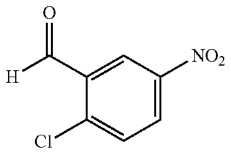 [SMILES: O=Cc1cc([N+](=O)[O-])ccc1Cl] | ESI + m/z 186[M + H] | 75 |

Example 2

Preparation of Intermediate (XVII) (Intermediates 4-6) of Scheme 5

General Procedure 2

A mixture of ethyl 2-(triphenylphosphoranylidene)acetate (21.09 g, 60.6 mmol) and the nitrobenzaldehyde (60.6 mmol) in water was heated at 90° C. for 1 h.

The suspension was cooled to RT, extracted with DCM, dried over $Na_2SO_4$ and concentrated. The crude was suspended in a mixture of cyclohexane and DCM, the precipitate was eliminated by filtration and the filtrate was concentrated and purified via silica gel column (340 g) eluting with cyclohexane to cyclohexane/AcOEt 8/2 to give the title compounds as yellow solids.

| Intermediates 4-6: Intermediate (XVII) of scheme 5 | | | |
|---|---|---|---|
| Inter-mediate | Structure | $^{1}$HNMR/MS | Yield (%) |
| 4 | 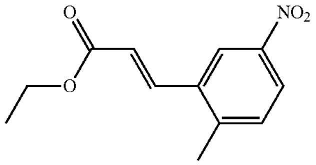 [SMILES: CCOC(=O)/C=C/c1cc([N+](=O)[O-])ccc1C] | ESI + m/z 236[M + H] | 44 |
| 5 | 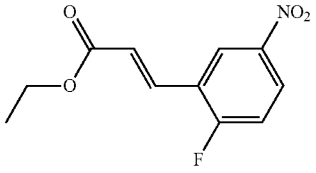 [SMILES: CCOC(=O)/C=C/c1cc([N+](=O)[O-])ccc1F] | $^{1}$H NMR (400 MHz $CDCl_3$) δ ppm 8.55 (dd, J = 2.8, 6.3 Hz, 1 H), 8.49 (dd, J = 2.8, 6.3 Hz, 2 H), 8.31-8.20 (m, 3 H), 7.81 (d, J = 16.3 Hz, 2 H), 7.33-7.27 (m, 2 H), 7.23 (t, J = 9.0 Hz, 1 H), 7.00 (d, J = 12.3 Hz, 1 H), 6.68 (d, J = 16.3 Hz, 2 H), 6.24 (d, J = 12.3 Hz, 1 H), 4.32 (q, J = 7.2 Hz, 4 H), 4.20 (q, J = 7.2 Hz, 2 H), 1.38 (t, J = 7.1 Hz, 6 H), 1.26 (t, J = 7.1 Hz, 3 H). ESI + m/z 240[M + H] | 73 |
| 6 | 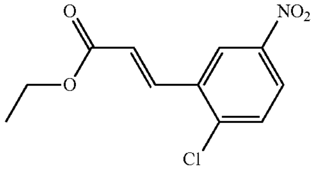 [SMILES: CCOC(=O)/C=C/c1cc([N+](=O)[O-])ccc1Cl] | ESI + m/z 256[M + H] | 62 |

Example 3

Preparation of Intermediate (XVIII) (Intermediates 7-9) of Scheme 5

General Procedure 3 To a solution of intermediates 4-6 (17.00 mmol) in TH, (75 ml), $BOC_2O$ (4.45 g, 20.41 mmol) and Pd/C (0.452 g, 0.425 mmol) were added. The resulting solution was stirred under a hydrogen atmosphere for 16 h.

The mixture was filtered to remove the catalyst and the filtrate was then concentrated and purified by on a silica gel column (100 g) eluting with cHex only to cHex/AcOEt 9:1 in 7CV to give the title compounds as off white solids.

TABLE 3

| Intermediates 7-9: Intermediate (XVIII) of scheme 5 | | | |
|---|---|---|---|
| Inter-mediates | Structure | $^{1}$HNMR/MS | Yields (%) |
| 7 | 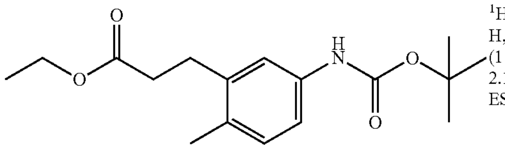 | $^{1}$H NMR (400 MHz, DMSO-$d_6$) δ ppm 9.12 (1 H, s), 7.27 (1 H, s), 7.08-7.19 (1 H, m), 7.00 (1 H, d), 4.06 (2 H, q), 2.71-2.83 (2 H, m), 2.19 (3 H, s), 1.47 (9 H, s), 1.18 (3 H, t). ESI + m/z 308[M + H] | 65 |
| 8 | 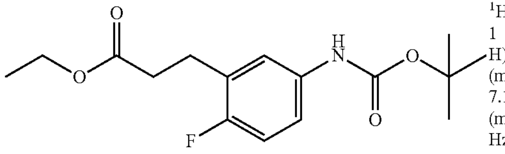 | $^{1}$H NMR (400 MHz, DMSO-$d_6$) δ ppm 9.28 (s, 1 H), 7.41 (dd, J = 2.3, 6.7 Hz, 1 H), 7.30-7.20 (m, 1 H), 7.03 (t, J = 9.4 Hz, 1 H), 4.05 (q, J = 7.1 Hz, 2 H), 2.86-2.76 (m, 2 H), 2.60-2.53 (m, 2 H), 1.51-1.42 (m, 9H), 1.16 (t, J = 7.2 Hz, 3 H). ESI + m/z 312[M + H] | 70 |
| 9 | 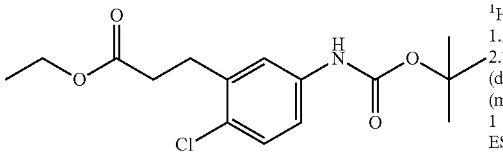 | $^{1}$H NMR (400 MHz, DMSO-$d_6$) δ ppm 1.13-1.22 (m, 3 H) 1.48 (s, 9 H) 2.54-2.61 (m, 2 H) 2.74-2.93 (m, 2H) 4.01-4.11 (m, 2H) 7.15 (d, J = 7.83 Hz, 1 H) 7.29 (s, 1 H) 7.32-7.52 (m, 1 H) 9.14-9.47 (m, 1 H). ESI + m/z 328[M + H] | 47 |

Example 4

Preparation of Intermediate (V) (Intermediates 10-14) of Scheme 5

General Procedure 4 To nBuLi in hexane (11.06 ml, 27.7 mmol) in dry THF (52.7 ml) at −78° C., acetonitrile (1.444 ml, 27.7 mmol) was added dropwise maintaining the temperature below −65° C. Once addition was complete, the reaction was left to stir at −78° C. for 1 hour. After this time, a solution of intermediate 7, 8 or 9 (11.06 mmol) in THF (10 ml) was added dropwise again maintaining the temperature always below −65° C. Once addition was complete, the reaction was left to stir for 1 hour at −78° C. After this time, the reaction was quenched with 10% w/v aqueous citric acid (20 ml) and it was warmed to RT. HCl 1M (20 ml) was then added until pH 3 and the product was extracted twice with $iPr_2O$.

The organic phase was washed with brine, dried and evaporated under reduced pressure to give a yellow oil. The intermediate was dissolved in Ethanol (105 ml), hydrazine hydrochloride salt or tert-butylhydrazine hydrochloride salt (33.2 mmol) was then added and the resulting mixture was heated to reflux for 3 h.

The reaction was cooled to RT and ethanol was evaporated under vacuum. To the remaining residue was added DCM (40 ml) and water/$NaHCO_3$. After brief mixing, the two layers were separated and the organic layer was then dried over anhydrous sodium sulphate and evaporated.

The resulting residue was loaded on a silica gel column (100 g; gradient: from DCM to DCM/$iPr_2O$ 9/1) to give the title compounds as off white solids.

Intermediates 10-14: Intermediate (V) of scheme 5

| Intermediates | Structure | $^1$HNMR/MS | Yields (%) |
|---|---|---|---|
| 10 | 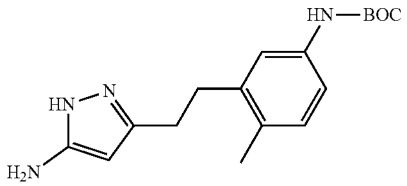 [SMILES: Cc1ccc(NC(=O)OC(C)(C)C)cc1CCc1cc(N)[nH]n1] | $^1$H NMR (400 MHz, DMSO-d$_6$) δ ppm 9.13 (1 H, s), 7.31 (1 H, s), 7.10-7.20 (1 H, m), 7.00 (1 H, d), 5.24 (1 H, s), 2.73 (2 H, m), 2.62 (2 H, m), 2.19 (3 H, s), 1.47 (9 H, s)<br>ESI + m/z 317 [M + H] | 71 |
| 11 | 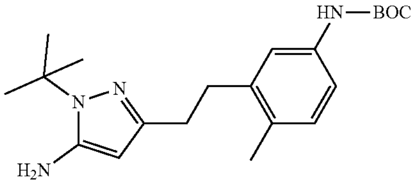 | $^1$H NMR (400 MHz, DMSO-d$_6$) δ ppm 9.10 (1 H, s), 7.30 (1 H, s), 7.15 (1 H, d), 6.98 (1 H, d), 5.24 (1 H, s), 4.71 (2 H, s), 2.68 (2 H, s), 2.18 (3 H, s), 1.50 (9 H, s), 1.47 (9 H, s)<br>ESI + m/z 373 [M + H] | 75 |
| 12 | 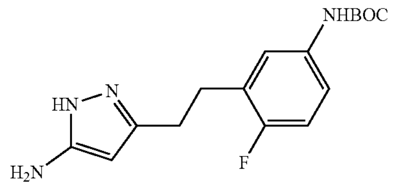 | $^1$H NMR (400 MHz, DMSO-d$_6$) δ ppm 9.28 (1 H, br. s.), 7.37-7.47 (1 H, m), 7.25 (1 H, d, J = 2.93 Hz), 7.02 (1 H, t, J = 9.29 Hz), 5.20 (1 H, s), 4.15-4.87 (1 H, m), 2.76-2.85 (2 H, m), 2.63-2.73 (2 H, m), 1.47 (9 H, s).<br>ESI + m/z 321 [M + H] | 71 |
| 13 | 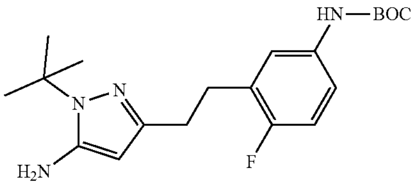 | $^1$H NMR (400 MHz, DMSO-d$_6$) δ ppm 9.17-9.32 (1 H, m), 7.37-7.47 (1 H, m), 7.23 (1 H, d, J = 3.42 Hz), 7.01 (1 H, t, J = 9.29 Hz), 5.23 (1 H, s), 4.73 (2 H, s), 2.70-2.81 (2 H, m), 2.53-2.61 (2 H, m), 1.48 (18 H, d, J = 8.80 Hz).<br>ESI + m/z 377 [M + H] | 45 |
| 14 | 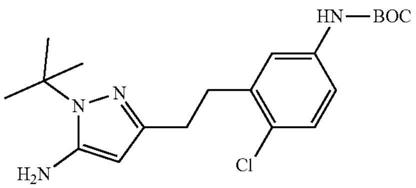 [SMILES: CC(C)(C)OC(=O)Nc1ccc(Cl)c(CCc2cc(N)n(C(C)(C)C)n2)c1] | $^1$H NMR (400 MHz, DMSO-d$_6$) δ ppm 9.38 (1 H, s), 7.49 (1 H, s), 7.27 (2 H, s), 5.25 (1 H, s), 4.72 (2 H, s), 2.75-2.88 (2 H, m), 2.53-2.61 (2 H, m), 1.49 (18 H, d, J = 9.78 Hz).<br>ESI + m/z 394 [M + H] | 29 |

Example 5

Preparation of Intermediate (XIX) (Intermediate 15) of Scheme 6 methyl 3-(3-bromo-4-fluorophenyl)propanoate

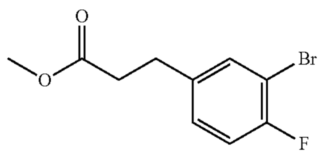

To (E)-methyl 3-(3-bromo-4-fluorophenyl)acrylate (5.3 g, 20.46 mmol) in THF (30 ml) was added rhodium on carbon 5% (1.179 g, 0.573 mmol). The resulting solution was placed under a hydrogen atmosphere (1 bar; RT).

The reaction was filtered to remove catalyst. The filtrate was then concentrated under vacuum to remove the solvent. Yield 5.34 g (yellow oil).

$^1$H NMR (400 MHz, DMSO-$d_6$) δ ppm 7.55-7.64 (1H, m), 7.22-7.34 (2H, m), 3.53-3.65 (3H, m), 2.79-2.91 (2H, m), 2.59-2.72 (2H, m).

ESI+m/z 262 [M+H]

Example 6

Preparation of Intermediate (IX) (Intermediate 16) of Scheme 6

3-(3-bromo-4-fluorophenethyl)-1-(tert-butyl)-1H-pyrazol-5-amine

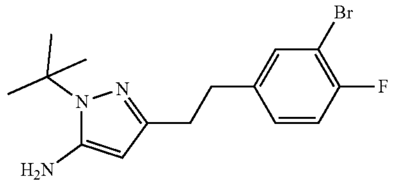 [SMILES: CC(C)(C)n1nc(CCc2ccc(F)c(Br)c2)cc1N]

To n-Butyl lithium in hexane (17.72 ml, 44.3 mmol) in dry THF (100 ml) at −78° C. was added dropwise, maintaining the temperature below −65° C., acetonitrile (2.314 ml, 44.3 mmol). Once addition was complete, the reaction was left to stir at −78° C. for 1 hour. After this time, methyl 3-(3-bromo-4-fluorophenyl)propanoate (5.34 g, 22.15 mmol) was added dropwise maintaining the temperature always below −65° C. Once addition was complete, the reaction was left to stir for 1 hour at −78° C. After this time, the reaction was quenched with 1M aqueous HCl (5 ml). The reaction was warmed to RT and then stripped of organic solvents under vacuum.

To the remaining solution was added 1M aqueous HCl (15 ml) followed by DCM (50 ml). After brief mixing, the organic layer was separated, dried over anhydrous sodium sulphate and then evaporated to a yellow oil.

To this yellow oil was then added ethanol (150 ml) followed by tert-butylhydrazine hydrochloride (4.14 g, 33.2 mmol) and sodium hydroxide (1.240 g, 31.0 mmol). The resulting mixture was then heated to reflux overnight. The next day the reaction was cooled to RT and then stripped of ethanol.

To the remaining residue was added water (50 ml), saturated aqueous sodium bicarbonate (50 ml) and DCM (100 ml). After brief mixing, the organic layer was separated, dried over anhydrous sodium sulphate and then evaporated to a brown oil. Purification: KP-NH silica gel column (110 g) eluting with cyHex/DCM 70:30. Yield: 6.64 g (yellow solid).

$^1$H NMR (400 MHz, DMSO-$d_6$) δ ppm 7.55 (1H, dd), 7.21-7.28 (2H, m), 5.20 (1H, s), 4.72 (2H, s), 2.74-2.86 (2H, m), 2.54-2.65 (2H, m), 1.49 (9H, s).

ESI+m/z 341 [M+H]

Example 7

Preparation of Intermediate (XX) (Intermediate 17) of Scheme 7 methyl 3-(3-bromophenyl)propanoate

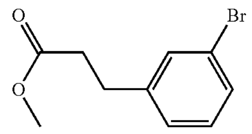

To 3-(3-bromophenyl)propanoic acid (5 g, 21.83 mmol) in dry methanol (44 ml) was added sulfurous dichloride (4.75 ml, 65.5 mmol) dropwise. Once addition was complete, the reaction was allowed to warm to RT and left to stand overnight. After stirring overnight, the reaction was evaporated and dried under high vacuum. Yield 5.35 g (colorless oil).

$^1$H NMR (400 MHz, DMSO-$d_6$) δ ppm 7.35-7.50 (2H, m), 7.21-7.28 (2H, m), 3.59 (3H, s), 2.77-2.91 (2H, m), 2.59-2.70 (2H, m).

ESI+m/z 245 [M+H]

Example 8

Preparation of Intermediate (XII) (Intermediate 18) of Scheme 7

3-(3-bromophenethyl)-1-(tert-butyl)-1H-pyrazol-5-amine

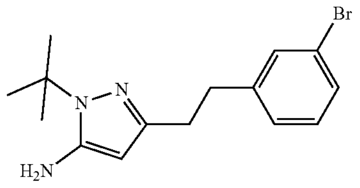 [SMILES: CC(C)(C)n1nc(CCc2cccc(Br)c2)cc1N]

To nBuLi in hexane (17.90 ml, 44.8 mmol) in dry $Et_2O$ (100 ml), acetonitrile (2.338 ml, 44.8 mmol) was added dropwise at −78° C., maintaining the temperature below −65° C. Once addition was complete, the reaction was left to stir at −78° C. for 1 hour. After this time, intermediate 17 (5.44 g, 22.38 mmol) was added dropwise maintaining the temperature always below −65° C. Once addition was complete, the reaction was left to stir for 1 hour at −78° C. The reaction was therefore quenched with 1M aqueous HCl (20 ml), warmed to RT and then stripped of organic solvents under vacuum.

To the remaining aqueous solution was added more 1M aqueous HCl (35 ml) followed by DCM (50 ml). The organic phase was then dried over anhydrous sodium sulphate and evaporated to a yellow-brown oil.

This intermediate was dissolved in Ethanol (200 ml), tert-butylhydrazine hydrochloride (4.18 g, 33.6 mmol) and NaOH (1.253 g, 31.3 mmol) were then added. The resulting mixture was heated to reflux for 3 h, then cooled to RT and ethanol was evaporated under vacuum. To the remaining residue, DCM (100 ml) and dilute aqueous sodium bicarbonate solution were added. After brief mixing, the two layers were separated and the organic layer was then dried over anhydrous sodium sulphate. Purification: KP-NH silica gel column (110 g) eluting with gradient cyclohexane/DCM 9:1 to cyclohexane/DCM 1:1. Yield 5.60 g (off white solid)

$^1$H NMR (400 MHz, $CDCl_3$) δ ppm 7.39 (d, J=1.5 Hz, 1H), 7.33 (td, J=2.2, 6.8 Hz, 1H), 7.16 (s, 1H), 7.15 (s, 1H), 5.37 (s, 1H), 2.94-2.88 (m, 2H), 2.85-2.77 (m, 2H), 1.65 (s, 9H).

ESI+m/z 323 [M+H]

Example 9

Preparation of Intermediate (XXI) (Intermediate 19) of Scheme 8 tert-butyl (3-bromo-4-methylphenyl)carbamate

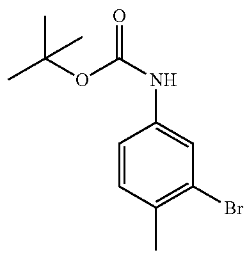 [SMILES: Cc1ccc(NC(=O)OC(C)(C)C)cc1Br]

To a solution of 3-bromo-4-methylaniline (50.0 g, 0.269 mol), $NaHCO_3$ (45.2 g, 0.538 mol) in MeOH (300 mL) and $H_2O$ (150 mL), was added $Boc_2O$ (70.0 g, 0.322 mol) slowly at 20-30° C. and the mixture was stirred at room temperature for 16 h. The mixture was then concentrated and the crude was diluted with DCM (800 mL), filtered and washed with $H_2O$ (2*100 mL). The combined organics were dried over $Na_2SO_4$ and concentrated to afford 74.5 g of title intermediate as white solid.

ESI+m/z 286 [M+H]

Example 10

Preparation of Intermediate (XXII) (Intermediate 20) of Scheme 8 ethyl (E)-3-(5-((tert-butoxycarbonyl)amino)-2-methylphenyl)acrylate

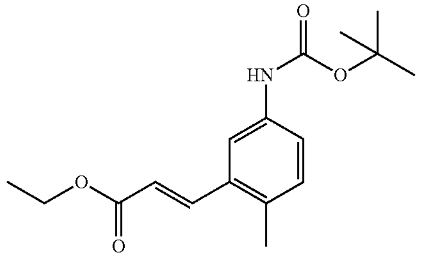 [SMILES: CCOC(=O)/C=C/c1cc(NC(=O)OC(C)(C)C)ccc1C]

To a solution of intermediate 19 (74.5 g, 0.26 mol), TEA (105.0 g, 1.04 mol) and ethyl acrylate (260.0 g, 2.6 mol) in toluene (600 ml), was added $Pd(OAc)_2/PPh_3$ (5.0 g/13.6 g) at room temperature, then the mixture was stirred at 112° C. for 4 days. The mixture was concentrated and purified by flash chromatography on silica gel (Petroleum ether:AcOEt from 50:1 to 5:1) to afford title intermediate (75 g) as a white solid.

ESI+m/z 306 [M+H]

Example 11

Preparation of Intermediate (XXIII) (Intermediate 21) of Scheme 8 ethyl 3-(5-((tert-butoxycarbonyl)amino)-2-methylphenyl)propanoate

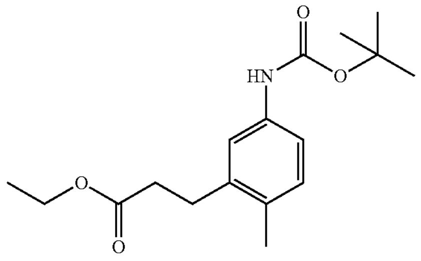 [SMILES: CCOC(=O)CCc1cc(NC(=O)OC(C)(C)C)ccc1C]

To a solution of intermediate 20 (75.0 g, 0.245 mol) in ethyl acetate (600 mL) and ethanol (1200 mL), was added Pd/C (6.0 g, 10%) and the mixture was stirred at 35° C. under hydrogen atmosphere (50 psi) for 2 days. The mixture was filtered and concentrated to afford intermediate 21 (65 g) as a light grey solid.

ESI+m/z 308 [M+H]

Example 12

Preparation of Intermediate (XXIV) (Intermediate 22) of Scheme 8 tert-butyl (3-(3-hydroxypropyl)-4-methylphenyl)carbamate

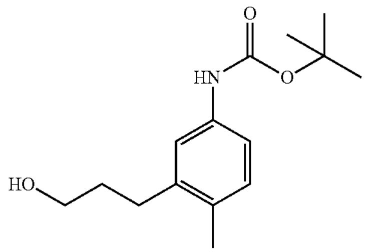 [SMILES: Cc1ccc(NC(=O)OC(C)(C)C)cc1CCCO]

To a solution of intermediate 21 (8.0 g, 26.0 mmol) in THF (30 mL) was added $LiAlH_4$(1.0 g, 26.0 mmol) in $Et_2O$ (30 mL) at 0-5° C., then the mixture was stirred at RT for 3 hours. The mixture was quenched with 1 mL of $H_2O$ followed by 1 mL of 15% NaOH and 3 mL of $H_2O$, filtered and the filtrate was concentrated to afford intermediate 22 (6.9 g) as a white solid. ESI+m/z 266 [M+H]

Example 13

Preparation of Intermediate (XXV) (Intermediate 23) of Scheme 8 tert-butyl (4-methyl-3-(3-oxopropyl)phenyl)carbamate

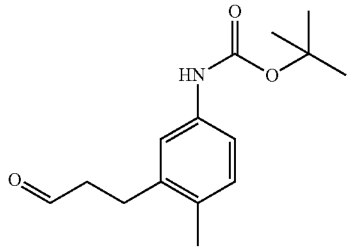 [SMILES: Cc1ccc(NC(=O)OC(C)(C)C)cc1CCC=O]

To a solution of crude intermediate 22 (6.9 g, 26.0 mmol) in dry DCM (100 mL) was added PCC (1.2 g, 18.3 mmol), then the mixture was stirred at RT overnight. After the reaction was completed, the mixture was concentrated and purified by flash chromatography on silica gel (Petroleum ether:AcOEt from 30:1 to 10:1) to afford title intermediate (3.5 g) as a yellow oil.

ESI+m/z 264 [M+H]

Example 14

Preparation of Intermediate (XXVI) (Intermediate 24) of Scheme 8 tert-butyl (4-methyl-3-(2-(3-tosyloxiran-2-yl)ethyl) phenyl)carbamate

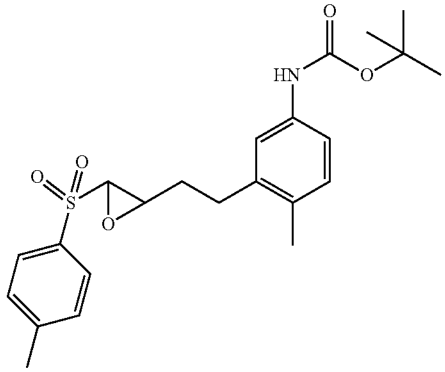 [SMILES: Cc1ccc(S(=O)(=O)C2OC2CCc2cc(NC(=O)OC(C)(C)C)ccc2C)cc1]

To a solution of intermediate 23 (20.0 g, 0.076 mol) in THF (200 mL) was added 1-((chloromethyl)sulfonyl)-4-methylbenzene (18.6 g, 0.09 mol). After being cooled to −65° C., to the solution was added t-BuOK (10.0 g, 0.09 mol) in portions. The reaction was stirred at this temperature for 0.5 h, then at 0° C. for 0.5 h. The reaction was quenched with AcOH/water, added EtOAc (100 mL) and washed with water followed by brine.

Purification: flash chromatography on silica gel (Petroleum ether:AcOEt 40:1) to afford title intermediate (13.0 g) as a yellow solid.

ESI+m/z 432 [M+H]

Example 15

Preparation of Intermediate (XXVII) (Intermediate 25) of Scheme 8 tert-butyl (3-(3-bromo-4-oxobutyl)-4-methylphenyl) carbamate

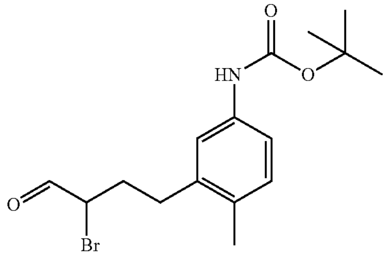 [SMILES: Cc1ccc(NC(=O)OC(C)(C)C)cc1CCC(Br)C=O]

To a solution of intermediate 24 (8.0 g, 18.5 mmol) in $Et_2O$ (300 mL) was added $MgBr_2 \cdot Et_2O$ (6.0 g, 23.0 mmol). After 18 hours at RT, water (50 mL) was added and the reaction was filtered.

The filtrate was separated and the organic phase was washed with water, brine, dried over $Na_2SO_4$ and evaporated to afford title intermediate (6.0 g) as a yellow solid.

ESI+m/z 357 [M+H]

Example 16

Preparation of Intermediate (XVI) (Intermediate 26) of Scheme 8 tert-butyl (3-(2-(2-aminothiazol-5-yl)ethyl)-4-methylphenyl)carbamate

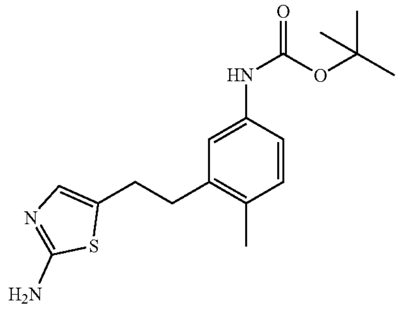 [SMILES: Cc1ccc(NC(=O)OC(C)(C)C)cc1CCc1cnc(N)s1]

To a solution of intermediate 25 (6.0 g, 16.8 mmol) in 1,4-dioxane (60 mL) and water (12 mL), thiourea (2.56 g, 33.7 mmol) and $Et_3N$ (4.6 mL) were added, then the mixture was stirred at 90° C. for 3 h. The reaction was evaporated to dryness, added water (20 mL), extracted with AcOEt (3×30 mL) and dried over $Na_2SO_4$. Purification: flash chromatography on silica gel (DCM:MeOH=100:1) to afford title intermediate (2.5 g) as a yellow solid. 1H-NMR (300 MHz, $CDCl_3$) δ ppm 7.20 (s, 1H), 7.06-7.05 (m, 2H), 6.74 (s, 1H), 6.55 (s, 1H), 4.87 (bs, 1H), 2.87-2.84 (m, 4H), 2.23 (s, 3H), 1.53 (s, 9H).

ESI+m/z 334 [M+H]

Example 17

Preparation of Intermediate 27 methyl 4-(1-(ethylamino)cyclopropyl)benzoate

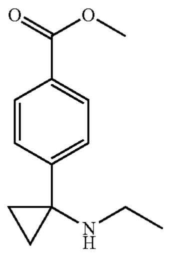 [SMILES: CCNC1(c2ccc(C(=O)OC)cc2)CC1]

A solution of methyl 4-(1-aminocyclopropyl)benzoate, hydrochloride salt (1 g, 4.39 mmol; prepared as described in WO2008104055) and acetic acid (1.257 ml, 21.96 mmol) in DCE (30 ml) was stirred for 30 minutes, then sodium triacetoxyborohydride (1.396 g, 6.59 mmol) was added and the resulting mixture was left stirring at RT overnight.

The reaction was treated with saturated $NaHCO_3$ and extracted with DCM (300 ml). The organic layer was washed with water, dried and concentrated. The residue purified by reverse phase chromatography (50 g), from water/0.1% AcOH to $CH_3CN$/0.1% AcOH) to give the title compound as light yellow oil (Yield 0.8 g).

$^1H$ NMR (400 MHz, DMSO-$d_6$) δ ppm 7.87 (1H, d), 7.43 (1H, d), 3.84 (3H, s), 2.44 (2H, q), 0.91-1.05 (7H, m).

ESI+m/z 220 [M+H]

Example 18

Preparation of Intermediate 28

4-(1-(ethylamino)cyclopropyl)benzoic acid

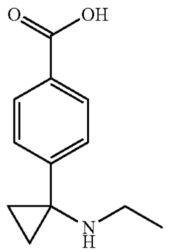

To intermediate 27 (0.8 g, 3.65 mmol) in Dioxane (10 ml) was added lithium hydroxide hydrate (0.184 g, 4.38 mmol) dissolved in water (10 ml). After 1 hour at RT, the reaction was concentrated and the residue was acidified with acetic acid (0.47 ml, 8.21 mmol) and purified by reverse phase chromatography (50 g, water/AcOH 0.1% to ACN/AcOH 0.1%). Yield 235 mg (white solid).

$^1H$ NMR (400 MHz, DMSO-$d_6$) δ ppm 7.91 (2H, d), 7.38 (2H, d), 2.14 (6H, s), 0.89 (2H, d), 0.78 (2H, d).

ESI+m/z 206 [M+H]

Example 19

Preparation of Intermediate 29

4-(cyclopropylsulfonyl)picolinic acid

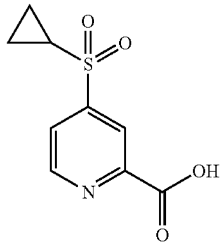 [SMILES: O=C(O)c1cc(S(=O)(=O)C2CC2)ccn1]

A mixture of Methyl 4-chloropicolinate (536 mg, 3.12 mmol), Sodium Cyclopropanesulfinate (400 mg, 3.12 mmol), Leucoline (40.3 mg, 0.312 mmol) and Copper (I) chloride (30.9 mg, 0.312 mmol) in NMP (5.5 ml) was heated at 150° C. for 1.5 h. Sodium Cyclopropanesulfinate (50 mg, 0.390 mmol) was added and the reaction mixture was left stirring at 150° C. for further 12 h. The reaction was acidified and loaded on reverse phase cartridges (50 g) eluting with $H_2O$—AcOH (0.1%)/$CH_3CN$—AcOH (0.1%). The residue was dissolved in water/EtOH and Lithium hydrate (131 mg, 3.12 mmol) was added. The reaction mixture was left stirring at room temperature for 2 h.

Ethanol was evaporated and the crude was loaded on reverse phase cartridges (50 g) eluting with $H_2O$—AcOH (0.1%)/$CH_3CN$—AcOH (0.1%). Yield 300 mg off white solid.

$^1H$ NMR (400 MHz, DMSO-$d_6$) δ ppm 14.01-13.45 (m, 1H), 9.09-9.01 (m, 1H), 8.41-8.34 (m, 1H), 8.16-8.09 (m, 1H), 3.17-3.07 (m, 1H), 1.27-1.09 (m, J=4.4 Hz, 4H).

ESI+m/z 228 [M+H]

Example 20

Preparation of Intermediate 30

2-(4-methylpyridin-2-yl)propan-2-ol

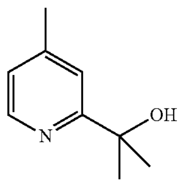

Under a dry $N_2$ atmosphere in a 2-necked flask, 1-(4-methylpyridin-2-yl)ethanone (1.9 g, 14.06 mmol) was dissolved in THF (40 ml). The flask was cooled in an ice bath, and to it was added dropwise a solution of MeMgBr in tertButyl ether (45 ml, 45.0 mmol). The solution was warmed to 40° C. and stirred for 3 hours. The reaction mixture was then cooled in an ice bath and quenched by addition of saturated aqueous $NH_4Cl$ (100 ml), then extracted with diethyl ether (5×40 ml); organics were washed with saturated aqueous NaCl, dried with anhydrous $Na_2SO_4$ and concentrated under reduced pressure. The residue was purified by silica gel chromatography (50 g) eluting with Cyclohexane/AcOEt 9/1 to Cyclohexane/AcOEt 7/3. Yield 1.09 g (light yellow oil).

$^1H$ NMR (400 MHz, $CDCl_3$) δ ppm 8.37 (1H, d), 7.19 (1H, d), 6.97-7.07 (1H, m), 5.12 (11H, br. s.), 2.39 (3H, s), 1.54 (6H, s).

ESI+m/z 152 [M+H]

Example 21

Preparation of Intermediate 31

2-(2-hydroxypropan-2-yl)isonicotinic acid

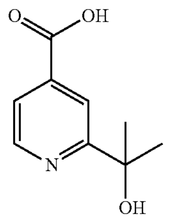

A solution of intermediate 30 (500 mg, 3.31 mmol) in water (15 ml) at 60° C. was treated with $KMnO_4$ (12 mmol). The reaction was heated to reflux for 20 h. The suspension was cooled to rt and then filtered through celite. The pH was adjusted to 2 by addition of 1N HCl and the aqueous phase was washed with AcOEt. The aqueous layer was neutralised by adding solid $NaHCO_3$ and concentrated to minimum volume, acidified with AcOH and loaded onto a reverse phase column (50 g) eluting with water+0.1% AcOH only to acetonitrile+0.1% AcOH only. Yield 322 mg (white solid).

$^1H$ NMR (400 MHz, DMSO-$d_6$) δ ppm 8.51 (1H, d), 8.07 (1H, s), 7.57 (1H, d), 4.95-5.57 (1H, m), 1.44 (6H, s).

ESI+m/z 182 [M+H]

Example 22

Preparation of Intermediate 32

3-(N,N-dimethylsulfamoyl)benzoic acid

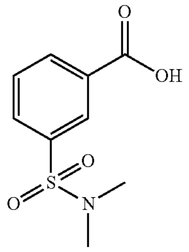

To 3-(chlorosulfonyl)benzoic acid (500 mg, 2.26 mmol) in THF (6 ml), dimethylamine (5.6 mL, 11.3 mmol) was added under nitrogen. The resulting mixture was left to stir at RT overnight. The reaction was then stripped of solvent, AcOH (0.5 mL) and water (5 mL) were added and the resulting white solid was filtered and dried under vacuum at 50° C. for 5 h to give 3-(N,N-dimethylsulfamoyl)benzoic acid (420 mg).

$^1H$ NMR (400 MHz, DMSO-$d_6$) δ ppm 13.51 (1H, s), 8.25 (1H, d, J=7.83 Hz), 8.21 (1H, s), 7.97-8.03 (1H, m), 7.78-7.84 (1H, m), 2.65 (6H, s).

ESI+m/z 230 [M+H]

Example 23

Preparation of Intermediate 33

3-(isopropylsulfonyl)benzoic acid

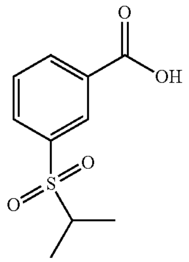

To 3-sulfinobenzoic acid (500 mg, 2.69 mmol) and potassium carbonate (1113 mg, 8.06 mmol) in DMF (10 ml), 2-iodopropane (1.611 ml, 16.1 mmol) was added slowly. The reaction was stirred at RT under nitrogen for 3 days.

To hydrolize the intermediate ester, NaOH (400 mg, 10 mmol) was added and the mixture was left to stir at RT overnight. The reaction was stripped of solvents. To the remaining residue DMSO (0.5 ml) and AcOH (0.8 mL) were then added. The resulting solution was loaded onto a reverse phase column (50 g; water+0.1% AcOH only to ACN+0.1% AcOH in 12CV). Yield 290 mg (pale yellow solid).

$^1$H NMR (400 MHz, methanol-d4) δ ppm 8.49 (1H, t, J=1.71 Hz), 8.34-8.41 (1H, m), 8.12 (1H, d, J=7.83 Hz), 7.79 (1H, s), 3.35-3.45 (1H, m), 1.29 (6H, d, J=6.85 Hz).

ESI+m/z 227 [M−H]

Example 24

Preparation of Intermediate 34

1-(6-chloro-1,3-dihydro-2H-pyrrolo[3,4-c]pyridin-2-yl)ethan-1-one

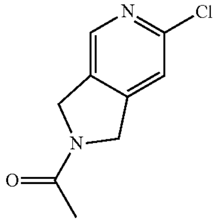

Acetyl chloride (0.345 ml, 4.85 mmol) was added to a cooled (0° C.) solution of 6-chloro-2,3-dihydro-1H-pyrrolo[3,4-c]pyridine (500 mg, 3.23 mmol, prepared as in WO2006082001) and DIPEA (0.847 ml, 4.85 mmol) in DCM (50 ml). The resulting mixture was stirred at RT ofr 16 hours, then water was added and the phases were separated. Organic layer was concentrated and loaded on a silica gel column (25 g) eluted with DCM/MeOH from 10/0 to 9/1 in gradient. Solvents were evaporated to afford the title compound (538 mg, off white solid).

$^1$H NMR (400 MHz, DMSO-$d_6$) δ ppm 8.41 (d, J=2.4 Hz, 1H), 7.56 (d, J=1.0 Hz, 1H), 4.86 (s, 2H), 4.63 (s, 2H), 2.06 (d, J=3.4 Hz, 3H).

ESI+m/z 197 [M−H]

Example 25

Preparation of Intermediate 35

2-(2-cyanopropan-2-yl)isonicotinic acid

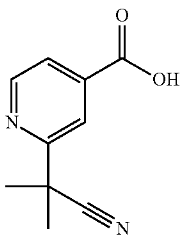

Prepared as described in WO2014151616

Example 26

Preparation of Intermediate 36

42-(4-(4,4,5,5-tetramethyl-1,3,2-dioxaborolan-2-yl)-1H-pyrazol-1-yl)ethan-1-ol

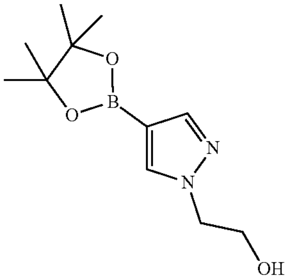 [SMILES: CC1(C)OB(c2cnn(CCO)c2)OC1(C)C]

To 4-(4,4,5,5-tetramethyl-1,3,2-dioxaborolan-2-yl)-H-pyrazole (1 g, 5.15 mmol) in dry DMF (5 ml) was added solid $K_2CO_3$ (2.137 g, 15.46 mmol) followed by 2-bromoethanol (0.548 ml, 7.73 mmol). The resulting mixture was then heated to 80° C. for 48 hours. DMF was evaporated and to the remaining residue was added DCM (20 ml); the resulting mixture was then filtered to remove solids and evaporated to give a brown oil. Purification: silica gel column (25 g) eluted with cHex/AcOEt 1:1 to AcOEt 100%. Yield 150 mg (light yellow oil).

$^1$H NMR (400 MHz, DMSO-$d_6$) δ ppm 7.89 (1H, s), 7.57 (1H, s), 4.84 (1H, t), 4.15 (2H, t), 3.72 (2H, q), 1.25 (12H, s).

ESI+m/z 239 [M+H]

Example 27

Preparation of Intermediate 37 ethyl 4-((1-benzhydrylazetidin-3-yl)oxy)benzoate

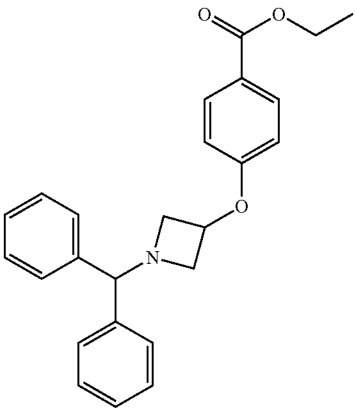 [SMILES: CCOC(=O)c1ccc(OC2CN(C(c3ccccc3)c3ccccc3)C2)cc1]

A solution of 1-benzhydrylazetidin-3-ol (2.5 g, 10.45 mmol), ethyl 4-hydroxybenzoate (1.736 g, 10.45 mmol) and triphenylphosphine (2.74 g, 10.45 mmol) in Acetonitrile (50 ml) was treated with (E)-diethyl diazene-1,2-dicarboxylate (4.76 ml, 10.45 mmol) and refluxed for 2 hours. The reaction mixture was then concentrated and the resulting residue was dissolved in DCM, washed with water and concentrated. The residue was purified by silica gel chromatography (100 g, cyHex to cyHex/AcOEt 1/1) to give title compound (4 g; colourless oil).

$^1$H NMR (400 MHz, DMSO-$d_6$) δ ppm 7.82-7.90 (2H, m), 7.41-7.48 (4H, m), 7.25-7.33 (4H, m), 7.16-7.23 (2H, m), 6.89-6.97 (2H, m), 4.93 (1H, t), 4.53 (1H, s), 4.26 (2H, q), 3.61-3.70 (2H, m), 2.96-3.06 (2H, m), 1.29 (3H, t).

ESI+m/z 388 [M+H]

Example 28

Preparation of Intermediate 38 ethyl 4-(azetidin-3-yloxy)benzoate

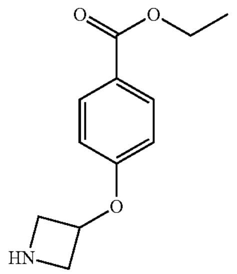 [SMILES: CCOC(=O)c1ccc(OC2CNC2)cc1]

To a solution of ethyl 4-((1-benzhydrylazetidin-3-yl)oxy) benzoate (2 g, 5.16 mmol) in 1,2-Dichloroethane (25 ml), ACE-Cl (0.845 ml, 7.74 mmol) was added and the reaction mixture was stirred at 70° C. for 2 h. After cooling to room temperature, ethanol (25 ml) was added and the reaction mixture was stirred at 70° C. for 36 h.

The reaction mixture was concentrated and loaded onto a SCX cartridges (10 g) and eluted with MeOH (3CV) and $NH_3$ 2.0 in MeOH (2CV). Ammonia fractions were evaporated and purified by chromatography (55 g NH—KP, CH to AcOEt) to give 640 mg of title compound (colourless oil).

ESI+m/z 222 [M+H]

Example 29

Preparation of Intermediate 39 ethyl 4-((1-isopropylazetidin-3-yl)oxy)benzoate

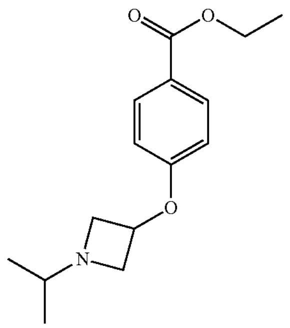 [SMILES: CCOC(=O)c1ccc(OC2CN(C(C)C)C2)cc1]

Acetone (0.637 ml, 8.68 mmol) was added to a solution of ethyl 4-(azetidin-3-yloxy)benzoate (640 mg, 2.89 mmol) in acetic acid (15 ml, 262 mmol). The reaction mixture was left stirring at room temperature for 10 min, then Sodium cyanotrihydridoborate (582 mg, 9.26 mmol) was added. The reaction mixture was left stirring at room temperature for 5 h. Solvents were evaporated to obtain a crude which was loaded on SNAP-$C_{18}$ gold (150 g) cartridges eluting with H2O—AcOH (0.1%)/$CH_3CN$—AcOH (0.1%). Yield 750 mg (light yellow oil).

ESI+m/z 264 [M+H]

Example 30

Preparation of Intermediate 40

4-((1-isopropylazetidin-3-yl)oxy)benzoic acid

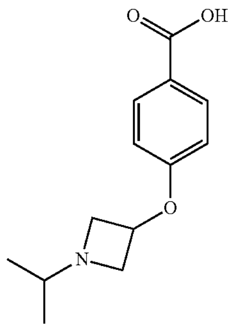 [SMILES: CC(C)N1CC(Oc2ccc(C(=O)O)cc2)C1]

Intermediate 39 (750 mg, 2.85 mmol) was dissolved in MeOH (15 ml), and sodium hydroxide 2 N (7.120 ml, 14.24 mmol) was added. The reaction was stirred for 16 h. The reaction was concentrated and the residue was acidified with acetic acid and then loaded onto a Phenomenex Strata SCX 20 g column primed with MeOH. The column was then eluted with MeOH and then with ammonia/MeOH. The fractions containing the desired product were pooled and evaporated to give title compound (380 mg; white solid).

$^1$H NMR (400 MHz, DMSO-$d_6$) δ ppm 7.79-7.95 (2H, m), 6.87-6.96 (2H, m), 4.81 (1H, t), 3.66-3.76 (2H, m), 2.90-3.02 (2H, m), 2.34 (1H, quin), 0.88 (6H, d). ESI+m/z 236 [M+H]

Example 31

Preparation of Intermediate 41

2-(6-chloro-1,3-dihydro-2H-pyrrolo[3,4-c]pyridin-2-yl)ethan-1-ol

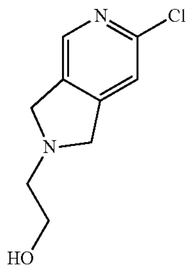 [SMILES: OCCN1Cc2cnc(Cl)cc2C1]

To 2-chloro-4,5-bis(chloromethyl)pyridine (500 mg, 2.375 mmol; prepared as in WO2006082001) in dry DMF (50 ml) was added N-ethyl-N-isopropylpropan-2-amine (1.655 ml, 9.50 mmol) followed by 2-aminoethanol (0.143 ml, 2.375 mmol) at once as a solid. The resulting mixture was then heated to 100° C. under nitrogen for 18 hours.

The reaction was then stripped of DMF and to the remaining residue was added DMSO (1 ml) and purified on a reverse phase column (50 g; water+0.1% AcOH only to ACN+0.1% AcOH in 12CV). Yield 330 mg of the title compound (light brown oil).

$^1$H NMR (400 MHz, DMSO-$d_6$) δ ppm 8.28 (1H, s), 7.44 (1H, s), 4.54 (1H, s), 3.91 (4H, s), 3.56 (2H, d, J=5.38 Hz), 2.70-2.81 (2H, m).

ESI+m/z 199 [M+H]

Example 32

Preparation of Intermediate 42

4-((dimethylamino)methyl)benzoyl chloride

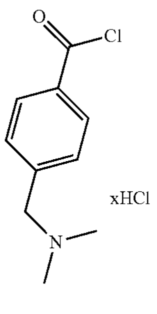

To 4-((dimethylamino)methyl)benzoic acid (0.730 g, 4.07 mmol) in dry DCM (30 ml) was added oxalyl dichloride (3.45 ml, 40.7 mmol) followed by N,N-dimethylformamide (0.016 ml, 0.204 mmol). The resulting mixture was stirred overnight at 45° C. and then evaporated. A small sample was treated with MeOH and analysed by mass.

ESI+m/z 194 [M+H](methyl ester).

Example 33

Preparation of Intermediate (VI) (Intermediates 43-63) of Scheme 1

General Procedure 5

To intermediate V (intermediates 10-14) (1 mmol) in Dioxane (10 ml), cesium carbonate (2 mmol), (9,9-dimethyl-9H-xanthene-4,5-diyl)bis(diphenylphosphine) (0.05 mmol) and Tris (dibenzylideneacetone)dipalladium (0) (0.0175 mmol) were added. The resulting mixture was then degassed by vacuum and the corresponding halo heterocycle $R_2X$ (1.05 mmol) was then added.

The reaction was heated at 90° C. for 3 hours, cooled and evaporated. To the residue was added AcOEt (25 mL) and DCM (25 mL), and the resulting mixture was then filtered through Celite. The filtrate was then evaporated to give a brown residue that was purified on silica gel column (25 g) eluting with DCM to DCM/AcOEt 1:1 to afford title intermediates.

General Procedure 6

To intermediate V (intermediates 10-14) (1 mmol) in dry DMSO (4 ml) the corresponding halo heterocycle $R_2X$ (1.05 mmol) was added, followed by N-ethyl-N-isopropylpropan-2-amine (2 mmol). The resulting mixture was stirred at 70° C. for 2-4 h.

The mixture was then added dropwise to water (50 mL) and extracted with DCM. The organic phases were washed with water, dried and evaporated under reduced pressure to give a residue that was purified on silica gel column (25 g) eluting with DCM to DCM/AcOEt 1:1 to afford title intermediates.

General Procedure 7 Carboxylic acids $R_2COOH$ (1 mmol) were dissolved in Toluene (5 ml). Thionyl chloride (80 mmol) was added and the reaction stirred under reflux for 2 h.

Solvents were evaporated and the residue was added to a solution of intermediate V (intermediates 10-14) (1 mmol) in pyridine (75 mmol). The reaction was stirred at RT for 13 h then taken up into a mixture of water/DCM (20/20 ml). Phases were separated and the aqueous layer was extracted with DCM (2x20 ml). The combined organic layers were evaporated and the crude was purified on silica gel column (25 g) eluting with cyclohexane/AcOEt 1:1 to AcOEt 100% to afford title intermediates.

Intermediates 43-63: Intermediate (VI) of scheme 1

| Intermediate | Structure | Analysis | Procedure | Yield (%) |
|---|---|---|---|---|
| 43 | 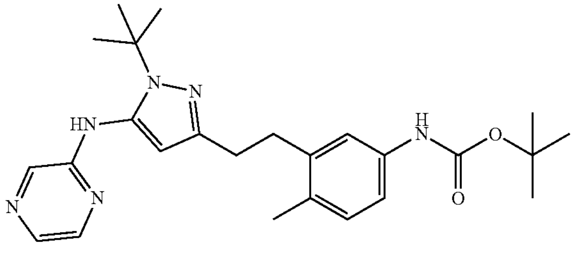 [SMILES: Cc1ccc(NC(=O)OC(C)(C)C)cc1CCc1cc(Nc2cnccn2)n(C(C)(C)C)n1] | $^1$H NMR (400 MHz, DMSO-$d_6$) δ ppm 9.10 (1 H, s), 8.62 (1 H, s), 8.05 (1 H, dd, J = 2.45, 1.47 Hz), 7.94 (1 H, d, J = 1.47 Hz), 7.90 (1 H, d, J = 2.93 Hz), 7.35 (1 H, s), 7.14 (1 H, dd, J = 8.31, 1.96 Hz), 6.99 (1 H, d, J = 7.83 Hz), 5.97(1 H, s), 2.75-2.85 (2 H, m), 2.63-2.74 (2 H, m), 2.19 (3 H, s), 1.52 (9 H, s), 1.46 (9 H, s). ESI + m/z 451 [M + H] | 5 | 81 |

-continued

Intermediates 43-63: Intermediate (VI) of scheme 1

| Intermediate | Structure | Analysis | Procedure | Yield (%) |
|---|---|---|---|---|
| 44 | 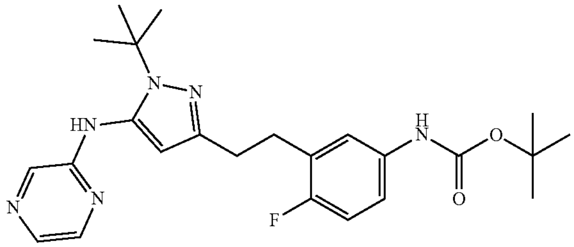 [SMILES: CC(C)(C)OC(=O)Nc1ccc(F)c(CCc2cc(Nc3cnccn3)n(C(C)(C)C)n2)c1] | $^1$H NMR (400 MHz, DMSO-$d_6$) δ ppm 9.25 (1 H, s), 8.61 (1 H, s), 8.05 (1 H, dd, J = 2.45, 1.47 Hz), 7.91 (2 H, dd, J = 9.78, 1.96 Hz), 7.46 (1 H, d, J = 4.89 Hz), 7.16-7.27 (1 H, m), 7.01 (1 H, t, J = 9.29 Hz), 5.97 (1 H, s), 2.81-2.89 (2 H, m), 2.71-2.78 (2 H, m), 1.51 (9 H, s), 1.46 (9 H, s). ESI + m/z 455 [M + H] | 5 | 70 |
| 45 | 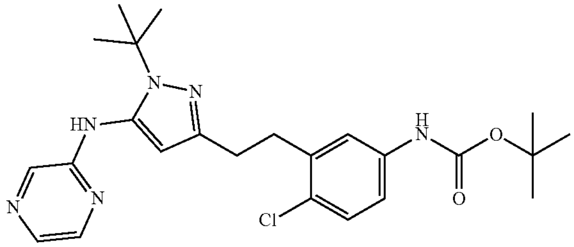 | $^1$H NMR (400 MHz, DMSO-$d_6$) δ ppm 9.38 (1 H, s), 8.61 (1 H, s), 8.02-8.08 (1 H, m), 7.87-7.96 (1 H, m), 7.54 (1 H, s), 7.27 (2 H, s), 5.97 (1 H, s), 2.88-2.97 (2 H, m), 2.69-2.80 (2 H, m), 1.49 (18 H, d, J = 19.56 Hz). ESI + m/z 473 [M + H] | 5 | 75 |
| 46 | 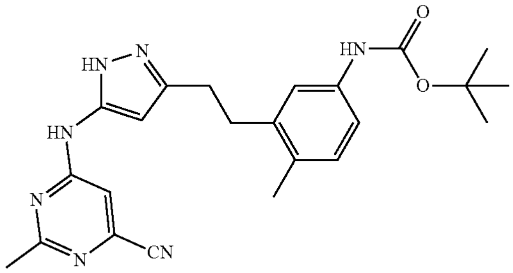 [SMILES: Cc1nc(C#N)cc(Nc2cc(CCc3cc(NC(=O)OC(C)(C)C)ccc3C)n[nH]2)n1] | $^1$H NMR (400 MHz, DMSO-$d_6$) δ ppm 12.28 (1 H, br. s), 10.41 (1 H, br. s), 9.14 (1 H, br. s), 7.31-7.39 (1 H, m), 7.11-7.20 (1 H, m), 6.98-7.05 (1 H, m), 2.74-2.88 (4 H, m), 2.47 (3 H, s), 2.21 (3 H, s), 1.46 (9 H, s). ESI + m/z 434 [M + H] | 6 | 95 |
| 47 | 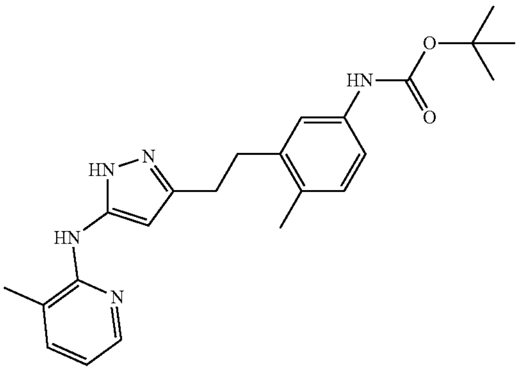 [SMILES: Cc1ccc(NC(=O)OC(C)(C)C)cc1CCc1cc(Nc2ncccc2C)[nH]n1] | $^1$H NMR (400 MHz, DMSO-$d_6$) δ ppm 11.92 (1 H, br. s.), 9.13 (1 H, br. s.), 7.95-8.05 (1 H, m), 7.35 (2 H, br. s.), 7.12-7.22 (1 H, m), 7.01 (1 H, d), 6.60-6.72 (1 H, m), 6.34 (1 H, br. s.), 2.70-2.89 (4 H, m), 2.17-2.26 (6 H, m), 1.47 (9 H, s). ESI + m/z 408 [M + H] | 5 | 93 |

-continued
Intermediates 43-63: Intermediate (VI) of scheme 1
| Inter-mediate | Structure | Analysis | Proce-dure | Yield (%) |
|---|---|---|---|---|
| 48 | 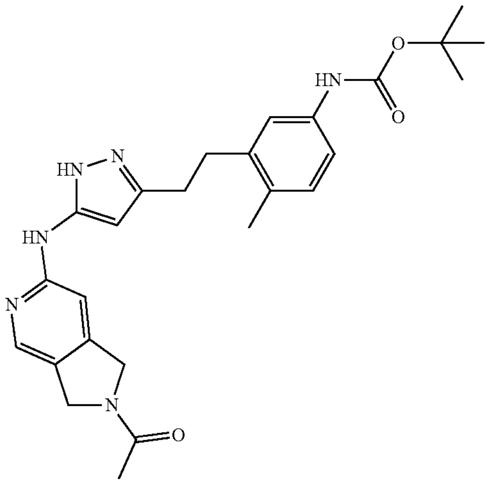 [SMILES: CC(=O)N1Cc2cnc(Nc3cc(CCc4cc(NC(=O)OC(C)(C)C)ccc4C)n[nH]3)cc2C1] | $^1$H NMR (400 MHz, DMSO-$d_6$) c ppm 11.85 (br. s., 1H), 9.23-8.99 (m, 2H), 8.10 (d, J = 4.4 Hz, 1H), 7.41-7.28 (m, 2H), 7.21-7.13 (m, 1H), 7.05-6.98 (m, 1H), 6.11-5.97 (m, 1H), 4.75 (d, J = 18.1 Hz, 2H), 4.54 (d, J = 10.8 Hz, 2H), 2.85-2.69 (m, 4H), 2.21 (s, 3H), 2.05 (d, J = 2.0 Hz, 3H), 1.47 (s, 9H). ESI + m/z 477 [M + H] | 5 | 76 |
| 49 | 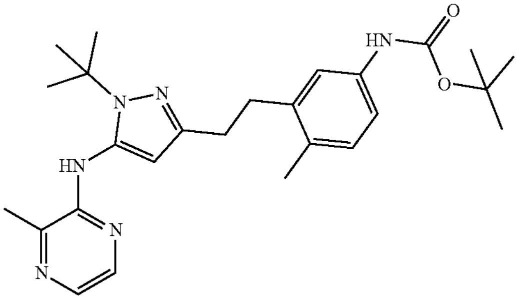 [SMILES: Cc1ccc(NC(=O)OC(C)(C)C)cc1CCc1cc(Nc2nccnc2C)n(C(C)(C)C)n1] | ESI + m/z 464 [M + H] | 5 | 60 |
| 50 | 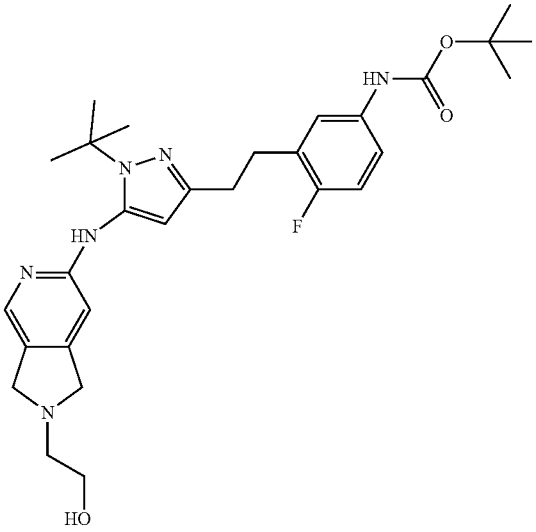 [SMILES: CC(C)(C)OC(=O)Nc1ccc(F)c(CCc2cc(Nc3cc4c(cn3)CN(CCO)C4)n(C(C)(C)C)n2)c1] | $^1$H NMR (400 MHz, DMSO-$d_6$) δ ppm 9.26 (1 H, br. s.), 7.95-8.02 (1 H, m), 7.89 (1 H, s), 7.46 (1 H, d, J = 4.89 Hz), 7.17-7.27 (1 H, m), 7.01 (1 H, t, J = 9.29 Hz), 6.25 (1 H, s), 5.86 (1 H, s), 4.48 (1 H, t, J = 5.38 Hz), 3.75 (4 H, d, J = 5.38 Hz), 3.50-3.58 (2 H, m), 2.81-2.89 (2 H, m), 2.69-2.77 (4 H, m), 1.41-1.57 (18 H, m). ESI + m/z 539 [M + H] | 5 | 38 |

-continued

| Intermediates 43-63: Intermediate (VI) of scheme 1 | | | | |
|---|---|---|---|---|
| Intermediate | Structure | Analysis | Procedure | Yield (%) |
| 51 | 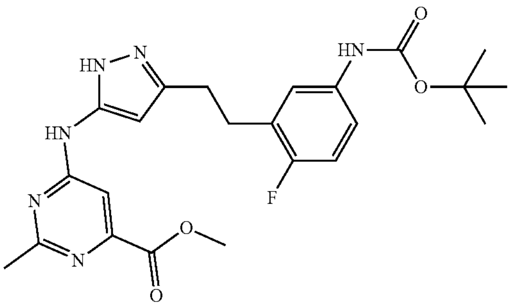 [SMILES: COC(=O)c1cc(Nc2cc(CCc3cc(NC(=O)OC(C)(C)C)ccc3F)n[nH]2)nc(C)n1] | $^1$H NMR (400 MHz, DMSO-$d_6$) δ ppm 12.18 (1 H, br. s), 10.08 (1 H, br. s), 9.29 (1 H, br. s), 7.40-7.54 (1 H, m), 7.20-7.32 (1 H, m), 7.05 (1 H, t), 3.86 (3 H, s), 2.76-2.96 (4 H, m), 2.48 (3 H, s), 1.46 (9 H, s). ESI + m/z 471 [M + H] | 6 | 52 |
| 52 | 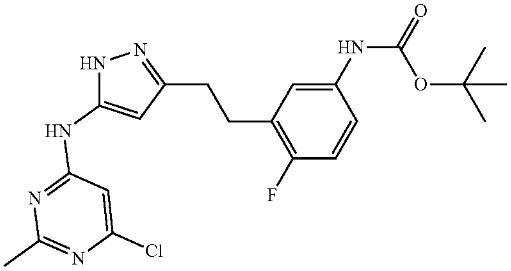 | $^1$H NMR (400 MHz, DMSO-$d_6$) δ ppm 12.20-12.31 (1 H, m), 10.39 (1 H, s), 9.28 (1 H, s), 7.39-7.51 (1 H, m), 7.20-7.30 (1 H, m), 7.04 (1 H, t, J = 9.29 Hz), 2.88 (4 H, br. s.), 2.46 (3 H, s), 1.43-1.49 (9 H, m). ESI + m/z 438 [M + H] | 6 | 55 |
| 53 | 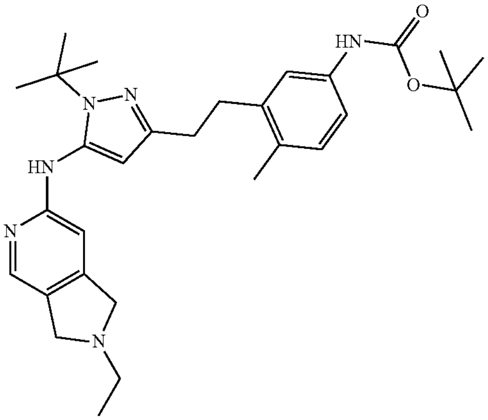 [SMILES: CCN1Cc2cnc(Nc3cc(CCc4cc(NC(=O)OC(C)(C)C)ccc4C)nn3C(C)(C)C)cc2C1] | $^1$H NMR (400 MHz, DMSO-$d_6$) δ ppm 9.10 (s, 1H), 7.97 (s, 1 H), 7.90 (s, 1H), 7.34 (s, 1H), 7.14 (dd, J = 1.7, 8.1 Hz, 1H), 6.99 (d, J = 8.3 Hz, 1H), 6.27 (s, 1H), 5.85 (s, 1H), 3.70 (s, 4H), 2.85-2.76 (m, 2H), 2.72-2.61 (m, 4H), 2.18 (s, 3H), 1.54-1.44 (m, 18H), 1.08 (t, J = 7.1 Hz, 3H). ESI + m/z 519 [M + H] | 5 | 69 |
| 54 | 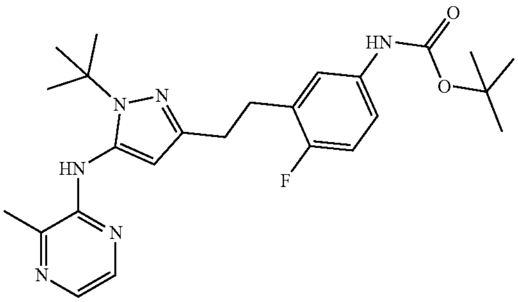 [SMILES: Cc1nccnc1Nc1cc(CCc2cc(NC(=O)OC(C)(C)C)ccc2F)nn1C(C)(C)C] | $^1$H NMR (400 MHz, DMSO-$d_6$) δ ppm 9.26 (1 H, br. s.), 7.98 (1 H, s), 7.87 (1 H, d, J = 2.93 Hz), 7.78 (1 H, d, J = 2.93 Hz), 7.48 (1 H, d, J = 5.38 Hz), 7.24 (1 H, dd, J = 8.07, 3.67 Hz), 7.02 (1 H, t, J = 9.29 Hz), 5.91 (1 H, s), 2.85 (2 H, d, J = 8.80 Hz), 2.73-2.79 (2 H, m), 2.72-2.79 (2 H, m), 2.44 (3 H, s), 1.48 (18 H, d, J = 6.36 Hz). ESI + m/z 469 [M + H] | 5 | 74 |

-continued

| Intermediates 43-63: Intermediate (VI) of scheme 1 | | | | |
|---|---|---|---|---|
| Inter-mediate | Structure | Analysis | Proce-dure | Yield (%) |
| 55 | 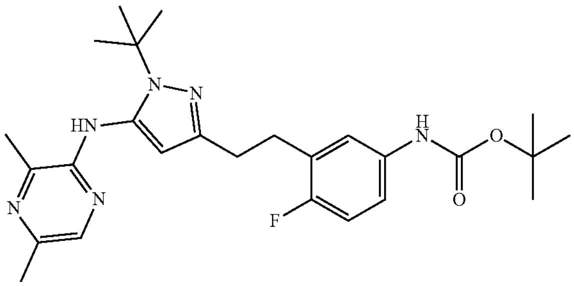 [SMILES: Cc1cnc(Nc2cc(CCc3cc(NC(=O)OC(C)(C)C)ccc3F)nn2C(C)(C)C)c(C)n1] | $^1$H NMR (400 MHz, DMSO-$d_6$) δ ppm 9.20-9.31 (1 H, m), 7.75 (2 H, d, J = 7.82 Hz), 7.48 (2 H, d, J = 5.38 Hz), 7.44-7.53 (2 H, m), 7.22 (1 H, d, J = 3.91 Hz), 6.97-7.07 (1 H, m), 5.87 (1 H, s), 2.84 (2 H, d, J = 8.31 Hz), 2.75 (2H, d, J = 8.31 Hz), 2.40 (3 H, s), 2.27 (3 H, s), 1.48 (18 H, d, J = 5.38 Hz). ESI + m/z 483 [M + H] | 5 | 93 |
| 56 | 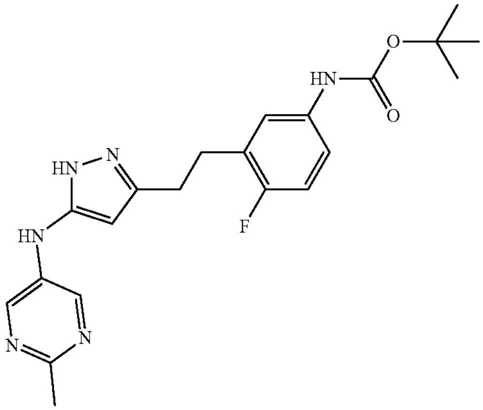 [SMILES: Cc1ncc(Nc2cc(CCc3cc(NC(=O)OC(C)(C)C)ccc3F)n[nH]2)cn1] | $^1$H NMR (400 MHz, DMSO-$d_6$) δ ppm 11.98-11.76 (m, 1H), 9.43-9.20 (m, 1H), 8.87-8.66 (m, 2H), 8.63-8.53 (m, 1H), 7.52-7.36 (m, 1H), 7.30-7.18 (m, 1H), 7.12-6.96 (m, 1H), 5.69-5.54 (m, 1H), 2.94-2.75 (m, 4H), 2.48 (s, 3H), 1.46 (s, 9H). ESI + m/z 413 [M + H] | 5 | 76 |
| 57 | 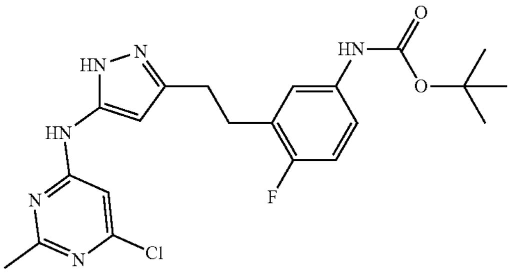 [SMILES: Cc1nc(Cl)cc(Nc2cc(CCc3cc(NC(=O)OC(C)(C)C)ccc3F)n[nH]2)n1] | $^1$H NMR (400 MHz, DMSO-$d_6$) δ ppm 12.18-12.30 (1 H, m), 10.41 (1 H, s), 9.41 (1 H, s), 7.36-7.50 (1 H, m), 7.22-7.30 (1 H, m), 7.10 (1 H, t, J = 9.29 Hz), 2.91 (4 H, br. s.), 2.42 (3 H, s), 1.40-1.51 (9 H, m). ESI + m/z 447 [M + H] | 6 | 63 |
| 58 | 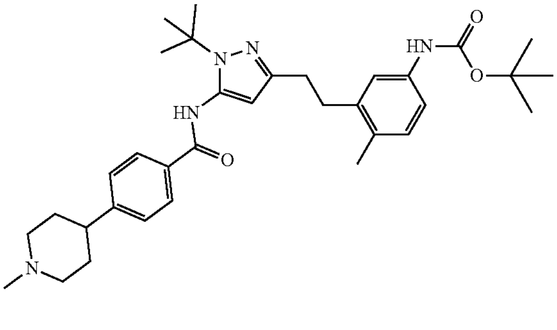 [SMILES: Cc1ccc(NC(=O)OC(C)(C)C)cc1CCc1cc(NC(=O)c2ccc(C3CCN(C)CC3)cc2)n(C(C)(C)C)n1] | $^1$H NMR (400 MHz, DMSO-$d_6$) δ ppm 9.88 (s, 1H), 9.11 (s, 1H), 7.89 (d, J = 8.3 Hz, 2H), 7.41 (d, J = 8.3 Hz, 2H), 7.36 (s, 1H), 7.19-7.11 (m, 1H), 7.00 (d, J = 8.3 Hz, 1H), 6.02 (s, 1H), 2.92-2.84 (m, 2H), 2.80 (d, J = 9.8 Hz, 2H), 2.73-2.68 (m, 2H), 2.23-2.18 (m, 6H), 2.03-1.93 (m, 2H), 1.79-1.66 (m, 4H), 1.54 (s, 9H), 1.47 (s, 9H). ESI + m/z 575 [M + H] | 7 | 48 |

-continued
Intermediates 43-63: Intermediate (VI) of scheme 1
| Inter-mediate | Structure | Analysis | Proce-dure | Yield (%) |
|---|---|---|---|---|
| 59 | 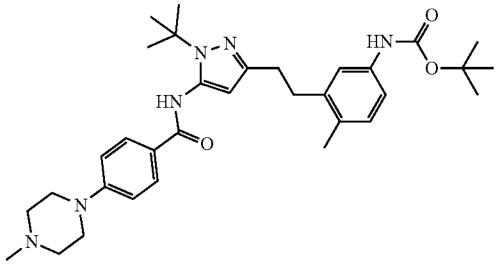 [SMILES: Cc1ccc(NC(=O)OC(C)(C)C)cc1CCc1cc(NC(=O)c2ccc(N3CCN(C)CC3)cc2)n(C(C)(C)C)n1] | $^1$H NMR (400 MHz, DMSO-$d_6$) δ ppm 9.60-9.64 (1 H, m), 9.11 (1 H, s), 7.84 (2 H, d), 7.32-7.39 (1 H, m), 7.12-7.20 (1 H, m), 6.96-7.04 (3 H, m), 5.99 (1 H, s), 2.75-2.85 (2 H, m), 2.64-2.74 (2 H, m), 2.45 (4 H, m), 2.23 (3 H, s), 2.21 (3 H, s), 1.52 (9 H, s), 1.47 (9 H, s).<br>ESI + m/z 575 [M + H] | 7 | 70 |
| 60 | 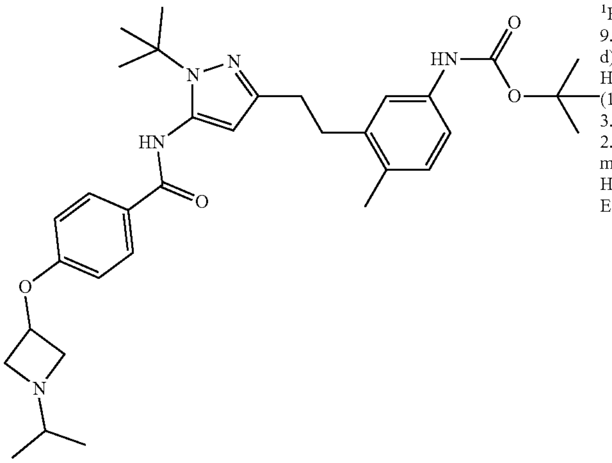 | $^1$H NMR (400 MHz, DMSO-$d_6$) δ ppm 9.80 (1 H, s), 9.11 (1 H, s), 7.92 (2 H, d), 7.31-7.39 (1 H, m), 7.12-7.19 (1 H, m), 6.93-7.03 (3 H, m), 5.98-6.03 (1 H, m), 4.77-4.87 (1 H, m), 3.67-3.76 (2 H, m), 2.91-2.98 (2 H, m), 2.75-2.84 (2 H, m), 2.64-2.74 (2 H, m), 2.21 (3 H, s), 1.53 (9 H, s), 1.47 (9 H, s), 0.88 (6 H, d).<br>ESI + m/z 591 [M + H] | 7 | 45 |
| 61 | 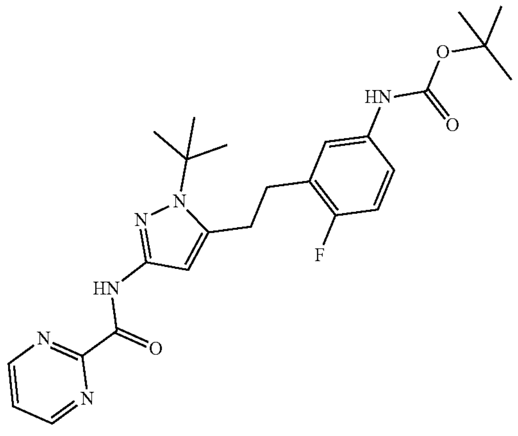 [SMILES: CC(C)(C)OC(=O)Nc1ccc(F)c(CCc2cc(NC(=O)c3ncccn3)nn2C(C)(C)C)c1] | $^1$H NMR (400 MHz, methanol-$d_4$) δ ppm 9.03 (2 H, d, J = 4.89 Hz), 7.73 (1 H, t, J = 4.89 Hz), 7.25 (2 H, d, J = 5.38 Hz), 6.95 (1 H, d, J = 9.29 Hz), 6.27 (1 H, s), 2.88-2.99 (5 H, m), 1.66 (9 H, s), 1.52 (10 H, s).<br>ESI + m/z 483 [M + H] | 7 | 40 |

-continued

| Intermediates 43-63: Intermediate (VI) of scheme 1 | | | | |
|---|---|---|---|---|
| Inter-mediate | Structure | Analysis | Proce-dure | Yield (%) |
| 62 | 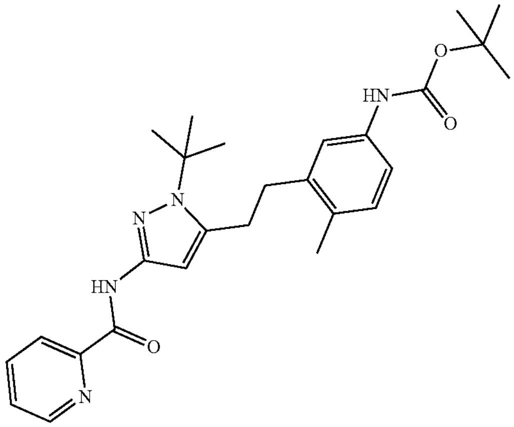 [SMILES: Cc1ccc(NC(=O)OC(C)(C)C)cc1CCc1cc(NC(=O)c2ccccn2)nn1C(C)(C)C] | ESI + m/z 478 [M + H] | 7 | 52 |
| 63 | 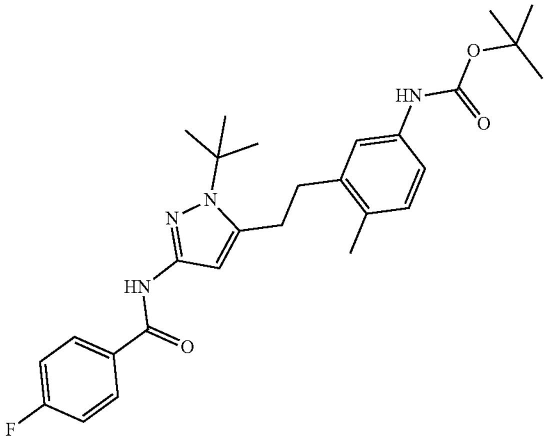 [SMILES: Cc1ccc(NC(=O)OC(C)(C)C)cc1CCc1cc(NC(=O)c2ccc(F)cc2)nn1C(C)(C)C] | ESI + m/z 495 [M + H] | 7 | 68 |

Example 34

Preparation of Intermediate (VII) (Intermediates 64-84) of Scheme 1

General Procedure 8

To intermediates 43-63 (1 mmol) in DCM (10 ml) was slowly added TFA (ml). After 3 hours at RT, the reaction was stripped of volatiles under vacuum, DCM (40 ml) and saturated aq. sodium hydrogen carbonate solution (75 ml) were added; the organic phase was separated, dried over anhydrous sodium sulphate and evaporated to give title intermediates.

TABLE 6

| Intermediates 64-84: Intermediate (VII) of scheme 1 | | | |
|---|---|---|---|
| Intermediates | Structure | Analysis | Yields (%) |
| 64 | 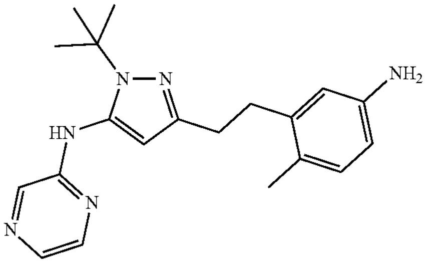 [SMILES: Cc1ccc(N)cc1CCc1cc(Nc2cnccn2)n(C(C)(C)C)n1] | $^1$H NMR (400 MHz, DMSO-d$_6$) δ ppm 8.62 (1 H, s), 8.05 (1 H, dd), 7.93 (2 H, dd), 6.77 (1 H, d), 6.46 (1 H, d), 6.32 (1 H, dd), 5.97 (1 H, s), 4.68 (2 H, s), 2.59-2.77 (4 H, m), 2.10 (3 H, s), 1.52 (9 H, s). ESI + m/z 351 [M + H] | 98 |
| 65 | 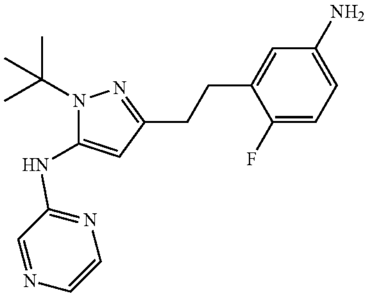 [SMILES: CC(C)(C)n1nc(CCc2cc(N)ccc2F)cc1Nc1cnccn1] | $^1$H NMR (400 MHz, DMSO-d$_6$) δ ppm 8.61 (1 H, s), 8.06 (1 H, s), 7.92 (2 H, d), 6.78 (1 H, d), 6.45 -6.57 (1 H, m), 6.32-6.43 (1 H, m), 5.97 (1 H, s), 4.73-4.87 (2 H, m), 2.74 (4 H, d), 1.51 (9 H, s). ESI + m/z 354 [M + H] | 86 |
| 66 | 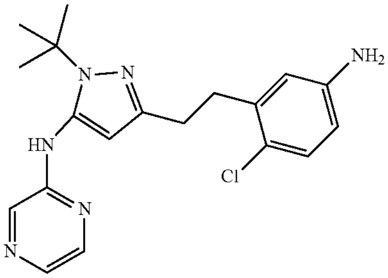 [SMILES: CC(C)(C)n1nc(CCc2cc(N)ccc2Cl)cc1Nc1cnccn1] | $^1$H NMR (400 MHz, DMSO-d$_6$) δ ppm 8.62 (1 H, s), 8.05 (1 H, d, J = 1.47 Hz), 7.87-7.98 (2 H, m), 7.00 (1 H, d, J = 8.31 Hz), 6.57 (1 H, d, J = 2.93 Hz), 6.42 (1 H, dd, J = 8.56, 2.69 Hz), 5.98 (1 H, s), 5.11 (2 H, br. s.), 2.81 (2 H, s), 2.74 (2 H, s), 1.52 (9 H, s). ESI + m/z 371 [M + H] | 93 |
| 67 | 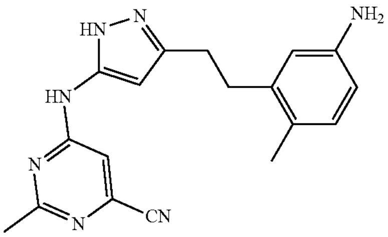 | $^1$H NMR (400 MHz, DMSO-d$_6$) δ ppm 12.28 (1 H, br. s.), 10.40 (1 H, br. s.), 6.89 (1 H, t, J = 9.05 Hz), 6.50-6.65 (2H, m), 6.03 (2 H, br. s.), 2.84 (4 H, s), 2.47 (3 H, s). ESI + m/z 338 [M + H] | 75 |

Example 34

Preparation of Intermediate (VII) (Intermediates 64-84) of Scheme 1

General Procedure 8

To intermediates 43-63 (1 mmol) in DCM (10 ml) was slowly added TFA (ml). After 3 hours at RT, the reaction was stripped of volatiles under vacuum, DCM (40 ml) and saturated aq. sodium hydrogen carbonate solution (75 ml) were added; the organic phase was separated, dried over anhydrous sodium sulphate and evaporated to give title intermediates.

TABLE 6

Intermediates 64-84: Intermediate (VII) of scheme 1

| Intermediates | Structure | Analysis | Yields (%) |
|---|---|---|---|
| 64 | 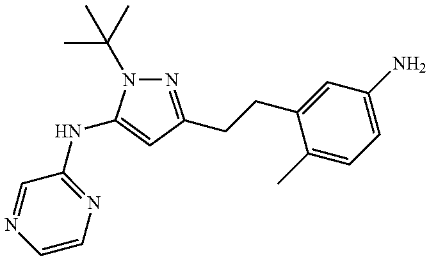 [SMILES: Cc1ccc(N)cc1CCc1cc(Nc2cnccn2)n(C(C)(C)C)n1] | $^1H$ NMR (400 MHz, DMSO-$d_6$) δ ppm 8.62 (1 H, s), 8.05 (1 H, dd), 7.93 (2 H, dd), 6.77 (1 H, d), 6.46 (1 H, d), 6.32 (1 H, dd), 5.97 (1 H, s), 4.68 (2 H, s), 2.59-2.77 (4 H, m), 2.10 (3 H, s), 1.52 (9 H, s). ESI + m/z 351 [M + H] | 98 |
| 65 | 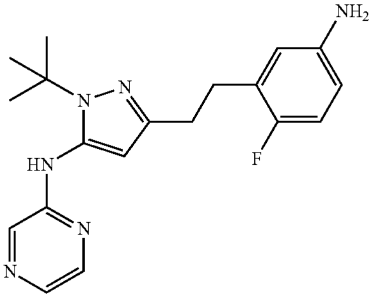 [SMILES: CC(C)(C)n1nc(CCc2cc(N)ccc2F)cc1Nc1cnccn1] | $^1H$ NMR (400 MHz, DMSO-$d_6$) δ ppm 8.61 (1 H, s), 8.06 (1 H, s), 7.92 (2 H, d), 6.78 (1 H, d), 6.45 -6.57 (1 H, m), 6.32-6.43 (1 H, m), 5.97 (1 H, s), 4.73-4.87 (2 H, m), 2.74 (4 H, d), 1.51 (9 H, s). ESI + m/z 354 [M + H] | 86 |
| 66 | 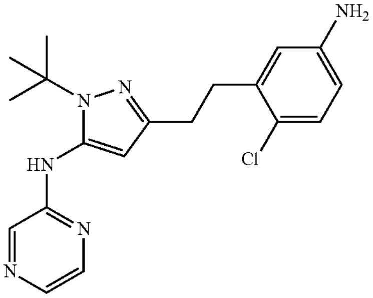 | $^1H$ NMR (400 MHz, DMSO-$d_6$) δ ppm 8.62 (1 H, s), 8.05 (1 H, d, J = 1.47 Hz), 7.87-7.98 (2 H, m), 7.00 (1 H, d, J = 8.31 Hz), 6.57 (1 H, d, J = 2.93 Hz), 6.42 (1 H, dd, J = 8.56, 2.69 Hz), 5.98 (1 H, s), 5.11 (2 H, br. s.), 2.81 (2 H, s), 2.74 (2 H, s), 1.52 (9 H, s). ESI + m/z 371 [M + H] | 93 |
| 67 | 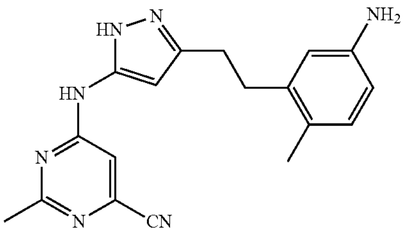 | $^1H$ NMR (400 MHz, DMSO-$d_6$) δ ppm 12.28 (1 H, br. s.), 10.40 (1 H, br. s.), 6.89 (1 H, t, J = 9.05 Hz), 6.50-6.65 (2H, m), 6.03 (2 H, br. s.), 2.84 (4 H, s), 2.47 (3 H, s). ESI + m/z 338 [M + H] | 75 |

TABLE 6-continued
| Intermediates 64-84: Intermediate (VII) of scheme 1 | | | |
|---|---|---|---|
| Intermediates | Structure | Analysis | Yields (%) |
| 68 | 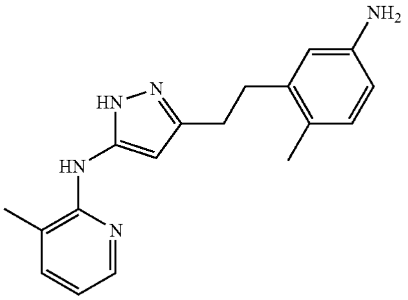 [SMILES: Cc1ccc(N)cc1CCc1cc(Nc2ncccc2C)[nH]n1] | $^1$H NMR (400 MHz, DMSO-$d_6$) δ ppm 11.76-12.25 (1 H, m), 7.71-8.19 (2 H, m), 7.22-7.53 (1 H, m), 6.58-6.86 (2 H, m), 6.46 (3 H, m), 4.72 (2 H, br. s.), 2.73 (4 H, br. s.), 2.21 (3 H, s), 2.13 (3 H, s). ESI + m/z 308 [M + H] | 91 |
| 69 | 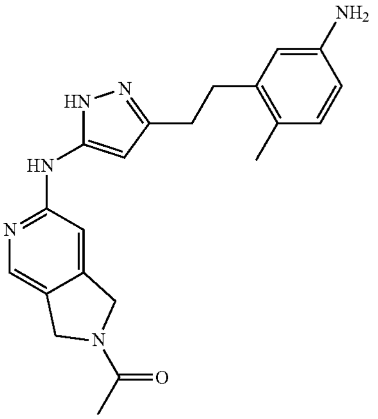 [SMILES: CC(=O)N1Cc2cnc(Nc3cc(CCc4cc(N)ccc4C)n[nH]3)cc2C1] | $^1$H NMR (400MHz, DMSO-$d_6$) δ ppm 11.83 (br. s., 1H), 9.06 (br. s., 1H), 8.10 (d, J = 3.9 Hz, 1H), 7.33 (br. s. 1H), 6.79 (d, J = 7.8 Hz, 1H), 6.44 (d, J = 2.4 Hz, 1H), 6.34 (dd, J = 2.2, 8.1 Hz, 1H), 6.06 (br. s., 1H), 4.76 (d, J = 17.6 Hz, 4H), 4.54 (d, J = 10.8 Hz, 2H), 2.73 (s, 4H), 2.12 (s, 3H), 2.06 (d, J = 2.9 Hz, 3H). ESI + m/z 377 [M + H] | 94 |
| 70 | 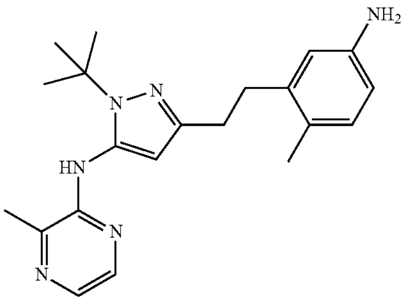 [SMILES: Cc1ccc(N)cc1CCc1cc(Nc2nccnc2C)n(C(C)(C)C)n1] | $^1$H NMR (400 MHz, DMSO-d6) δ ppm 7.78-7.93 (1 H, m), 7.46 (1 H, s), 7.34-7.41 (1 H, m), 6.75-6.82 (1 H, m), 6.58-6.65 (1 H, m), 6.48 (1 H, d), 6.28-6.36 (1 H, m), 5.88 (1 H, s), 4.69 (2 H, s), 2.63-2.77 (4 H, m), 2.19 (3 H, s), 2.12 (3 H, s), 1.50 (8 H, s). ESI + m/z 364 [M + H] | 60 |
| 71 | 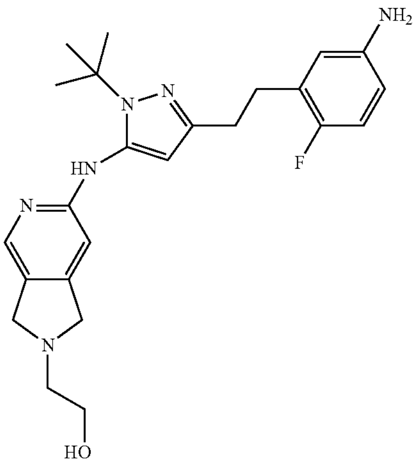 [SMILES: CC(C)(C)n1nc(CCc2cc(N)ccc2F)cc1Nc1cc2c(cn1)CN(CCO)C2] | ESI + m/z 439 [M + H] | 90 |

TABLE 6-continued

| Intermediates 64-84: Intermediate (VII) of scheme 1 | | | |
|---|---|---|---|
| Intermediates | Structure | Analysis | Yields (%) |
| 72 | 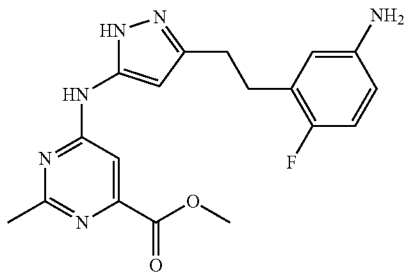 [SMILES: COC(=O)c1cc(Nc2cc(CCc3cc(N)ccc3F)n[nH]2)nc(C)n1] | $^1H$ NMR (400 MHz, DMSO-$d_6$) δ ppm 12.15 (1 H, br. s), 10.10 (1 H, br. s), 6.80 (1 H, t), 6.47 (1 H, dd), 6.36-6.43 (1 H, m), 4.84 (2 H, s), 3.86 (3 H, s), 2.81 (4 H, m), 2.48 (3 H,s). ESI + m/z 371 [M + H] | 98 |
| 73 | 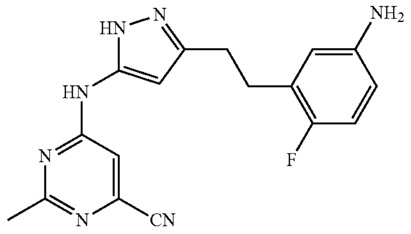 | $^1H$ NMR (400 MHz, DMSO-$d_6$) δ ppm 12.28 (1 H, br. s.), 10.40 (1 H, br. s.), 6.89 (1 H, t, J = 9.05 Hz), 6.50-6.65 (2H, m), 6.03 (2 H, br. s.), 2.84 (4 H, s), 2.47 (3 H, s). ESI + m/z 338 [M + H] | 75 |
| 74 | 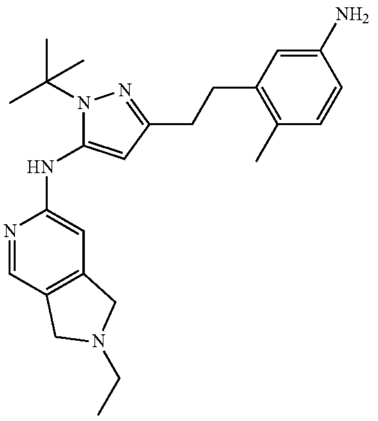 [SMILES: CCN1Cc2cnc(Nc3cc(CCc4cc(N)ccc4C)nn3C(C)(C)C)cc2C1] | $^1H$ NMR (400 MHz, DMSO-$d_6$) δ ppm 7.99 (s, 1H), 7.90 (s, 1H), 6.77 (d, J = 7.8 Hz, 1H), 6.45 (d, J = 2.4 Hz, 1H), 6.35-6.29 (m, 2H), 5.86 (s, 1H), 4.85-4.57 (m, 2H), 3.72 (s, 4H), 2.75-2.60 (m, 6H), 2.09 (s, 3H), 1.51 (s, 9H), 1.08 (t, J = 7.1 Hz, 3H). ESI + m/z 419 [M + H] | 94 |
| 75 | 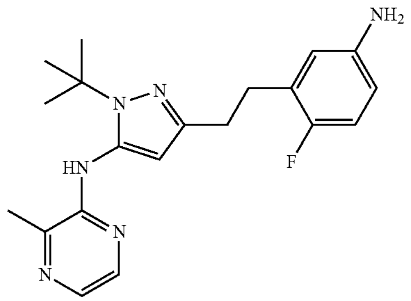 [SMILES: Cc1nccnc1Nc1cc(CCc2cc(N)ccc2F)nn1C(C)(C)C] | $^1H$ NMR (400 MHz, DMSO-$d_6$) δ ppm 7.99 (1 H, s), 7.87 (1 H, d, J = 2.45 Hz), 7.78 (1 H, d, J = 2.45 Hz), 6.78 (1 H, dd, J = 9.78, 8.80 Hz), 6.51 (1 H, dd, J = 6.60, 2.69 Hz), 6.34-6.41 (1 H, m), 5.90 (1 H, s), 4.81 (2 H, s), 2.68-2.80 (4 H, m), 2.44 (3 H, s), 1.49 (9 H, s). ESI + m/z 368 [M + H] | 98 |

TABLE 6-continued

| Intermediates 64-84: Intermediate (VII) of scheme 1 | | | |
|---|---|---|---|
| Intermediates | Structure | Analysis | Yields (%) |
| 76 | 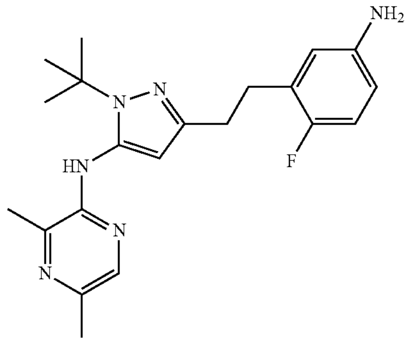 [SMILES: Cc1cnc(Nc2cc(CCc3cc(N)ccc3F)nn2C(C)(C)C)c(C)n1] | $^1$H NMR (400 MHz, DMSO-$d_6$) δ ppm 7.75 (2 H, d, J = 9.78 Hz), 6.78 (1 H, dd, J = 9.78, 8.80 Hz), 6.51 (1 H, dd, J = 6.60, 2.69 Hz), 6.34-6.41 (1 H, m), 5.87 (1 H, s), 4.80 (2 H, s), 2.69-2.80 (4 H, m), 2.41 (3 H, s), 2.27 (3H, s), 1.49 (9H, s). ESI + m/z 383 [M + H] | 90 |
| 77 | 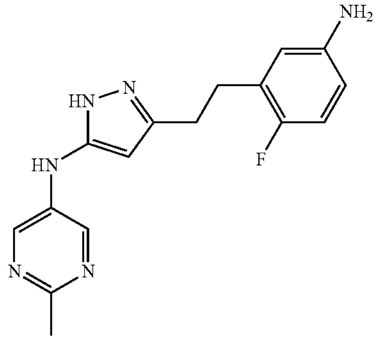 [SMILES: Cc1ncc(Nc2cc(CCc3cc(N)ccc3F)n[nH]2)cn1] | $^1$H NMR (400 MHz, DMSO-$d_6$) δ ppm 11.88 (br. s., 1H), 8.74 (s, 2H), 8.65-8.51 (m, 1H), 6.88-6.70 (m, 1H), 6.51-6.43 (m, 1H), 6.43-6.30 (m, 1H), 5.68-5.54 (m, 1H), 4.90 (br. s, 2H), 2.79 (s, 4H), 2.48 (s, 3H). ESI + m/z 313 [M + H] | 90 |
| 78 | 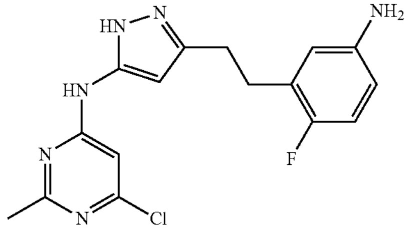 [SMILES: Cc1nc(Cl)cc(Nc2cc(CCc3cc(N)ccc3F)n[nH]2)n1] | $^1$H NMR (400 MHz, DMSO-$d_6$) δ ppm 12.13 (1 H, br. s.), 10.55 (1 H, br. s.), 6.96 (1 H, t, J = 9.01 Hz), 6.40-6.62 (2H, m), 5.98 (2 H, br. s.), 2.92 (4 H, s), 2.41 (3 H, s). ESI + m/z 347 [M + H] | 88 |
| 79 | 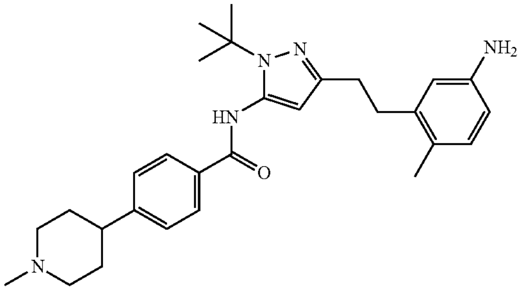 [SMILES: Cc1ccc(N)cc1CCc1cc(NC(=O)c2ccc(C3CCN(C)CC3)cc2)n(C(C)(C)C)n1] | $^1$H NMR (400 MHz, DMSO-$d_6$) δ ppm 9.91-9.83 (m, 1H), 7.89 (d, J = 7.8 Hz, 2H), 7.41 (d, J = 7.8 Hz, 2H), 6.78 (d, J = 7.8 Hz, 1H), 6.47 (d, J = 2.0 Hz, 1 H), 6.32 (dd, J = 2.4, 8.3 Hz, 1H), 6.01 (s, 1H), 4.63 (br. s, 2H), 2.94-2.81 (m, 2H), 2.77-2.64 (m, 4H), 2.22 (s, 3H), 2.14-2.07 (m, 3H), 2.00 (br. s., 2H), 1.74 (s, 4H), 1.58.-1.49 (m, 9H). ESI + m/z 474 [M + H] | 93 |
| 80 | 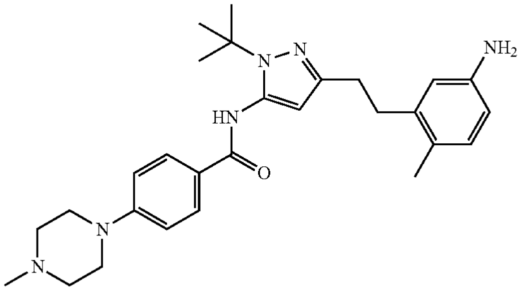 [SMILES: Cc1ccc(N)cc1CCc1cc(NC(=O)c2ccc(N3CCN(C)CC3)cc2)n(C(C)(C)C)n1] | ESI + m/z 475 [M + H] | 98 |

TABLE 6-continued
| Intermediates 64-84: Intermediate (VII) of scheme 1 | | | |
|---|---|---|---|
| Intermediates | Structure | Analysis | Yields (%) |
| 81 | 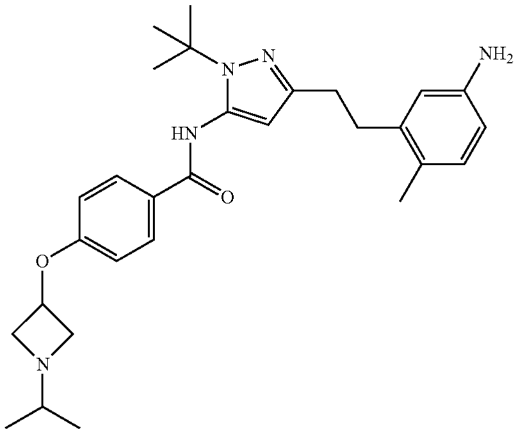 [SMILES: Cc1ccc(N)cc1CCc1cc(NC(=O)c2ccc(OC3CN(C(C)C)C3)cc2)n(C(C)(C)C)n1] | $^1$H NMR (400 MHz, DMSO-$d_6$) δ ppm 9.80 (1 H, s), 8.49 (1 H, d), 7.82-8.02 (2 H, m), 7.22-7.32 (1 H, m), 6.88-7.03 (2 H, m), 6.74-6.82 (1 H, m), 6.44-6.52 (1 H, m), 6.24-6.40 (1 H, m), 5.96-6.03 (1 H, m), 4.78-4.88 (1 H, m), 4.63-4.75 (2 H, m), 3.64-3.84 (2 H, m), 2.88-3.02 (2 H, m), 2.61-2.78 (4 H, m), 2.27-2.40 (1 H, m), 2.12 (3 H, s), 1.53 (9 H, s), 0.81-0.96 (6 H, m). ESI + m/z 490 [M + H] | 48 |
| 82 | 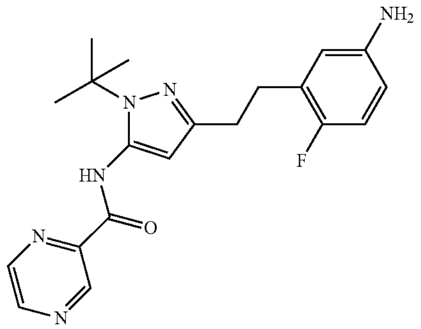 | $^1$H NMR (400 MHz, methanol-$d_4$) δ ppm 9.06 (2 H, d, J = 4.89 Hz), 7.76 (1 H, s), 7.24-7.31 (2 H, m), 7.18-7.23 (1 H, m), 6.16 (1 H, s), 2.94-3.12 (5 H, m), 1.67 (9 H, s). ESI + m/z 456 [M + H] | 94 |
| 83 | 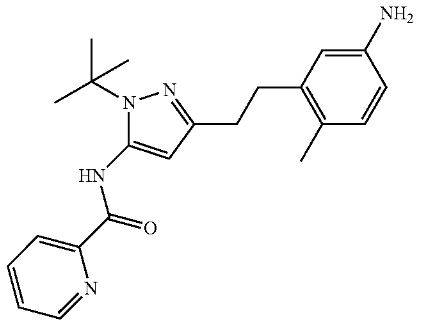 [SMILES: Cc1ccc(N)cc1CCc1cc(NC(=O)c2ccccn2)n(C(C)(C)C)n1] | ESI + m/z 378 [M + H] | 90 |
| 84 | 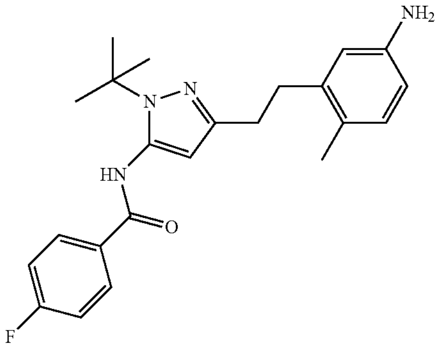 [SMILES: Cc1ccc(N)cc1CCc1cc(NC(=O)c2ccc(F)cc2)n(C(C)(C)C)n1] | ESI + m/z 395 [M + H] | 92 |

Example 35

Preparation of Intermediate (VIII) (Intermediates 85-111) of Scheme 1

General Procedure 9

Acid chlorides (1.5 mmol) were added to a solution of intermediate (VII) (intermediates 65; 66; 67; 71; 72; 75; 76; 77; 80; 81; 82; 83; 84) (1 mmol) in pyridine (24 mmol) and the resulting mixture was stirred at RT for 1-4 h.

Solvent was evaporated and the residue was purified by reverse phase column (50 g) eluting with $H_2O$—AcOH (0.1%) to $CH_3CN$—AcOH (0.1%) in gradient. Fractions containing the desired product were loaded on Strata-XL-C 100 μm SPE (2 g) cartridges eluting with $H_2O$/MeOH and $NH_3$ 1M in MeOH. Ammonia fractions were evaporated to give title intermediates.

General Procedure 10

Carboxylic acids (1.5 mmol), HOBT (1.5 mmol), EDC (1.5 mmol) and DIPEA (3 mmol) were dissolved in DMF (10 ml) under nitrogen. After 15 minutes of activation, this mixture was added to a solution of intermediate (VII) (intermediates 65; 66; 67; 71; 72; 75; 76; 77; 80; 81; 82; 83; 84) (1 mmol) in DMF (7.5 ml). The resulting mixture was stirred 5-7 h at RT. The solvent was evaporated and the residue was purified by reverse phase chromatography (50 g), eluting with $H_2O$—AcOH (0.1%) to $CH_3CN$—AcOH (0.1%) in gradient.

Fractions containing the desired product were loaded on Strata-XL-C 100 μm SPE (2 g) cartridges eluting with $H_2O$/MeOH and $NH_3$ 1M in MeOH. Ammonia fractions were evaporated to give title intermediates.

General Procedure 11

To a solution of intermediate (VII) (intermediates 65; 66; 67; 71; 72; 75; 76; 77; 80; 81; 82; 83; 84) (1 mmol) in DMF (8 ml), CDI (2 mmol) was added. After 3 h, amine (4 mmol) was added and the resulting mixture was stirred at 50° C. for 1 h, then was loaded onto a reverse phase column (50 g) eluting with water+0.1% AcOH only to acetonitrile+0.1% AcOH only to give the title intermediates.

TABLE 7

Intermediates 85-111: Intermediate (VIII) of scheme 1

| Intermediate | Structure | Analysis | Procedure | Yield (%) |
|---|---|---|---|---|
| 85 | 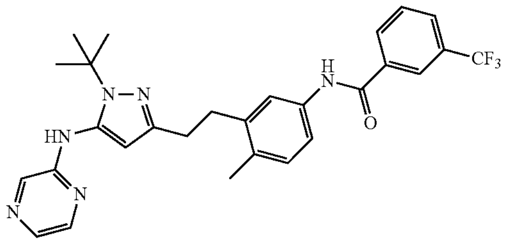 [SMILES: Cc1ccc(NC(=O)c2cccc(C(F)(F)F)c2)cc1CCc1cc(Nc2cnccn2)n(C(C)(C)C)n1] | $^1$H NMR (400 MHz, DMSO-$d_6$) δ ppm 10.32 (s, 1H), 8.62(S, 1 H), 8.32-8.29 (m, 1H), 8.28-8.23 (m, 1H), 8.06-8.03 (m, 1H), 7.99-7.94 (m, 1H), 7.94-7.92 (m, 1H), 7.90-7.87 (m, 1H), 7.81-7.76 (m, 1H), 7.65-7.62 (m, 1H), 7.56-7.51 (m, 1H), 7.13 (d, J = 8.3 Hz, 1H), 5.98 (s, 1H), 2.92-2.85 (m, 2H), 2.81-2.73 (m, 2H), 2.26 (s, 3H), 1.52 (s, 9H). ESI + m/z 523 [M + H] | 9 | 90 |
| 86 | 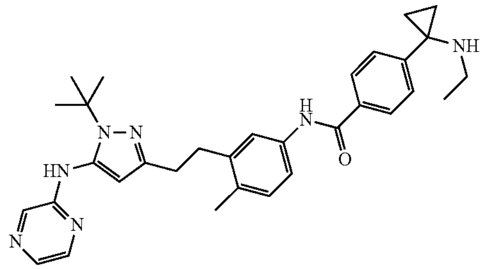 [SMILES: CCNC1(c2ccc(C(=O)Nc3ccc(C)c(CCc4cc(Nc5cnccn5)n(C(C)(C)C)n4)c3)cc2)CC1] | $^1$H NMR (400MHz, DMSO-$d_6$) δ ppm 10.04-9.94 (m, 1H), 8.67-8.57 (m, 1H), 8.08-8.01 (m, 1H), 7.95 (s, 1 H), 7.91-7.82 (m, 3H), 7.70-7.62 (m, 1H), 7.56-7.47 (m, 1H), 7.43 (d, J = 8.3 Hz, 2H), 7.13-7.05 (m, 1H), 5.99 (s, 1H), 2.90-2.83 (m, 2H), 2.79-2.71 (m, 2H), 2.49-2.39 (m, 2H), 2.25 (s, 3H), 1.52 (s, 9H), 1.00 (d, J = 6.8 Hz, 7H). ESI + m/z 538 [M + H] | 10 | 68 |
| 87 | 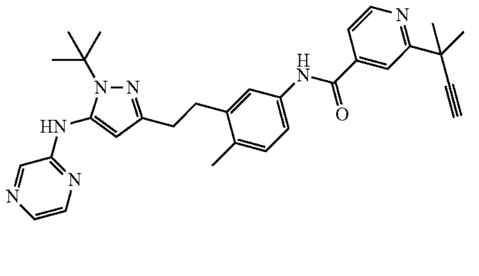 [SMILES: C#CC(C)(C)c1cc(C(=O)Nc2ccc(C)c(CCc3cc(Nc4cnccn4)n(C(C)(C)C)n3)c2)ccn1] | $^1$H NMR (400 MHz, DMSO-$d_6$) δ ppm 10.41 (1 H,S), 8.80(1 H, d, J = 4.89 Hz), 8.62 (1 H, s), 8.04 (1 H, dd, J = 2.45, 1.47 Hz), 8.00 (1 H, s), 7.93 (1 H, d, J = 1.47 Hz), 7.89 (1 H, d, J = 2.93 Hz), 7.86 (1 H, dd, J = 4.89, 1.47 Hz), 7.61 (1H, d, J = 2.45 Hz), 7.51 (1 H, dd, J = 8.07, 2.20 Hz), 7.15 (1 H, d, J = 8.31 Hz), 5.97 (1 H, s), 2.84-2.94 (2 H, m), 2.71-2.81 (2 H, m), 2.26 (3 H, s), 1.77 (6 H, s), 1.52 (9 H, s). ESI + m/z 523 [M + H] | 10 | 93 |
| 88 | 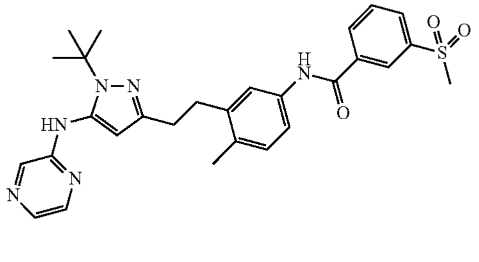 [SMILES: Cc1ccc(NC(=O)c2cccc(S(C)(=O)=O)c2)cc1CCc1cc(Nc2cnccn2)n(C(C)(C)C)n1] | $^1$H NMR (400 MHz, DMSO-$d_6$) δ ppm 10.37 (1 H, s), 8.62 (1 H, s), 8.48 (1 H, s), 8.26-8.31 (1 H, m), 8.11-8.15 (1 H, m), 8.03-8.06 (1 H, m), 7.93 (1 H, d, J = 1.47 Hz), 7.89 (1 H, d, J = 2.45 Hz), 7.82 (1 H, s), 7.62 (1 H, s), 7.51-7.55 (1 H, m), 7.09-7.17 (1 H, m), 5.98 (1 H, s), 2.84-2.93 (2 H, m), 2.71-2.80 (2 H, m), 2.26 (3 H, s), 1.52 (9H, s). ESI + m/z 533 [M + H] | 10 | 66 |

TABLE 7-continued

| Intermediates 85-111: Intermediate (VIII) of scheme 1 | | | | |
|---|---|---|---|---|
| Intermediate | Structure | Analysis | Procedure | Yield (%) |
| 89 | 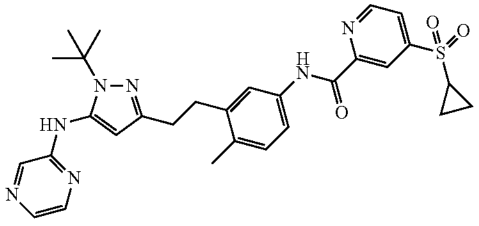 [SMILES: Cc1ccc(NC(=O)c2cc(S(=O)(=O)C3CC3)ccn2)cc1CCc1cc(Nc2cnccn2)n(C(C)(C)C)n1] | $^1$H NMR (400 MHz, DMSO-$d_6$) δ ppm 10.72-10.41 (m, 1H), 9.07-9.04 (m, 1H), 8.65-8.59 (m, 1H), 8.51-8.44 (m, 1H), 8.18-8.12 (m, 1H), 8.07-8.03 (m, 1H), 7.95-7.92 (m, 1H), 7.89-7.86 (m, 1H), 7.78-7.76 (m, 1H), 7.68-7.63 (m, 1H), 7.17-7.12 (m, 1H), 6.06-5.87 (m, 1H), 3.19-3.08 (m, 1H), 2.94-2.84 (m, 2H), 2.82-2.72 (m, 2H), 2.27 (s, 3H), 1.52 (s, 9H), 1.26-1.20 (m, 2H), 1.20-1.11 (m, 2H). ESI + m/z 560 [M + H] | 10 | 80 |
| 90 | 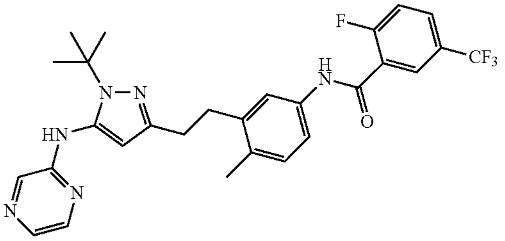 [SMILES: Cc1ccc(NC(=O)c2cc(C(F)(F)F)ccc2F)cc1CCc1cc(Nc2cnccn2)n(C(C)(C)C)n1] | $^1$H NMR (400 MHz, DMSO-$d_6$) δ ppm 10.42 (1 H, S), 8.62 (1 H, s), 7.86-8.08 (5 H, m), 7.54-7.66 (2 H, m), 7.44 (1 H, dd), 7.13 (1 H,d), 5.97 (1 H, s), 2.82-2.92 (2 H, m), 2.70-2.79 (2 H, m), 2.26 (3 H, s), 1.52 (9 H, s). ESI + m/z 541 [M + H] | 10 | 94 |
| 91 | 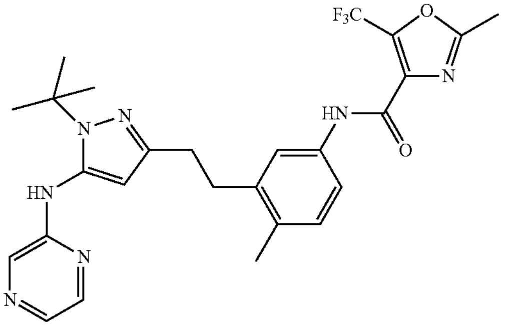 [SMILES: Cc1nc(C(=O)Nc2ccc(C)c(CCc3cc(Nc4cnccn4)n(C(C)(C)C)n3)c2)c(C(F)(F)F)o1] | $^1$H NMR (400 MHz, DMSO-$d_6$) δ ppm 10.29 (1 H, s), 8.62 (1 H, s), 8.05 (1 H, dd), 7.93 (1 H, d), 7.89 (1 H, d), 7.70 (1 H, d), 7.51 (1 H, dd), 7.10 (1 H, d), 5.99 (1 H, s), 2.86 (2 H, d), 2.71- 2.79 (2 H, m), 2.61 (3 H, s), 2.25 (3 H, s), 1.52 (9 H, s). ESI + m/z 528 [M+H] | 10 | 87 |
| 92 | 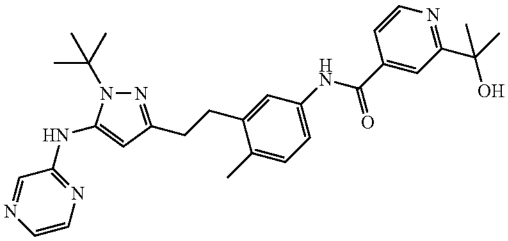 [SMILES: Cc1ccc(NC(=O)c2ccnc(C(C)(C)O)c2)cc1CCc1cc(Nc2cnccn2)n(C(C)(C)C)n1] | $^1$H NMR (400 MHz, DMSO-d6) δ ppm 10.29-10.41 (1 H, m), 8.64-8.69 (1 H, m), 8.59-8.64 (1 H, m), 8.11-8.16 (1 H, m), 8.02-8.06 (1 H, m), 7.92-7.96 (1 H, m), 7.87-7.91 (1 H, m), 7.67-7.72 (1 H,m), 7.61-7.65 (1 H, m), 7.52 (1 H, s), 7.11-7.16 (1 H, m), 5.97-6.00 (1 H, m), 5.31-5.35 (1 H, m), 2.83-2.93 (2 H, m), 2.72-2.80 (2 H, m), 2.26 (3 H, s), 1.52 (9 H, s), 1.49 (6 H, s). ESI + m/z 514 [M+H] | 10 | 45 |
| 93 | 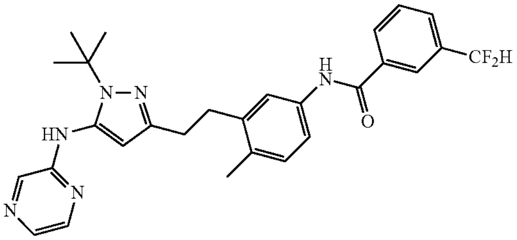 [SMILES: Cc1ccc(NC(=O)c2cccc(C(F)F)c2)cc1CCc1cc(Nc2cnccn2)n(C(C)(C)C)n1] | ESI + m/z 505 [M + H] | 10 | 64 |

TABLE 7-continued

| Intermediates 85-111: Intermediate (VIII) of scheme 1 | | | | |
|---|---|---|---|---|
| Intermediate | Structure | Analysis | Procedure | Yield (%) |
| 94 | 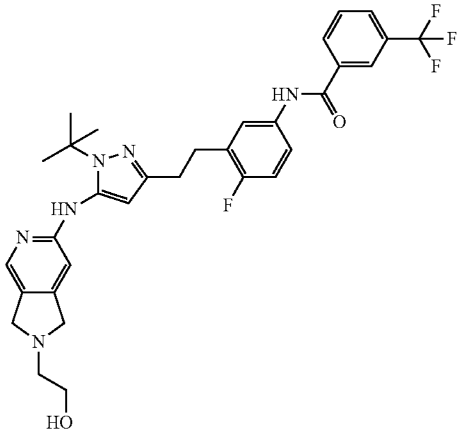 [SMILES: CC(C)(C)n1nc(CCc2cc(NC(=O)c3cccc(C(F)(F)F)c3)ccc2F)cc1Nc1cc2c(cn1)CN(CCO)C2] | ESI + m/z 611 [M + H] | 9 | 25 |
| 95 | 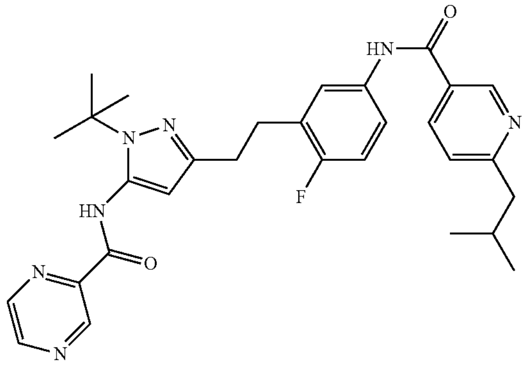 [SMILES: CC(C)Cc1ccc(C(=O)Nc2ccc(F)c(CCc3cc(NC(=O)c4cnccn4)n(C(C)(C)C)n3)c2)cn1] | 1H NMR (400 MHz, methanol-$d_4$) δ ppm 9.03 (2 H, d, J = 5.38 Hz), 9.01 (1 H, d, J = 1.96 Hz), 8.30 (1 H, dd, J = 8.07, 2.20 Hz), 7.73 (1 H, t, J = 4.89 Hz), 7.54-7.60 (1 H, m), 7.52 (1 H, d, J = 6.85 Hz), 7.43 (1 H, d, J = 8.31 Hz), 7.07 (1 H, t, J = 9.05 Hz), 6.25 (1 H, s), 3.01 (2 H, d, J = 7.83 Hz), 2.95 (2 H, dd, J = 6.85, 1.47 Hz), 2.76 (2 H, d, J = 7.34 Hz), 2.09-2.17 (1 H, m), 1.65 (9 H, s), 0.98 (3 H, s), 0.96 (3 H, s).<br>ESI + m/z 544 [M + H] | 10 | 65 |
| 96 | 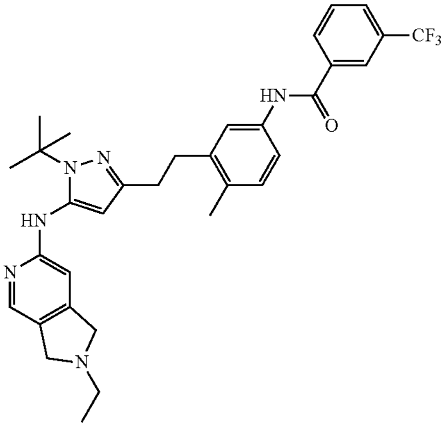 [SMILES: CCN1Cc2cnc(Nc3cc(CCc4cc(NC(=O)c5cccc(C(F)(F)F)c5)ccc4C)nn3C(C)(C)C)cc2C1] | $^1$H NMR (400 MHz, DMSO-$d_6$) δ ppm 10.32 (s, 1 H), 8.33-8.23 (m, 2H), 7.95 (d, J = 3.9 Hz, 1H), 7.89 (s, 1H), 7.82-7.75 (m, 1H), 7.62 (d, J = 2.0 Hz, 1H), 7.54 (dd, J = 2.2, 8.1 Hz, 1H), 7.13 (d, J = 8.3 Hz, 1H), 6.28 (s, 1H), 5.87 (s, 1H), 3.68 (d, J = 5.9 Hz, 4H), 2.89-2.84 (m, 2H), 2.80-2.75 (m, 2H), 2.62 (q, J = 7.3 Hz, 2H), 1.51 (s, 9H), 1.06 (t, J = 7.1 Hz, 3H).<br>ESI + m/z 591 [M + H] | 9 | 81 |
| 97 | 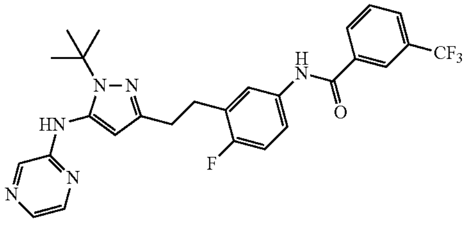 [SMILES: CC(C)(C)n1nc(CCc2cc(NC(=O)c3cccc(C(F)(F)F)c3)ccc2F)cc1Nc1cnccn1] | $^1$H NMR (400 MHz, $CDCl_3$) δ ppm 8.67 (1 H, br. s.), 8.17-8.27 (2 H, m), 8.12 (1 H, d), 8.06 (1 H, s), 7.93-8.00 (1 H, m), 7.83 (1 H, s), 7.62-7.72 (1 H, m), 7.45-7.58 (2 H, m), 7.03 (2 H, t), 6.79-6.96 (1 H, m), 3.09 (4 H, dd), 1.59-1.70.<br>ESI + m/z 527 [M + H] | 9 | 98 |

TABLE 7-continued

Intermediates 85-111: Intermediate (VIII) of scheme 1

| Intermediate | Structure | Analysis | Procedure | Yield (%) |
|---|---|---|---|---|
| 98 | 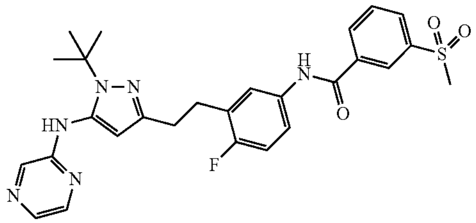 | $^1$H NMR (400 MHz, DMSO-d$^6$) δ ppm 10.48 (1 H, s), 8.60 (1 H, s), 8.48 (1 H, s), 8.28 (1 H, d), 8.14 (1H, d), 8.02-8.06 (1 H, m), 7.92 (1 H, s), 7.88 (1 H, s), 7.83 (1 H, t), 7.74 (1 H, dd), 7.63 (1 H, d), 7.16 (2 H, t), 5.98 (1 H, s), 2.89-2.98 (3 H, m), 2.77-2.85 (2 H, m), 1.51 (10 H, s). ESI + m/z 537 [M + H] | 10 | 66 |
| 99 | 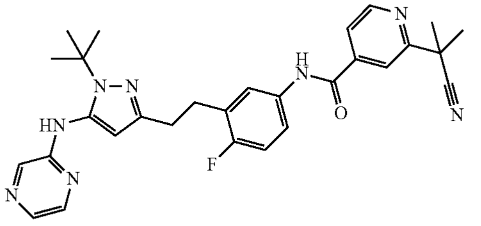 [SMILES: CC(C)(C#N)c1cc(C(=O)Nc2ccc(F)c(CCc3cc(Nc4cnccn4)n(C(C)(C)C)n3)c2)ccn1] | $^1$H NMR (400 MHz, DMSO-d$_6$) δ ppm 10.52 (1 H,s), 8.81 (1 H, d, J = 4.89 Hz), 8.62 (1 H, s), 8.04 (1 H, dd, J = 2.45, 1.47 Hz), 8.00 (1 H, s), 7.82-7.94 (3 H, m), 7.56-7.75 (2 H, m), 7.11-7.23 (1 H, m), 5.98 (1 H, s), 2.93 (2 H, d, J = 8.31 Hz), 2.75-2.85 (2 H, m), 1.77 (6 H, s), 1.50 (9 H, s). ESI + m/z 527 [M + H] | 10 | 84 |
| 100 | 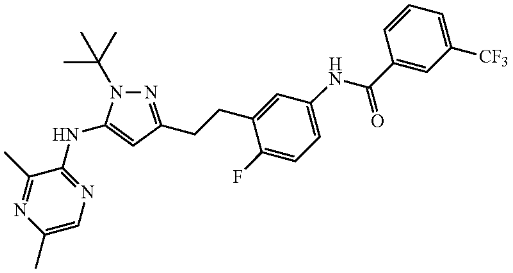 [SMILES: Cc1cnc(Nc2cc(CCc3cc(NC(=O)c4cccc(C(F)(F)F)c4)ccc3F)nn2C(C)(C)C)c(C)n1] | ESI + m/z 555 [M + H] | 10 | 56 |
| 101 | 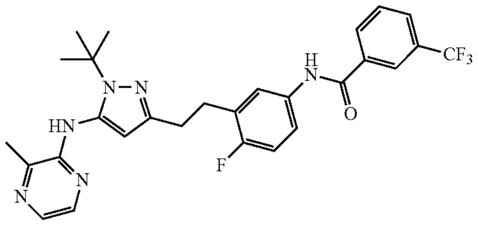 [SMILES: Cc1nccnc1Nc1cc(CCc2cc(NC(=O)c3cccc(C(F)(F)F)c3)ccc2F)nn1C(C)(C)C] | $^1$H NMR (400 MHz, DMSO-d$_6$) δ ppm 10.44 (1 H, s), 8.24-8.32 (2 H, m), 7.95-8.01 (2 H, m), 7.74-7.88 (4 H, m), 7.61-7.68 (1 H, m), 7.17 (1 H, t, J = 9.29 Hz), 5.93 (1 H, s), 2.92 (2 H, d, J = 8.31 Hz), 2.82 (2 H, d, J = 8.80 Hz), 2.44 (3 H, s), 1.48 (9 H, s). ESI + m/z 541 [M + H] | 10 | 79 |
| 102 | 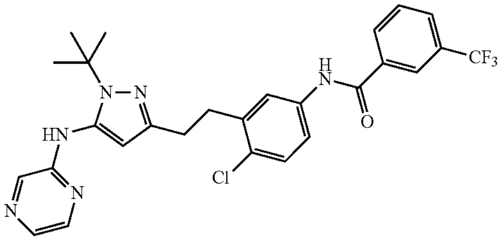 | ESI + m/z 545 [M + H] | 9 | 57 |
| 103 | 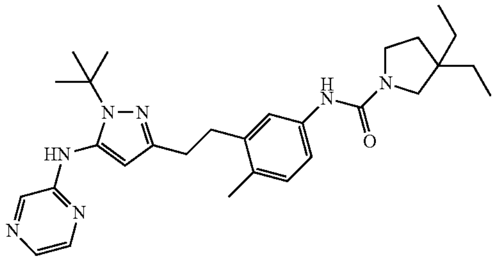 [SMILES: CCC1(CC)CCN(C(=O)Nc2ccc(C)c(CCc3cc(Nc4cnccn4)n(C(C)(C)C)n3)c2)C1] | $^1$H NMR (400 MHz, DMSO-d$_6$) δ ppm 8.61 (1 H, s), 8.05 (1 H, br. s.), 7.82-7.98 (3 H, m), 7.35 (1 H, br. s.), 7.26 (1 H, d), 6.96 (1 H, d), 5.96 (1 H, s), 3.39 (2 H, t), 3.14 (2 H, s), 2.78 (2 H, d), 2.71 (2 H, d), 2.18 (3 H, s), 1.66 (2 H, t), 1.46-1.58 (8 H, m), 1.38 (4 H, d), 0.83 (6 H, t). ESI + m/z 504 [M + H] | 11 | 97 |

TABLE 7-continued

| Intermediates 85-111: Intermediate (VIII) of scheme 1 | | | | |
|---|---|---|---|---|
| Intermediate | Structure | Analysis | Procedure | Yield (%) |
| 104 | 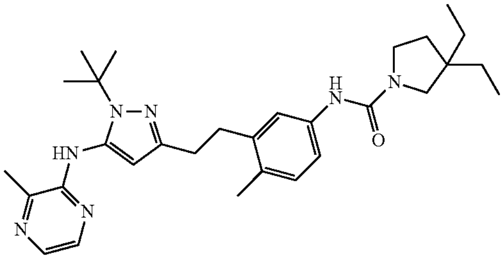 [SMILES: CCC1(CC)CCN(C(=O)Nc2ccc(C)c(CCc3cc(Nc4nccnc4C)n(C(C)(C)C)n3)c2)C1] | $^1H$ NMR (400 MHz, DMSO-$d_6$) δ ppm 7.99 (s, 1 H), 7.92-7.85 (m, 2H), 7.78 (d, J = 1.0 Hz, 1H), 7.37 (d, J = 1.0 Hz, 1H), 7.27 (t, J = 1.0 Hz, 1H), 6.97 (d, J = 1.0 Hz, 1H), 5.92 (s, 1H), 3.40 (t, J = 1.0 Hz, 2H), 3.16 (s, 2H), 2.86-2.76 (m, 2H), 2.76-2.69 (m, 2H), 2.44 (s, 3H), 2.21 (s, 3H), 1.72-1.64 (m, 2H), 1.50 (s, 9H), 1.43-1.29 (m, 4H), 0.90-0.79 (m, 6H). ESI + m/z 518 [M + H] | 11 | 86 |
| 105 | 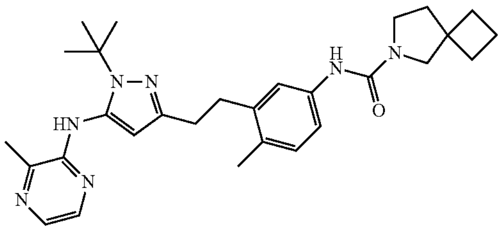 [SMILES: Cc1ccc(NC(=O)N2CCC3(CCC3)C2)cc1CCc1cc(Nc2nccnc2C)n(C(C)(C)C)n1] | $^1H$ NMR (400 MHz, DMSO-$d_6$) δ ppm 7.98 (s, 1H), 7.90 (s, 1H), 7.87 (d, J = 2.9 Hz, 1H), 7.78 (d, J = 1.0 Hz, 1H), 7.37 (d, J = 1.0 Hz, 1H), 7.26 (t, J = 1.0 Hz, 1H), 6.97 (d, J = 1.0 Hz, 1H), 5.92 (s, 1 H), 3.39-3.33 (m, 4H), 2.84-2.76 (m, 2H), 2.75-2.68 (m, 2H), 2.45 (s, 3H), 2.21 (s, 3H), 2.02-1.85 (m, 8H), 1.50 (s, 9H). ESI + m/z 502 [M + H] | 11 | 54 |
| 106 | 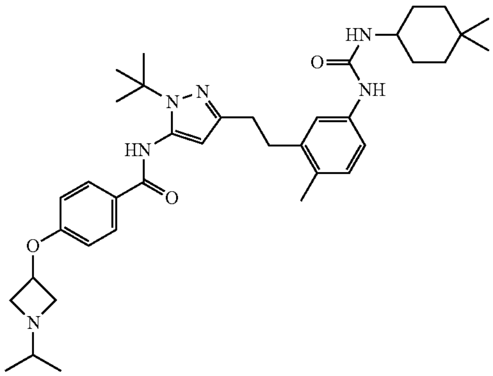 [SMILES: Cc1ccc(NC(=O)NC2CCC(C)(C)CC2)cc1CCc1cc(NC(=O)c2ccc(OC3CN(C(C)C)C3)cc2)n(C(C)(C)C)n1] | ESI + m/z 643 [M + H] | 11 | 88 |
| 107 | 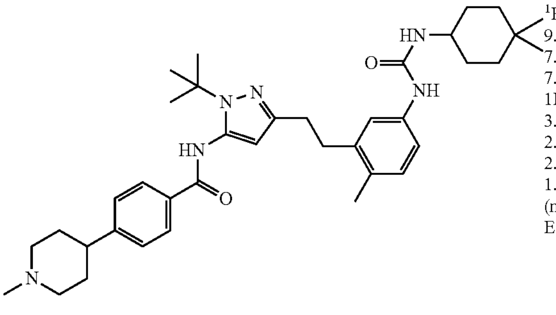 | $^1H$ NMR (400 MHz, DMSO-$d_6$) δ ppm 9.88 (s, 1H), 8.14-8.08 (m, 1H), 7.92-7.85 (m, 2H), 7.41 (d, J = 8.3 Hz, 2H), 7.27-7.20 (m, 1H), 7.14-7.08 (m, 1H), 6.98 (s, 1H), 6.02 (s, 2H), 3.47-3.36 (m, 1H), 2.96-2.87 (m, 2H), 2.84-2.76 (m, 2H), 2.72 (br. s., 2H), 2.26-2.16 (m, 6H), 2.02 (br. s., 2H), 1.84-1.61 (m, 6H), 1.54 (s, 9H), 1.40-1.18 (m, 6H), 0.91 (d, J = 2.0 Hz, 6H). ESI + m/z 627 [M + H] | 11 | 38 |
| 108 | 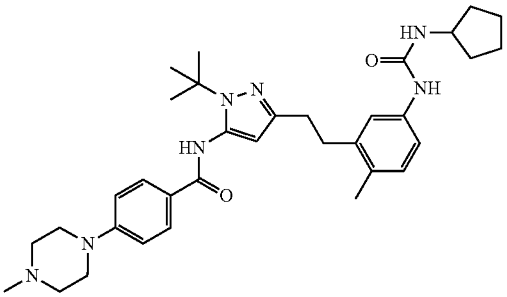 [SMILES: Cc1ccc(NC(=O)NC2CCCC2)cc1CCc1cc(NC(=O)c2ccc(N3CCN(C)CC3)cc2)n(C(C)(C)C)n1] | ESI + m/z 586 [M + H-tBu] | 11 | 93 |

TABLE 7-continued
| Intermediates 85-111: Intermediate (VIII) of scheme 1 | | | | |
|---|---|---|---|---|
| Intermediate | Structure | Analysis | Procedure | Yield (%) |
| 109 | 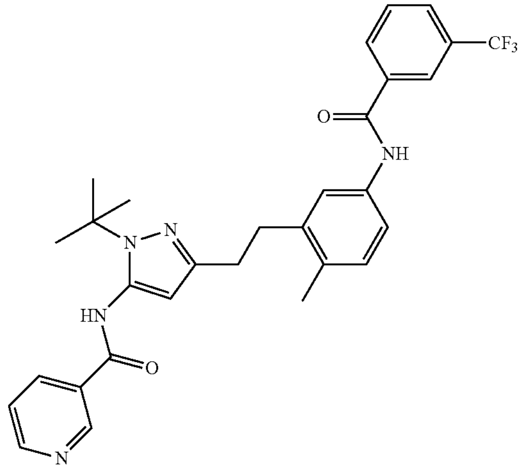 [SMILES: Cc1ccc(NC(=O)c2cccc(C(F)(F)F)c2)cc1CCc1cc(NC(=O)c2cccnc2)n(C(C)(C)C)n1] | ESI + m/z 550 [M + H] | 9 | 84 |
| 110 | 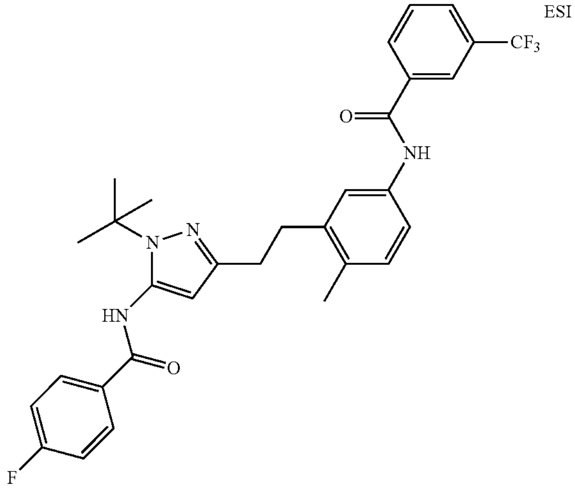 | ESI + m/z 567 [M + H] | 9 | 78 |
| 111 | 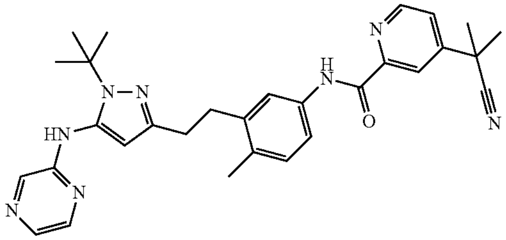 [SMILES: Cc1ccc(NC(=O)c2cc(C(C)(C)C#N)ccn2)cc1CCc1cc(Nc2cnccn2)n(C(C)(C)C)n1] | ESI + m/z 523 [M + H] | 10 | 87 |

Example 36

Preparation of Intermediate 112 methyl 6-((5-(2-fluoro-5-(3-(trifluoromnethyl)benzamnido)phenethyl)-1H-pyrazol-3-yl)amino)-2-methylpyrimidine-4-carboxylate

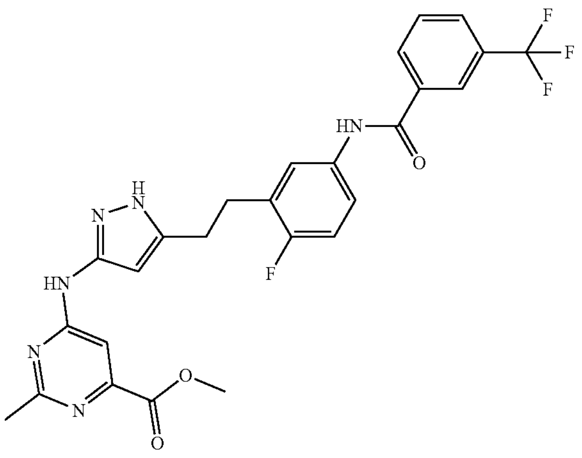 [SMILES: COC(=O)c1cc(Nc2cc(CCc3cc(NC(=O)c4cccc(C(F)(F)F)c4)ccc3F)[nH]n2)nc(C)n1]

3-(trifluoromethyl)benzoyl chloride (0.098 ml, 0.648 mmol) was added to a solution of intermediate 72 (160 mg, 0.432 mmol) in pyridine (1 ml, 12.36 mmol) and the resulting mixture was stirred for 1 h. Solvent was evaporated, the residue was dissolved in MeOH and NaOMe (100 mg) was added. The mixture was stirred overnight at RT.

Solvent was evaporated and the residue was portioned between AcOEt and diluted HC. The separated organic phase was concentrated and the residue was purified via silica gel column (25 g) eluting with cyclohexane 100% to AcOEt 100% to give title intermediate (155 mg; yellow solid).

ESI+m/z 543 [M+H]

Example 37

Preparation of Intermediate 113

N-(4-fluoro-3-(2-(3-((6-(hydroxymethyl)-2-methylpyrimidin-4-yl)amino)-1H-pyrazol-5-yl)ethyl)phenyl)-3-(trifluoromethyl)benzamide

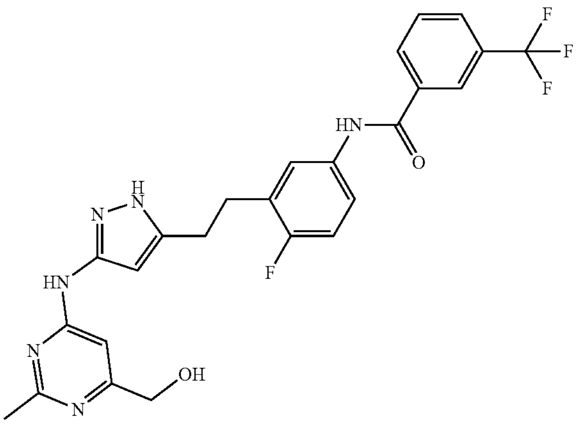 [SMILES: Cc1nc(CO)cc(Nc2cc(CCc3cc(NC(=O)c4cccc(C(F)(F)F)c4)ccc3F)[nH]n2)n1]

To a solution of intermediate 112 (155 mg, 0.286 mmol) in THF (3 ml), $LiBH_4$ in THF (0.179 ml, 0.714 mmol) was added and the mixture was stirred at RT for 1 h.

AcOH was added, the solution was evaporated. The residue was dissolved in AcOH (2 ml) and evaporated again. The residue was purified by reverse phase chromatography (50 g; water/AcOH 0.1% to ACN/AcOH 0.1%). The relevant fractions were collected concentrated, basified with NaOH 1 N, extracted with AcOEt, washed with brine, dried and concentrated to give title intermediate (70 mg; white solid).

$^1H$ NMR (400 MHz, DMSO-$d_6$) δ ppm 12.08 (1H, br. s.), 10.47 (1H, s), 9.57 (1H, br. s), 8.20-8.36 (2H, m), 7.98 (1H, d), 7.71-7.84 (2H, m), 7.59-7.71 (1H, m), 7.19 (2H, m), 6.17 (1H, br. s), 5.23-5.40 (1H, m), 4.33 (2H, d), 2.83-3.03 (4H, m), 2.37 (3H, s).

ESI+m/z 515 [M+H]

Example 38

Preparation of Intermediate 114

(6-((5-(2-fluoro-5-(3-(trifluoromethyl)benzamido)phenethyl)-1H-pyrazol-3-yl)amino)-2-methylpyrimidin-4-yl)methyl methanesulfonate

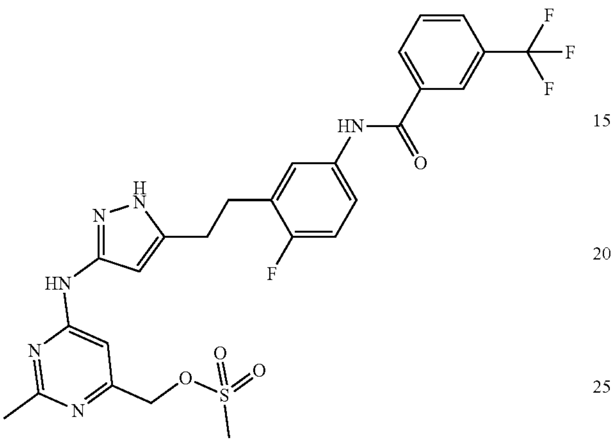

To a solution of intermediate 113 (70 mg, 0.136 mmol) and N,N-Diethylethanamine (0.038 ml, 0.272 mmol) in THF (6 ml) at 0° C., Mesyl Chloride (0.016 ml, 0.204 mmol) was added and the resulting mixture was left stirring at RT for 3 h. The solution was used directly in the subsequent reactions. (see example 46, compounds 26, 27 and 28)

Example 39

Preparation of Intermediate 115

N-(3-(2-(5-((6-chloro-2-methylpyrimidin-4-yl)amino)-1H-pyrazol-3-yl)ethyl)-4-fluorophenyl)-3-(trifluoromethyl)benzamide

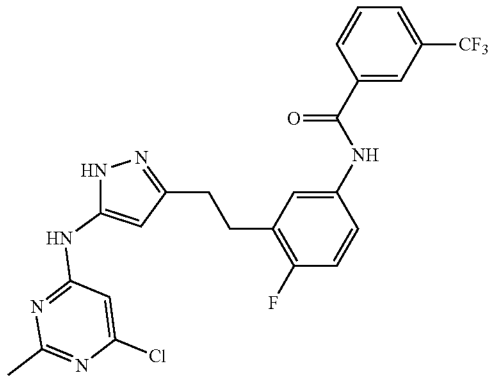 [SMILES: Cc1nc(Cl)cc(Nc2cc(CCc3cc(NC(=O)c4cccc(C(F)(F)F)c4)ccc3F)n[nH]2)n1]

3-(trifluoromethyl)benzoyl chloride (0.098 ml, 0.648 mmol) was added to a solution of intermediate 78 (150 mg, 0.433 mmol) in pyridine (1 ml, 12.36 mmol) and the resulting mixture was stirred for 1 h. Solvent was evaporated, the residue was dissolved in MeOH and NaOMe (100 mg) was added. The mixture was stirred overnight at RT.

Solvent was evaporated and the residue was portioned between AcOEt and diluted HCl. The separated organic phase was concentrated and the residue was purified via silica gel column (25 g) eluting with cyclohexane 100% to AcOEt 100% to give title intermediate (165 mg; yellow solid).

$^1$H NMR (400 MHz, DMSO-$d_6$) δ ppm 12.21 (1H, br. s.), 10.46 (1H, s), 10.07 (1H, s), 8.19-8.34 (2H, m), 7.98 (1H, d), 7.59-7.86 (3H, m), 7.19 (1H, t), 6.07 (1H, br. s.), 2.83-3.01 (4H, m), 2.40 (3H, s).

ESI+m/z 519 [M+H]

Example 40

Preparation of Intermediate (X) (Intermediate 116) of Scheme 2

N-(5-(2-(5-amino-1-(tert-butyl)-1H-pyrazol-3-yl)ethyl)-2-fluorophenyl)-3-(trifluoromethyl) benzamide

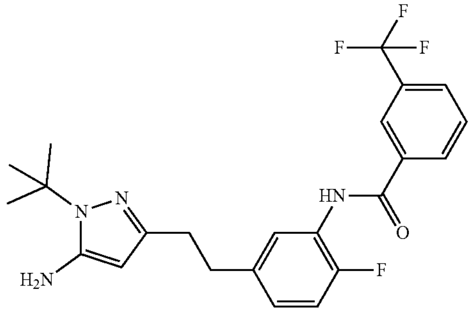 [SMILES: CC(C)(C)n1nc(CCc2ccc(F)c(NC(=O)c3cccc(C(F)(F)F)c3)c2)cc1N]

To intermediate 16 (500 mg, 1.470 mmol), 3-(trifluoromethyl)benzamide (834 mg, 4.41 mmol), potassium phosphate tribasic (936 mg, 4.41 mmol), Tetramethyl di-tBuXPhos (70.6 mg, 0.147 mmol), tris(dibenzylideneacetone) palladium (0) (60.6 mg, 0.066 mmol) under nitrogen, was added dry dioxane (10 ml). The resulting mixture was heated to 105° C. and left at this temperature overnight. The reaction was cooled to RT and then stripped of dioxane under vacuum. To the remaining residue was added DCM (15 ml) and water (20 ml). After brief mixing the organic layer was separated, dried over anhydrous sodium sulphate and then evaporated to a brown residue. Purification: silica gel column (25 g) eluting with DCM to DCM/AcOEt 1:1 to obtain title intermediate (597 mg; brown solid).

$^1$H NMR (400 MHz, DMSO-$d_6$) δ ppm 10.34 (1H, s), 8.24-8.35 (2H, m), 7.99 (1H, d), 7.73-7.85 (1H, m), 7.48 (1H, dd), 7.08-7.23 (2H, m), 5.25 (1H, s), 4.72 (2H, s), 2.77-2.87 (2H, m), 2.57-2.66 (2H, m), 1.49 (9H, s).

ESI+m/z 449 [M+H]

Example 41

Preparation of Intermediate (XI) (Intermediate 117) of Scheme 2

N-(5-(2-(5-amino-1-(tert-butyl)-1H-pyrazol-3-yl) ethyl)-2-fluorophenyl)-3-(trifluoromethyl) benzamide

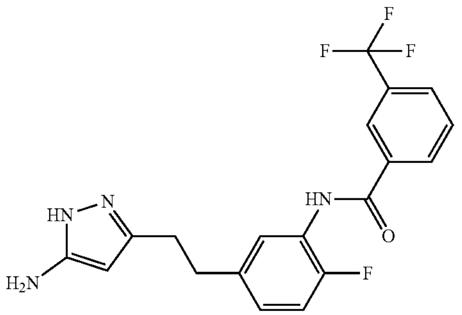 [SMILES: Nc1cc(CCc2ccc(F)c(NC(=O)c3cccc(C(F)(F)F)c3)c2)n[nH]1]

To intermediate 116 (590 mg, 1.316 mmol) was added formic acid (24.8 ml, 658 mmol). The resulting solution was heated to 100° C. for 24 hours. The reaction was then stripped of volatiles, the remaining residue was dissolved in DMSO (2 ml) and purified by reverse phase chromatography (50 g; water/AcOH 0.1% to ACN/AcOH 0.1%). Yield: 495 mg; yellow solid.

$^1$H NMR (400 MHz, DMSO-$d_6$) δ ppm 11.11 (1H, br. s.), 10.36 (1H, s), 8.22-8.37 (2H, m), 7.99 (1H, d), 7.73-7.86 (1H, m), 7.48 (1H, dd), 7.08-7.27 (2H, m), 5.21 (1H, br. s.), 4.41 (2H, br. s.), 2.64-2.92 (4H, m).

ESI+m/z 393 [M+H]

Example 42

Preparation of Intermediate 118

N-(5-(2-(5-((6-chloro-2-methylpyrimidin-4-yl) amino)-1H-pyrazol-3-yl)ethyl)-2-fluorophenyl)-3-(trifluoromethyl)benzamide

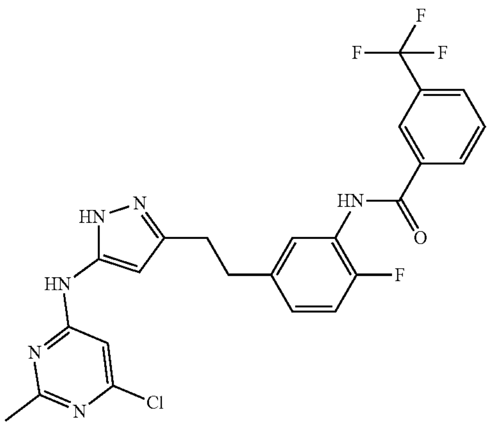 [SMILES: Cc1nc(Cl)cc(Nc2cc(CCc3ccc(F)c(NC(=O)c4cccc(C(F)(F)F)c4)c3)n[nH]2)n1]

To intermediate 117 (150 mg, 0.382 mmol) in dry DMSO (2 mL) was added solid 4,6-dichloro-2-methylpyrimidine (68.6 mg, 0.421 mmol) followed by N-ethyl-N-isopropylpropan-2-amine (0.200 mL, 1.147 mmol). The resulting mixture was left to stir at 60° C. for 24 hours. The reaction was then stripped of volatiles, the remaining residue was dissolved in acetic acid (0.3 ml) and purified by reverse phase chromatography (50 g; water/AcOH 0.1% to ACN/AcOH 0.1%). Yield: 158 mg; yellow solid.

$^1$H NMR (400 MHz, DMSO-$d_6$) δ ppm 12.17 (1H, br. s.), 10.36 (1H, s), 10.07 (1H, s), 8.19-8.36 (2H, m), 7.99 (1H, d), 7.80 (1H, t), 7.52 (1H, dd), 7.10-7.31 (2H, m), 5.74-6.32 (1H, m), 2.82-3.00 (4H, m), 2.41 (3H, s).

ESI+m/z 519 [M+H]

Example 43

Preparation of Intermediate (XIII) (Intermediate 119) of Scheme 3

3-(3-aminophenethyl)-1-(tert-butyl)-1H-pyrazol-5-amine

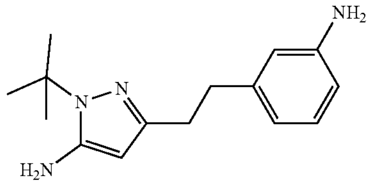 [SMILES: CC(C)(C)n1nc(CCc2cccc(N)c2)cc1N]

To copper monoidide (0.259 g, 1.358 mmol), (S)-pyrrolidine-2-carboxylic acid (0.313 g, 2.72 mmol) and potassium carbonate (2.252 g, 16.29 mmol) in a high pressure vial was added dry and degassed DMSO (8 ml). The resulting purple colored mixture was left to stir for 10 minutes. After 10 minutes, intermediate 18 (1.75 g, 5.43 mmol) was added at once as a solid. The vial was then sealed and once sealed, ammonia, 28% in water (4 ml, 59.0 mmol) was added. The resulting mixture was then heated to 100° C. for 8 hour in a microwave. The reaction was cooled to RT and then added dropwise to water/DCM (20 ml). After brief mixing, the organic layer was separated, dried over anhydrous sodium sulphate and then evaporated to a dark blue oil. Purification: silica gel column (55 g) eluting with cHex/DCM 75:25, then reverse phase column (150 g) eluting with water/AcOH 0.1% to ACN/AcOH 0.1%. Yield 1.178 g of title intermediate as an off-white solid.

$^1$H NMR (400 MHz, DMSO-$d_6$) δ ppm 6.90 (1H, t), 6.45 (1H, t), 6.30-6.42 (2H, m), 5.23 (1H, s), 4.89 (2H, br. s.), 4.70 (2H, s), 2.59-2.67 (2H, m), 2.53-2.58 (2H, m), 1.50 (9H, s).

ESI+m/z 259 [M+H]

Example 44

Preparation of Intermediate (XIV) (Intermediate 120) of Scheme 3

N-(3-(2-(5-amino-1-(tert-butyl)-1H-pyrazol-3-yl)ethyl)phenyl)-4-((dimethylamino)methyl) benzamide

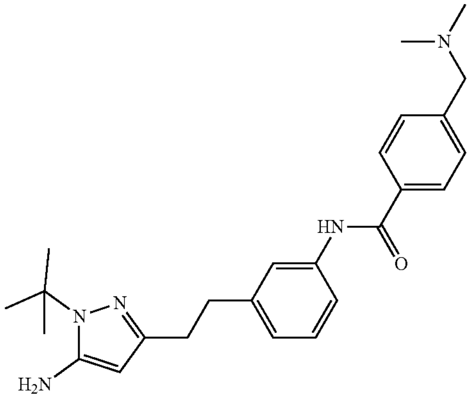 [SMILES: CN(C)Cc1ccc(C(=O)Nc2cccc(CCc3cc(N)n(C(C)(C)C)n3)c2)cc1]

To intermediate 119 (150 mg, 0.581 mmol) in dry DCM (4 ml) was added dry pyridine (0.235 ml, 2.90 mmol). To the resulting solution was added dropwise intermediate 42 (163 mg, 0.697 mmol). Once addition was complete, the reaction was stirred at RT overnight. To the reaction was then added saturated aqueous sodium bicarbonate solution. After brief mixing, the organic layer was separated, dried over anhydrous sodium sulphate and then evaporated to a brown oil. Purification: silica gel column (25 g) eluting with cHex/AcOEt 1:1 to AcOEt. Yield 185 mg (yellow solid).

$^1$H NMR (400 MHz, DMSO-$d_6$) δ ppm 10.12 (1H, s), 7.93 (2H, d), 7.68 (1H, s), 7.62 (1H, d), 7.45 (2H, d), 7.24 (1H, t), 6.98 (1H, d), 5.25 (1H, s), 4.72 (2H, s), 3.51 (2H, br. s.), 2.80 (2H, dd), 2.59-2.66 (2H, m), 2.20 (6H, s), 1.50 (9H, s).

ESI+m/z 420 [M+H]

Example 45

Preparation of Intermediate (XV) (Intermediate 121) of Scheme 3

N-(1-(tert-butyl)-3-(3-(4-((dimethylamino)methyl)benzamido)phenethyl)-1H-pyrazol-5-yl)-4-morpholinobenzamide

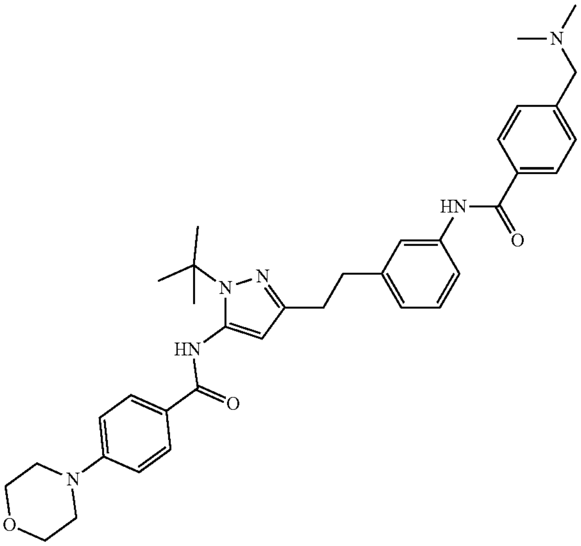 [SMILES: CN(C)Cc1ccc(C(=O)Nc2cccc(CCc3cc(NC(=O)c4ccc(N5CCOCC5)cc4)n(C(C)(C)C)n3)c2)cc1]

To intermediate 120 (80 mg, 0.191 mmol) in dry DCM (4 ml) was added pyridine (0.077 ml, 0.953 mmol) followed by 4-morpholinobenzoyl chloride (86 mg, 0.381 mmol). The resulting mixture was left to stir overnight. To the reaction was added saturated aqueous sodium bicarbonate solution (2 ml) and water (2 ml); the organic layer was separated, dried over anhydrous sodium sulphate and then evaporated to a dark brown residue. Purification: reverse phase column (150 g) eluting with water/AcOH 0.1% to ACN/AcOH 0.1%. Yield 140 mg (light brown oil).

ESI+m/z 609 [M+H]

Example 46

Preparation of Intermediate (XVII) (Intermediate 122) of Scheme 4 tert-butyl (4-methyl-3-(2-(2-(pyrazin-2-ylamino)thiazol-5-yl)ethyl)phenyl)carbamate

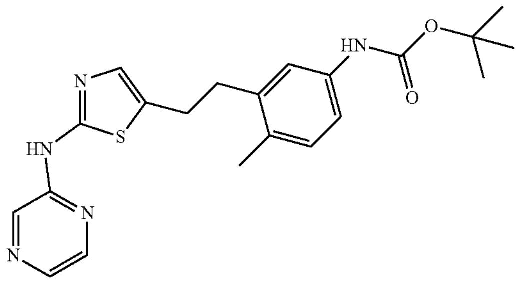 [SMILES: Cc1ccc(NC(=O)OC(C)(C)C)cc1CCc1cnc(Nc2cnccn2)s1]

An oven-dried microwave test tube equipped with a magnetic stir was charged with 4,5-Bis(diphenylphosphino)-9,9-dimethylxanthene (0.038 g, 0.066 mmol) and Tris (dibenzylideneacetone)dipalladium (0) (0.018 g, 0.020 mmol), intermediate 26 (0.22 g, 0.660 mmol) and 2-bromopyrazine (0.066 ml, 0.726 mmol). The vessel was evacuated and backfilled with nitrogen (three times). To this vessel was added Dioxane (5 ml) and evacuated and backfilled with nitrogen. The reaction was heated at 95° C. overnight then cooled to room temperature, volatiles were evaporated off and the crude dissolved in DMSO (3 ml) and AcOH (2 ml). Purification: reverse phase column (50 g) eluting with water/AcOH 0.1% to ACN/AcOH 0.1%.

Yield 262 mg of title intermediate (yellow solid).

$^1H$ NMR (400 MHz, DMSO-$d_6$) δ ppm 11.41-11.63 (1H, m), 9.13 (1H, s), 8.45 (1H, s), 8.28 (1H, dd), 8.09 (1H, d), 7.79 (1H, s), 7.43-7.53 (1H, m), 7.27-7.43 (3H, m), 7.11-7.21 (2H, m), 7.02 (1H, d), 2.78-3.01 (4H, m), 2.21 (3H, s), 1.46 (9H, s).

ESI+m/z 412 [M+H]

Example 47

Preparation of Intermediate (XVIII) (Intermediate 123) of Scheme 4

5-(5-amino-2-methylphenethyl)-N-(pyrazin-2-yl) thiazol-2-amine

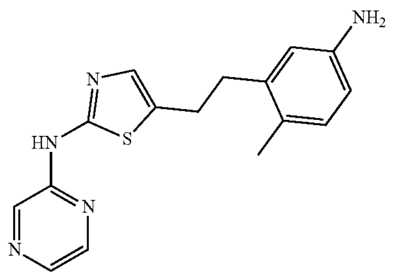 [SMILES: Cc1ccc(N)cc1CCc1cnc(Nc2cnccn2)s1]

To a solution of intermediate 122 (369 mg, 0.897 mmol) in DCM (5 ml) at RT, was slowly added TFA (0.691 ml, 8.97 mmol) and the reaction stirred at RT for 2 hours. Volatiles were evaporated and the crude loaded onto a SPE-SCX (5 g). Basic fractions were collected and evaporated to give title intermediate (196 mg; yellow solid).

$^1H$ NMR (400 MHz, DMSO-$d_6$) δ ppm 11.38-11.59 (1H, m), 8.42-8.51 (1H, m), 8.22-8.33 (1H, m), 8.03-8.16 (1H, m), 7.16 (1H, s), 6.71-6.85 (1H, m), 6.44 (1H, d), 6.34 (1H, dd), 4.68-4.91 (2H, m), 2.86-2.98 (2H, m), 2.74 (2H, br. s.), 2.12 (3H, s).

ESI+m/z 312 [M+H]

Example 48

General Procedures Used to Prepare Compounds of Inventions (Formula I) of Scheme 1

General procedure 12:

Intermediates 85-111 (1 mmol) were dissolved in formic acid (100 mmol). The resulting mixture was heated at 95° C. for 2 h. Solvent was evaporated and the residue purified on reverse phase column (25 g) eluting with water/AcOH 0.1% to ACN/AcOH 0.1%. Fractions containing the desired product were loaded on Strata-XL-C 100 μm SPE (2 g) cartridges eluting with $H_2O$/MeOH and $NH_3$ 1M in MeOH. Ammonia fractions were evaporated to obtain title compounds.

General Procedure 13:

Carboxylic acids (1.5 mmol), HOBT (1.5 mmol), EDC (1.5 mmol) and DIPEA (3 mmol) were dissolved in DMF (10 ml) under nitrogen. After 15 minutes of activation, this mixture was added to a solution of intermediate (VII) (intermediates 67; 68; 69; 77) in DMF (7.5 ml). The resulting mixture was stirred 5-7 h at RT. The solvent was evaporated and the residue was purified by reverse phase chromatography (50 g), eluting with $H_2O$—AcOH (0.1%) to $CH_3CN$—AcOH (0.1%) in gradient.

Fractions containing the desired product were loaded on Strata-XL-C 100 μm SPE (2 g) cartridges eluting with $H_2O$/MeOH and $NH_3$ 1M in MeOH. Ammonia fractions were evaporated to give title compounds.

General Procedure 14:

To Intermediate 115 (0.1 mmol) in dry DMSO (3 ml) were added the corresponding amines (1 mmol). The resulting solution was then heated to 80° C. for 5-8 hours, cooled to RT, acetic acid was added (0.5 ml) and the resulting mixture was purified by reverse phase chromatography (25 g), eluting with $H_2O$—AcOH (0.1%) to $CH_3CN$—AcOH (0.1%) in gradient.

General Procedure 15:

The THF solution containing Intermediate 114 (see example 38) was divided in 3 parts (each containing 0.045 mmol), then the corresponding amines (0.18 mmol) were added. The resulting solution was then heated to 60° C. overnight and evaporated; MeOH (5 ml) and MeONa (50 mg) were added, the mixture was stirred at RT for 2 hours then evaporated. Purification: reverse phase chromatography (15 g), eluting with $H_2O$—AcOH (0.1%) to $CH_3CN$—AcOH (0.1%) in gradient.

General Procedure 16:

To a solution of intermediate (VII) (intermediate 67) (1 mmol) in DMF (8 ml), CDI (2 mmol) was added. After 3 h, amine (4 mmol) was added and the resulting mixture was stirred at 50° C. for 1 h, then was loaded onto a reverse phase column (50 g) eluting with water+0.1% AcOH only to acetonitrile+0.1% AcOH only to give the title compound.

With reference to the below table 8, following the procedures above indicated (3rd column of the table) by starting from intermediates above prepared (and indicated in the 2nd column of the below table) the compounds 1-41 have been prepared:

TABLE 8

| Compound | Intermediate | Procedure | Yield |
|---|---|---|---|
| Compounds 1-41 | | | |
| 1<br>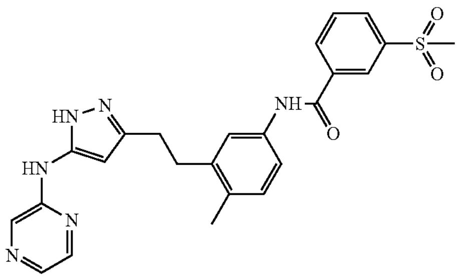 [SMILES: Cc1ccc(NC(=O)c2cccc(S(C)(=O)=O)c2)cc1CCc1cc(Nc2cnccn2)[nH]n1] | 85<br>$^1H$ NMR (400 MHz, DMSO-$d_6$) δ ppm 12.03-12.09 (1 H, m), 10.39-10.44 (1 H, m), 9.54-9.60 (1 H, m), 8.53-8.58 (1 H, m), 8.46-8.50 (1 H, m), 8.27-8.31 (1 H, m), 8.12-8.16 (1 H, m), 8.06-8.10 (1 H, m), 7.80-7.89 (2H, m), 7.61-7.64 (1 H, m), 7.54-7.58 (1 H, m), 7.14-7.19 (1 H, m), 6.25-6.30 (1 H, m), 2.80-2.95 (4 H, m),2.29 (3 H, s). CH3 under water signal ESI+ m/z 47477[M + H]+ | 12 | 71 |
| N-(4-methyl-3-(2-(5-(pyrazin-2-ylamino)-1H-pyrazol-3-yl)ethyl)phenyl)-3-(methylsulfonyl)benzamide | | | |
| 2<br>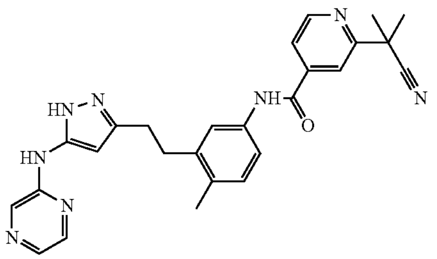 [SMILES: Cc1ccc(NC(=O)c2ccnc(C(C)(C)C#N)c2)cc1CCc1cc(Nc2cnccn2)[nH]n1] | 84<br>$^1H$ NMR (400 MHz, DMSO-$d_6$) δ ppm 12.06 (1 H, br. s.), 10.45 (1 H, s), 9.58 (1 H, br. s.), 8.80 (1 H, d, J = 4.89Hz), 8.53 (1 H, br. s.), 8.08 (1 H, dd, J = 2.93, 1.47 Hz), 8.01 (1 H, s), 7.81-7.91 (2 H, m), 7.62 (1 H, d, J = 1.96 Hz), 7.54 (1 H, d, J = 6.36 Hz), 7.18 (1 H, d, J = 8.31 Hz), 6.25 (1 H, s), 2.78-2.96 (4 H, m), 2.22-2.32 (3 H, m), 1.78 (6H, s) ESI+ m/z 467[M + H]+ | 12 | 58 |
| 2-(2-cyanopropan-2-yl)-N-(4-methyl-3-(2-(5-(pyrazin-2-ylamino)-1H-pyrazol-3-yl)ethyl)phenyl) isonicotinamide | | | |
| 3<br>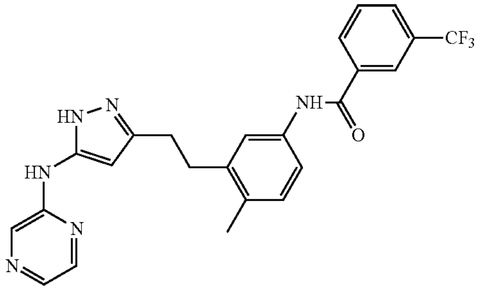 [SMILES: Cc1ccc(NC(=O)c2cccc(C(F)(F)F)c2)cc1CCc1cc(Nc2cnccn2)[nH]n1] | 82<br>$^1H$ NMR (400 MHz, DMSO-$d_6$) δ ppm 12.06 (brs, 1H), 10.36 (s, 1H), 9.57 (brs, 1H), 8.54 (brs, 1H), 8.30 (s, 1H), 8.27 (d, J = 7.8 Hz, 1H), 8.12-8.05 (m, 1H), 8.01-7.94 (m, 1H), 7.87 (d, J = 2.9 Hz, 1H), 7.82-7.75 (m, 1H), 7.64 (d, J = 2.0 Hz, 1H), 7.58-7.51 (m, 1H), 7.16 (d, J = 8.3 Hz, 1H), 6.27 (brs, 1H), 2.87 (brd, J = 12.2 Hz, 4H), 2.29 (s, 3H) ESI+ m/z 467[M + H]+ | 12 | 77 |
| N-(4-methyl-3-(2-(5-(pyrazin-2-ylamino)-1H-pyrazol-3-yl)ethyl)phenyl)-3-(trifluoromethyl)benzamide | | | |
| 4<br>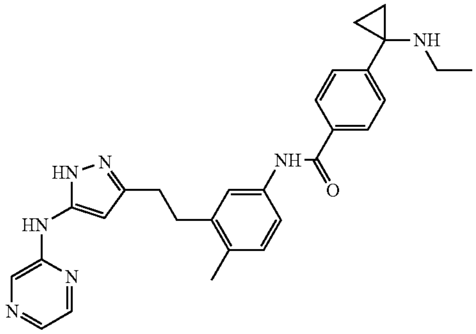 [SMILES: CCNC1(c2ccc(C(=O)Nc3ccc(C)c(CCc4cc(Nc5cnccn5)[nH]n4)c3)cc2)CC1] | 83<br>$^1H$ NMR (400 MHz, DMSO-$d_6$) δ ppm 12.17-11.95 (m, 1H), 10.03 (s, 1H), 9.70-9.46 (m, 1H), 8.64-8.44 (m, 1H), 8.16-8.03 (m, 1H), 7.90-7.83 (m, 3H), 7.70-7.64 (m, 1H), 7.55-7.49 (m, 1H), 7.44 (s, 2H), 7.16-7.09 (m, 1H), 6.34-6.17 (m, 1H), 2.93-2.79 (m, 4H), 2.49-2.43 (m, 2H), 2.27 (s, 3H), 1.04-0.90 (m, 7H). ESI+ m/z 482[M + H]+ | 12 | 66 |

TABLE 8-continued

| Compounds 1-41 | | | |
|---|---|---|---|
| Compound | Intermediate | Procedure | Yield |
| 4-(1-(ethylamino)cyclopropyl)-N-(4-methyl-3-(2-(5-(pyrazin-2-ylamino)-1H-pyrazol-3-yl)ethyl)phenyl) benzamide | | | |
| 5 | 89 | 12 | 63 |
| 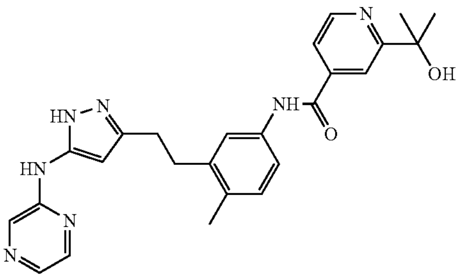 [SMILES: Cc1ccc(NC(=O)c2ccnc(C(C)(C)O)c2)cc1CCc1cc(Nc2cnccn2)[nH]n1] | $^1$H NMR (400 MHz, DMSO-$d_6$) δ ppm 11.99-12.11 (1 H, m), 10.33-10.45 (1 H, m), 9.50-9.66 (1 H,m), 8.62-8.74 (1 H, m), 8.47-8.59 (1 H, m), 8.11-8.15 (1 H, m), 8.03-8.10 (1 H, m), 7.83-7.91 (1H, m), 7.67-7.73 (1 H, m), 7.63 (1 H, s), 7.54 (1 H, s), 7.13-7.19 (1 H, m), 6.22-6.31 (1 H, m), 5.32-5.36 (1 H, m), 2.78-2.94 (4 H, m), 2.28 (3 H, s), 1.49 (6 H, s) ESI+ m/z 458[M + H]+ | | |
| 2-(2-hydroxypropan-2-yl)-N-(4-methyl-3-(2-(5-(pyrazin-2-ylamino)-1H-pyrazol-3-yl)ethyl)phenyl) isonicotinamide | | | |
| 6 | 88 | 12 | 74 |
| 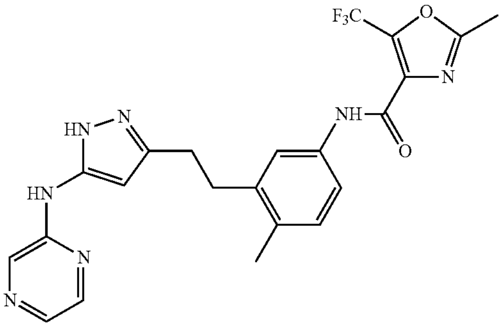 [SMILES: Cc1nc(C(=O)Nc2ccc(C)c(CCc3cc(Nc4cnccn4)[nH]n3)c2)c(C(F)(F)F)o1] | $^1$H NMR (400 MHz, DMSO-$d_6$) δ ppm 12.03 (1 H, br. s.), 10.34 (1 H, br. s.), 9.58 (1 H, br. s.), 8.53 (1 H, s), 8.08 (1 H, dd), 7.87 (1 H, d), 7.71 (1 H, d), 7.53 (1 H, dd), 7.13 (1 H, d), 6.25 (1 H, s), 2.75-2.95 (4 H, m), 2.61 (3 H, s), 2.27 (3 H, s) ESI+ m/z 472[M + H]+ | | |
| 2-methyl-N-(4-methyl-3-(2-(5-(pyrazin-2-ylamino)-1H-pyrazol-3-yl)ethyl)phenyl)-5-(trifluoromethyl) oxazole-4-carboxamide | | | |
| 7 | 87 | 12 | 85 |
| 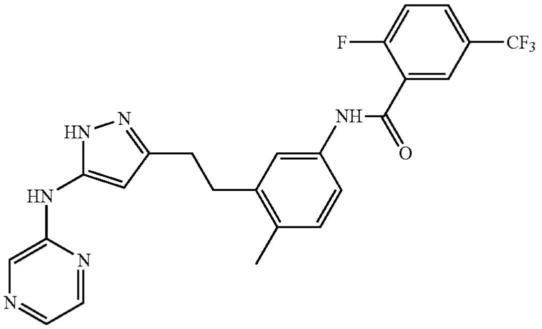 [SMILES: Cc1ccc(NC(=O)c2cc(C(F)(F)F)ccc2F)cc1CCc1cc(Nc2cnccn2)[nH]n1] | $^1$H NMR (400 MHz, DMSO-$d_6$) δ ppm 12.04 (1 H, br. s.), 10.46 (1 H, s), 9.58 (1 H, s), 8.53 (1 H, s), 7.93-8.11 (3 H, m), 7.87 (1 H, d), 7.54-7.66 (2 H, m), 7.48 (1 H, dd), 7.16 (1 H, d), 6.25 (1 H, s), 2.75-2.96 (4 H, m), 2.28 (3 H,s). ESI+ m/z 485[M + H]+ | | |

TABLE 8-continued

| Compounds 1-41 | | | |
|---|---|---|---|
| Compound | Intermediate | Procedure | Yield |
| 2-fluoro-N-(4-methyl-3-(2-(5-(pyrazin-2-ylamino)-1H-pyrazol-3-yl)ethyl)phenyl)-5-(trifluoromethyl) benzamide | | | |
| 8 | 86 | 12 | 73 |
| 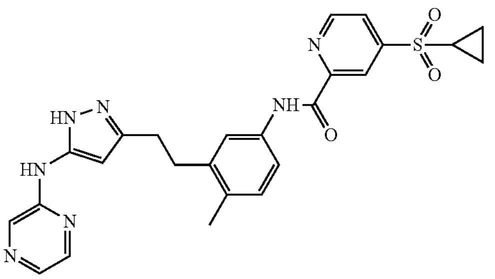 [SMILES: Cc1ccc(NC(=O)c2cc(S(=O)(=O)C3CC3)ccn2)cc1CCc1cc(Nc2cnccn2)[nH]n1] | $^{1}$H NMR (400 MHz, DMSO-$d_6$) δ ppm 12.08 (s, 1H), 10.65 (s, 1H), 9.57 (br. s, 1H), 9.15-9.01 (m, 1H), 8.60-8.51 (m, 1H), 8.49-8.45 (m, 1H), 8.19-8.13 (m, 1H), 8.12-8.04 (m, 1H), 7.91-7.83 (m, 1H), 7.81-7.75 (m, 1H), 7.73-7.65 (m, 1H), 7.23-7.14 (m, 1H),6.28 (br. s, 1H), 3.19-3.10 (m, 1H), 2.97-2.81 (m, 4H), 2.29 (s, 3H), 1.29-1.12 (m, 4H) ESI+ m/z 504[M + H]+ | | |
| 4-(cyclopropylsulfonyl)-N-(4-methyl-3-(2-(5-(pyrazin-2-ylamino)-1H-pyrazol-3-yl)ethyl)phenyl) picolinamide | | | |
| 9 | 92 | 12 | 76 |
| 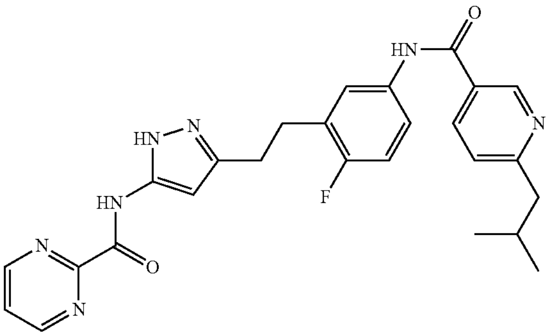 [SMILES: CC(C)Cc1ccc(C(=O)Nc2ccc(F)c(CCc3cc(NC(=O)c4ncccn4)[nH]n3)c2)cn1] | $^{1}$H NMR (400 MHz, DMSO-$d_6$) δ ppm 12.31 (1 H, br. s.), 10.54 (1 H, br. s.), 10.36 (1 H, br.s.), 9.01 (3 H, br. s.),8.19 (1 H, d, J = 6.85 Hz), 7.74 (2 H, br. s.), 7.63 (1 H, br. s.), 7.39 (1H, d, J = 8.31 Hz), 7.18 (1 H, d, J = 8.31 Hz), 6.50 (1 H, br. s.), 2.95 (4H, d, J = 8.31 Hz), 2.69 (2 H, d, J = 5.87 Hz), 2.10 (1 H, br. s.), 0.90 (6 H, d, J = 5.87 Hz) ESI+ m/z 488 [M + H]+ | | |
| N-(3-(2-fluoro-5-(6-isobutylnicotinamido)phenethyl)-1H-pyrazol-5-yl)pyrimidine-2-carboxamide | | | |
| 10 | 91 | 12 | 40 |
| 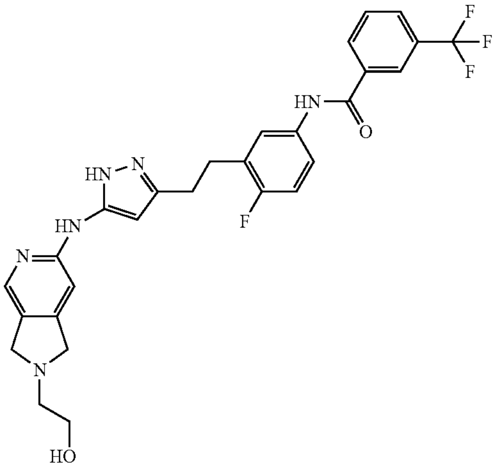 [SMILES: O=C(Nc1ccc(F)c(CCc2cc(Nc3cc4c(cn3)CN(CCO)C4)[nH]n2)c1)c1cccc(C(F)(F)F)c1] | $^{1}$H NMR (400 MHz, DMSO-$d_6$) δ ppm 11.82 (1 H, br. s.), 10.46 (1 H, s), 8.98 (1 H, br. s.), 8.21-8.34 (2 H, m), 7.89-8.04 (2 H, m), 7.72-7.83 (2 H, m), 7.66 (1 H, ddd, J = 8.93, 4.52, 2.69 Hz), 6.96-7.26 (2 H, m), 6.02 (1 H, br. s.), 4.42-4.57 (1 H, m), 3.78 (4 H, d, J = 6.36 Hz), 3.50-3.60 (2 H, m), 2.90-2.98 (2 H, m), 2.83-2.90 (2 H, m), 2.73 (2 H, t, J = 6.36 Hz). ESI+ m/z 555[M + H]+ | | |

TABLE 8-continued

| Compounds 1-41 | | | |
|---|---|---|---|
| Compound | Intermediate | Procedure | Yield |
| N-(4-fluoro-3-(2-(5-((2-(2-hydroxyethyl)-2,3-dihydro-1H-pyrrolo[3,4-c]pyridin-6-yl)amino)-1H-pyrazol-3-yl)ethyl)phenyl)-3-(trifluoro methyl) benzamide | | | |
| 11 | 96 | 12 | 45 |
| 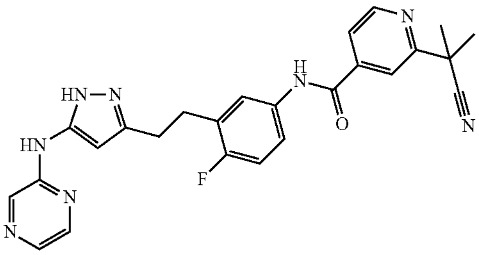 [SMILES: CC(C)(C#N)c1cc(C(=O)Nc2ccc(F)c(CCc3cc(Nc4cnccn4)[nH]n3)c2)ccn1] | $^1$H NMR (400 MHz, DMSO-$d_6$) δ ppm 11.94-12.14 (1 H, m), 10.56 (1 H, s), 9.57 (1 H, s), 8.81 (1 H, d, J = 4.89 Hz), 8.51 (1 H, s), 7.96-8.12 (2 H, m), 7.82-7.91 (2 H, m), 7.60-7.75 (2 H, m), 7.20 (1 H, t, J = 9.29 Hz), 6.22 (1H, s), 2.82-3.04 (4 H, m), 1.77 (6 H, s)<br>ESI+ m/z 471[M + H]+ | | |
| 2-(2-cyanopropan-2-yl)-N-(4-fluoro-3-(2-(5-(pyrazin-2-ylamino)-1H-pyrazol-3-yl)ethyl)phenyl) isonicotinamide | | | |
| 12 | 95 | 12 | 72 |
| 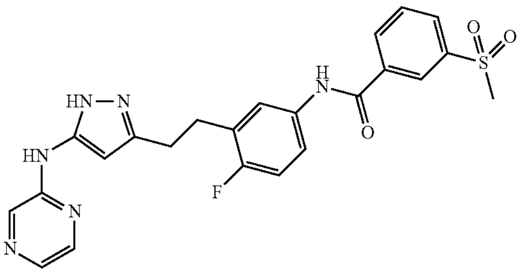 [SMILES: CS(=O)(=O)c1cccc(C(=O)Nc2ccc(F)c(CCc3cc(Nc4cnccn4)[nH]n3)c2)c1] | $^1$H NMR (400 MHz, DMSO-$d_6$) δ ppm 12.03 (1 H, s), 10.51 (1 H, s), 9.53 (1 H, s), 8.41-8.59 (2 H, m), 8.29 (1 H, s), 8.15 (1 H, d), 8.07 (1 H, s), 7.79-7.89 (2 H, m), 7.75 (1 H, dd), 7.66 (1 H, dt), 7.19 (1 H, t), 6.24 (1 H, s), 2.84-3.02 (4 H, m)<br>ESI+ m/z 481[M + H]+ | | |
| N-(4-fluoro-3-(2-(5-(pyrazin-2-ylamino)-1H-pyrazol-3-yl)ethyl)phenyl)-3-(methylsulfonyl)benzamide | | | |
| 13 | 94 | 12 | 59 |
| 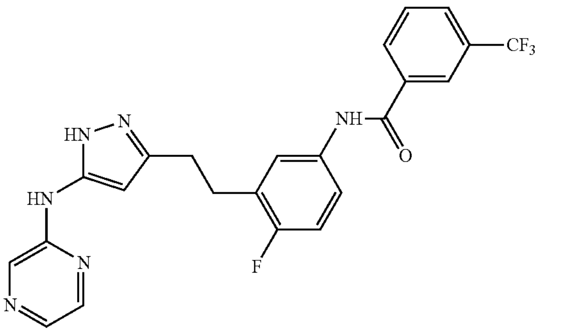 [SMILES: O=C(Nc1ccc(F)c(CCc2cc(Nc3cnccn3)[nH]n2)c1)c1cccc(C(F)(F)F)c1] | $^1$H NMR (400 MHz, DMSO-$d_6$) δ ppm 12.04 (1 H, s), 10.46 (1 H, s), 9.53 (1 H, s), 8.54 (1 H, s), 8.22-8.33 (2 H, m), 8.07 (1 H, s), 7.97 (1 H, d), 7.86 (1 H, d), 7.72-7.83 (2 H, m), 7.61-7.68 (1 H, m), 7.18 (1 H, t), 6.24 (1 H, s), 2.84-3.00 (4 H, m).<br>ESI+ m/z 471[M + H]+ | | |
| N-(4-fluoro-3-(2-(5-(pyrazin-2-ylamino)-1H-pyrazol-3-yl)ethyl)phenyl)-3-(trifluoromethyl) benzamide | | | |
| 14 | 97 | 12 | 55 |
| 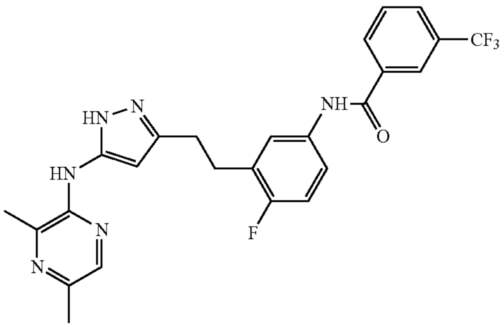 [SMILES: Cc1cnc(Nc2cc(CCc3cc(NC(=O)c4cccc(C(F)(F)F)c4)ccc3F)n[nH]2)c(C)n1] | $^1$H NMR (400 MHz, DMSO-$d_6$) δ ppm 12.00 (1 H, br. s.), 10.46 (1 H, s), 8.36-8.54 (1 H, m), 8.23-8.31 (2 H, m), 7.98 (1 H, d, J = 7.83 Hz), 7.73-7.84 (3 H, m), 7.65 (1 H, ddd, J = 8.80, 4.40, 2.93 Hz), 7.18 (1 H, t, J = 9.29 Hz), 6.20-6.38 (1 H, m), 2.83-3.00 (4 H, m), 2.42 (3 H, s), 2.28 (3 H,s)<br>ESI+ m/z 499 [M + H]+ | | |

TABLE 8-continued

| Compounds 1-41 | | | |
|---|---|---|---|
| Compound | Intermediate | Procedure | Yield |
| N-(3-(2-(5-((3,5-dimethylpyrazin-2-yl)amino)-1H-pyrazol-3-yl)ethyl)-4-fluorophenyl)-3-(trifluoromethyl)benzamide | | | |
| 15 | 98 | 12 | 62 |
| 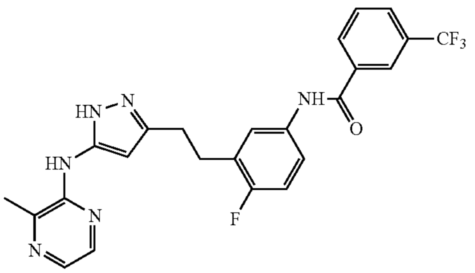 [SMILES: Cc1nccnc1Nc1cc(CCc2cc(NC(=O)c3cccc(C(F)(F)F)c3)ccc2F)n[nH]1] | $^1$H NMR (400 MHz, DMSO-$d_6$) δ ppm 11.91-12.23 (1 H, m), 10.47 (1 H, s), 8.63 (1 H, br. s.), 8.19-8.33 (2 H, m), 7.91-8.02 (2 H, m), 7.71-7.84 (3 H, m), 7.65 (1 H, dt, J = 8.07, 3.79 Hz), 7.18 (1 H, t, J = 9.29 Hz), 6.36 (1 H, br. s.), 2.83-3.02 (4 H, m), 2.46 (3 H, s). ESI+ m/z 485 [M + H]+ | | |
| N-(4-fluoro-3-(2-(5-((3-methylpyrazin-2-yl)amino)-1H-pyrazol-3-yl)ethyl)phenyl)-3-(trifluoromethyl) benzamide | | | |
| 16 | 99 | 12 | 51 |
| 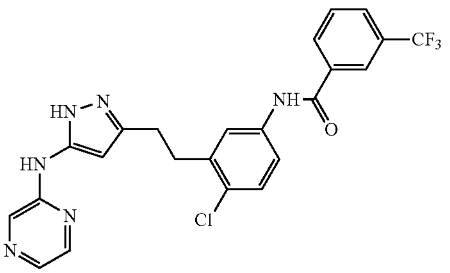 [SMILES: O=C(Nc1ccc(Cl)c(CCc2cc(Nc3cnccn3)[nH]n2)c1)c1cccc(C(F)(F)F)c1] | $^1$H NMR (400 MHz, DMSO-$d_6$) δ ppm 12.06 (1 H, br. s.), 10.54 (1 H, s), 9.59 (1 H, s), 8.52 (1 H, s), 8.24-8.31 (2 H, m), 8.08 (1 H, dd, J = 2.45, 1.47 Hz), 7.98 (1 H, d, J = 7.83 Hz), 7.76-7.88 (3 H, m), 7.71 (1 H, dd, J = 8.56, 2.69 Hz), 7.45 (1 H, d, J = 8.31 Hz), 6.25 (1 H, s), 3.00-3.08 (2 H, m), 2.85-2.93 (2 H, m). ESI+ m/z 487 [M + H]+ | | |
| N-(4-chloro-3-(2-(5-(pyrazin-2-ylamino)-1H-pyrazol-3-yl)ethyl)phenyl)-3-(trifluoromethyl)benzamide | | | |
| 17 | 93 | 12 | 60 |
| 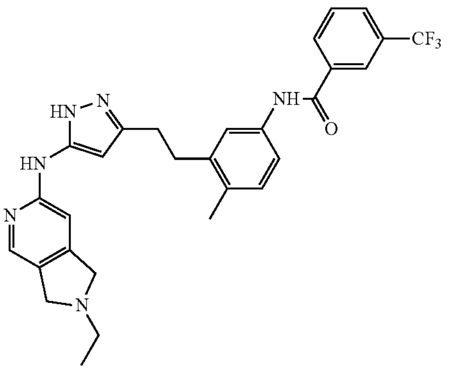 [SMILES: CCN1Cc2cnc(Nc3cc(CCc4cc(NC(=O)c5cccc(C(F)(F)F)c5)ccc4C)n[nH]3)cc2C1] | $^1$H NMR (400MHz, DMSO-$d_6$) δ ppm 12.26 (br. s., 1H), 10.36 (s, 1H), 8.99 (s, 1H), 8.33-8.24 (m, 2H), 8.17 (s, 1H), 7.99-7.93 (m, 2H), 7.81-7.76 (m, 1H), 7.64 (d, J = 2.0 Hz, 1H), 7.56 (dd, J = 2.2, 8.1 Hz, 1H), 7.18-7.11 (m, 2H), 6.06 (s, 1H), 3.75 (d, J = 7.8 Hz, 4H), 2.93-2.77 (m, 4H), 2.68 (q, J = 7.3 Hz, 2H), 2.28 (s, 3H), 1.10 (t, J = 7.1 Hz, 3H). ESI+ m/z 535 [M + H]+ | | |

TABLE 8-continued

| Compounds 1-41 | | | |
|---|---|---|---|
| Compound | Intermediate | Procedure | Yield |
| N-(3-(2-(5-((2-ethyl-2,3-dihydro-1H-pyrrolo[3,4-c]pyridin-6-yl)amino)-1H-pyrazol-3-yl)ethyl)-4-methylphenyl) -3-(trifluoromethyl)benzamide | | | |
| 18 | 106 | 12 | 21 |
| 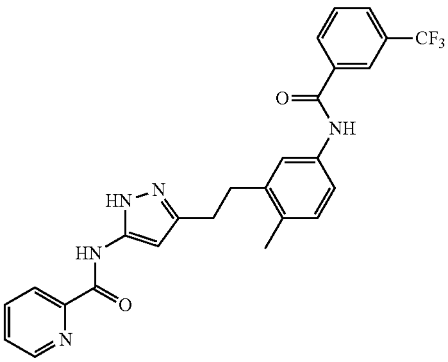 [SMILES: Cc1ccc(NC(=O)c2cccc(C(F)(F)F)c2)cc1CCc1cc(NC(=O)c2ccccn2)[nH]n1] | $^1$H NMR (400 MHz, DMSO-$d_6$) 6 ppm 12.37 (1 H, br. s.), 10.37 (1 H, s), 10.28 (1 H, br. s.), 8.72 (1 H, d), 8.30 (1 H, s), 8.27 (1 H, d), 8.12-8.18 (1 H, m), 8.05-8.11 (1 H, m), 7.96 (1 H, d), 7.79 (1 H, t),7.66-7.71 (1 H, m), 7.64 (1 H, d), 7.57 (1 H, dd), 7.17 (1 H, d), 6.55 (1 H, br. s.), 2.90 (4 H, d), 2.29 (3H, s)<br>ESI+ m/z 494 [M + H]+ | | |
| N-(5-(2-methyl-5-(3-(trifluoromethyl)benzamido)phenethyl)-1H-pyrazol-3-yl)picolinamide | | | |
| 19 | 107 | 12 | 30 |
| 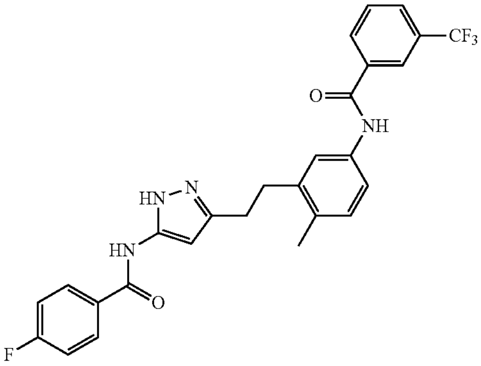 [SMILES: Cc1ccc(NC(=O)c2cccc(C(F)(F)F)c2)cc1CCc1cc(NC(=O)c2ccc(F)cc2)[nH]n1] | $^1$H NMR (400 MHz, DMSO-$d_6$) δ ppm 12.30 (1 H, s), 10.80 (1 H, s), 10.37 (1 H, s), 8.22-8.35 (2 H, m), 7.95 (1 H, s), 7.85 (1 H, d), 7.76-7.83 (2 H, m), 7.64 (1 H, d), 7.56 (2 H, dd), 7.37-7.46 (1 H, m), 7.17 (1 H, d), 6.52 (1 H, s), 2.81-2.97 (4 H, m), 2.30 (3 H, s)<br>ESI+ m/z 511 [M + H]+ | | |
| N-(3-(2-(3-(4-fluorobenzamido)-1H-pyrazol-5-yl)ethyl)-4-methylphenyl)-3-(trifluoromethyl)benzamide | | | |
| 20 | 102 | 12 | 86 |
| 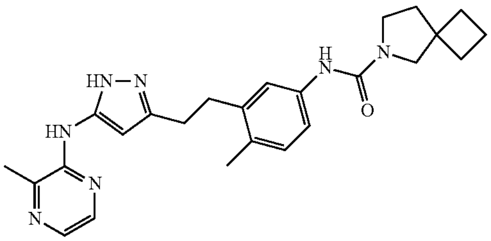 [SMILES: Cc1ccc(NC(=O)N2CCC3(CCC3)C2)cc1CCc1cc(Nc2nccnc2C)[nH]n1] | $^1$H NMR (400 MHz, DMSO-$d_6$) δ ppm 12.04 (s, 1H), 8.52 (brs, 1H), 8.00-7.90 (m, 2H), 7.79 (brs, 1H), 7.42-7.35 (m, 1H), 7.29-7.22 (m, 1H), 6.99 (d, J = 1.0 Hz, 1H), 6.45 (br s, 1H), 3.39-3.33 (m, 4H), 2.88-2.73 (m, 4H), 2.47 (s, 3H), 2.22 (s, 3H), 2.02-1.83 (m, 8H)<br>ESI+ m/z 446 [M + H]+ | | |
| N-(4-methyl-3-(2-(5-((3-methylpyrazin-2-yl)amino)-1H-pyrazol-3-yl)ethyl)phenyl)-6-azaspiro[3.4] octane-6-carboxamide | | | |
| 21 | 101 | 12 | 68 |
| 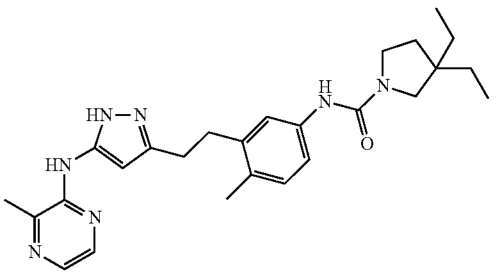 [SMILES: CCC1(CC)CCN(C(=O)Nc2ccc(C)c(CCc3cc(Nc4nccnc4C)[nH]n3)c2)C1] | $^1$H NMR (400 MHz, DMSO-$d_6$) δ ppm 12.03 (s, 1 H), 8.53 (s, 1 H), 7.99-7.87 (m, 2H), 7.78 (br s, 1H), 7.38 (d, J = 1.0 Hz, 1H), 7.27 (t, J = 1.0 Hz, 1H), 7.01 (d, J = 1.0 Hz, 1H), 6.46 (br s, 1H), 3.44-3.36 (m, 2H), 3.19-3.09 (m, 2H), 2.81 (brs, 4H), 2.47 (s, 3H), 2.23 (s, 3H), 1.75-1.63 (m, 2H), 1.46-1.32 (m, 4H), 0.91-0.78 (m, 6H)<br>ESI+ m/z 462 [M + H]+ | | |

TABLE 8-continued

| Compounds 1-41 | | | |
|---|---|---|---|
| Compound | Intermediate | Procedure | Yield |
| 3,3-diethyl-N-(4-methyl-3-(2-(5-((3-methylpyrazin-2-yl)amino)-1H-pyrazol-3-yl)ethyl)phenyl) pyrrolidine-1-carboxamide | | | |
| 22 | 100 | 12 | 32 |
| 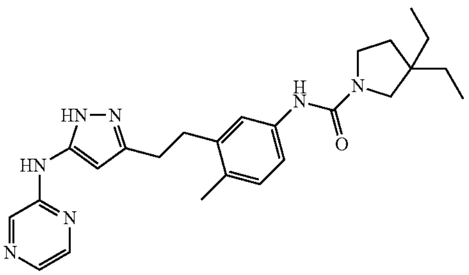 [SMILES: CCC1(CC)CCN(C(=O)Nc2ccc(C)c(CCc3cc(Nc4cnccn4)[nH]n3)c2)C1] | $^1$H NMR (400 MHz, DMSO-$d_6$) δ ppm 12.02 (1 H, br. s.), 9.58 (1 H, s), 8.53 (1 H, d), 8.08 (1 H, dd), 7.91 (1 H, s), 7.87 (1 H, d), 7.37 (1 H, d), 7.27 (1 H, dd), 6.99 (1 H, d), 6.24 (1 H, s), 3.40 (2 H, t), 3.15 (2 H, s), 2.74-2.87 (4 H, m), 2.21 (3 H, s), 1.67 (2 H, t), 1.33-1.43 (4 H, m), 0.83 (6 H, t) ESI+ m/z [M + H]+ | | |
| 3,3-diethyl-N-(4-methyl-3-(2-(5-(pyrazin-2-ylamino)-1H-pyrazol-3-yl)ethyl)phenyl)pyrrolidine-1-carboxamide | | | |
| 23 | 103 | 12 | 35 |
| 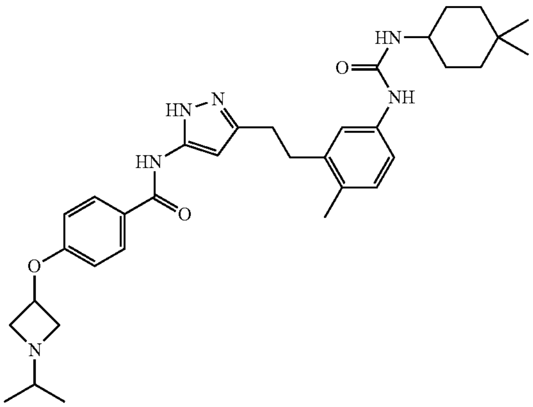 [SMILES: Cc1ccc(NC(=O)NC2CCC(C)(C)CC2)cc1CCc1cc(NC(=O)c2ccc(OC3CN(C(C)C)C3)cc2)[nH]n1] | $^1$H NMR (400 MHz, DMSO-$d_6$) δ ppm 12.18 (1 H, br. s.), 10.52 (1 H, br. s.), 8.13 (1 H, s), 7.97 (2 H, d), 7.21 (1 H, d), 7.13 (1 H, dd), 6.99 (1 H, d), 6.91 (2 H, d), 6.46 (1 H, br. s.), 6.00 (1 H, d), 4.81 (1 H, quin), 3.72 (2 H, m), 3.36-3.48 (1 H, m), 2.94 (2 H, dd), 2.74-2.88 (4 H, m), 2.28-2.37 (1 H, m), 2.21 (3 H, s), 1.62-1.73 (2 H, m), 1.34 (6 H, br. s.), 0.85-0.94 (12 H, m) ESI+ m/z 587 [M + H]+ | | |
| N-(3-(5-(3-(4,4-dimethylcyclohexyl)ureido)-2-methylphenethyl)-1H-pyrazol-5-yl)-4-((1-isopropylazetidin-3-yl)oxy)benzamide | | | |
| 24 | 105 | 12 | 27 |
| 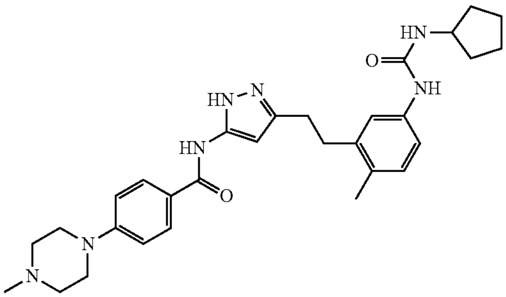 [SMILES: Cc1ccc(NC(=O)NC2CCCC2)cc1CCc1cc(NC(=O)c2ccc(N3CCN(C)CC3)cc2)[nH]n1] | $^1$H NMR (400 MHz, DMSO-$d_6$) δ ppm 12.14 (1 H, br. s.), 10.32 (1 H, br. s.), 8.07 (1 H, s), 7.90 (2 H, d), 7.20 (1 H, d), 7.13 (1 H, dd), 6.93-7.02 (3 H, m), 6.47 (1 H, br. s.), 6.06 (1 H, d), 3.87-3.97 (1 H, m), 3.28 (4 H, s), 2.73-2.89 (4 H, m), 2.41-2.48 (4 H, m), 2.23 (3 H, s), 2.21 (3 H, s), 1.78-1.89 (2 H, m), 1.46-1.69 (4 H, m), 1.30-1.41 (2 H, m) ESI+ m/z 530 [M + H]+ | | |

TABLE 8-continued

| Compound | Intermediate | Procedure | Yield |
|---|---|---|---|
| Compounds 1-41 | | | |
| N-(3-(5-(3-cyclopentylureido)-2-methylphenethyl)-1H-pyrazol-5-yl)-4-(4-methylpiperazin-1-yl) benzamide | | | |
| 25 | 104 | 12 | 40 |
| 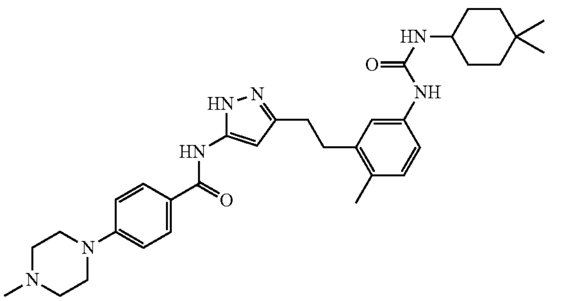 | $^1H$ NMR (400 MHz, DMSO-$d_6$) δ ppm 12.17 (br. s, 1H), 10.59 (br. s., 1H), 8.13 (s, 1 H), 7.93 (d, J = 8.3 Hz, 2H), 7.35 (d, J = 8.3 Hz, 2H), 7.21 (d, J = 2.0 Hz, 1H), 7.16-7.09 (m, 1H), 6.99 (d, J = 8.3 Hz, 1H), 6.46 (br. s, 1H), 6.01 (d, J = 7.3 Hz, 1H), 3.46-3.39 (m, 1H), 2.90-2.84 (m, 2H), 2.84-2.74 (m, 4H), 2.21 (d, J = 2.0 Hz, 6H), 2.02-1.91 (m, 2H), 1.81-1.61 (m, 6H), 1.37-1.18 (m, 6H), 0.91 (d, J = 2.0 Hz, 6H). ESI+ m/z 571 [M + H]+ | | |
| N-(3-(5-(3-(4,4-dimethylcyclohexyl)ureido)-2-methylphenethyl)-1H-pyrazol-5-yl)-4-(1-methylpipe ridin-4-yl)benzamide | | | |
| 26 | 111 | 15 | 29 |
| 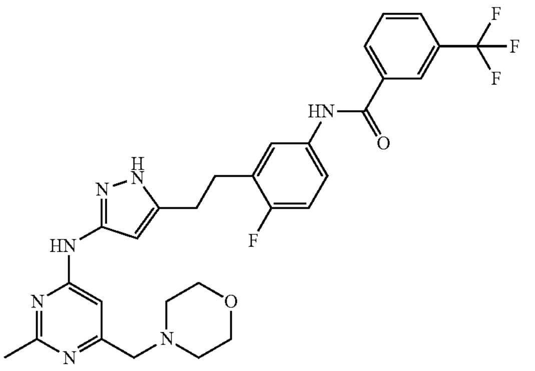 [SMILES: Cc1nc(CN2CCOCC2)cc(Nc2cc(CCc3cc(NC(=O)c4cccc(C(F)(F)F)c4)ccc3F)[nH]n2)n1] | $^1H$ NMR (400 MHz DMSO-$d_6$) δ ppm 12.21 (br. s., 1 H), 10.62 (s, 1 H), 9.72 (br. s., 1 H), 8.41-8.20 (m, 2 H), 7.97 (d, J = 7.8 Hz, 1 H), 7.87-7.75 (m, 2 H), 7.74-7.66 (m, 1 H), 7.33-6.96 (m, 2 H), 6.14 (br. s., 1 H), 3.62 (d, J = 8.8 Hz, 4 H), 3.43 (br. s., 2 H), 2.99-2.84 (m, 4 H), 2.48 (br. s., 4 H), 2.39 (s, 3 H) ESI+ m/z 584 [M + H]+ | | |
| N-(4-fluoro-3-(2-(3-((2-methyl-6-(morpholinomethyl)pyrimidin-4-yl)amino)-1H-pyrazol-5-yl)ethyl) phenyl)-3-(trifluoromethyl)benzamide | | | |
| 27 | 111 | 15 | 33 |
| 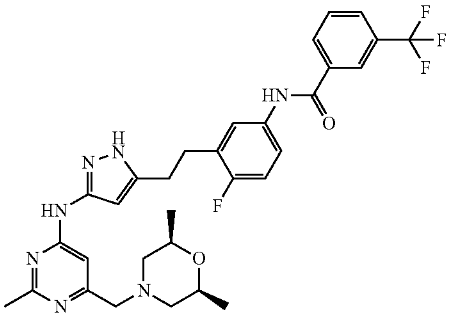 [SMILES: Cc1nc(CN2C[C@@H](C)O[C@@H](C)C2)cc(Nc2cc(CCc3cc(NC(=O)c4cccc(C(F)(F)F)c4)ccc3F)[nH]n2)n1] | $^1H$ NMR (400 MHz, DMSO-$d_6$) δ ppm 12.03 (1 H, br. s.), 10.46 (1 H, s), 9.58 (1 H, br. s.), 8.21-8.34 (2H, m), 7.97 (1 H, d), 7.72-7.85 (2 H, m), 7.65 (1 H, dt), 7.18 (2 H, t), 6.14 (1 H, br. s.), 3.53-3.66 (2H, m), 2.85-3.00 (4 H, m), 2.73 (2 H, s), 2.38 (3 H, s), 1.72 (2 H, t), 0.99-1.08 (6 H, m) ESI+ m/z 612 [M + H]+ | | |

TABLE 8-continued

| Compounds 1-41 | | | |
|---|---|---|---|
| Compound | Intermediate | Procedure | Yield |
| N-(3-(2-(3-((6-(((2S,6R)-2,6-dimethylmorpholino)methyl)-2-methylpyrimidin-4-yl)amino)-1H-pyrazol-5-yl)ethyl)-4-fluorophenyl)-3-(trifluoromethyl)benzamide | | | |
| 28 | 111 | 15 | 40 |
| 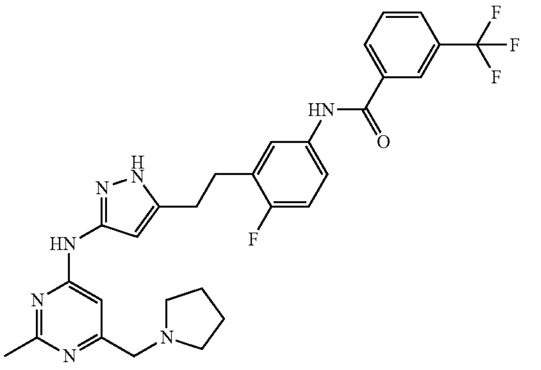 [SMILES: Cc1nc(CN2CCCC2)cc(Nc2cc(CCc3cc(NC(=O)c4cccc(C(F)(F)F)c4)ccc3F)[nH]n2)n1] | $^1$H NMR (400 MHz, DMSO-$d_6$) δ ppm 11.99 (1 H, br. s.), 10.46 (1 H, s), 9.48-9.67 (1 H, m), 8.19-8.35 (2 H, m), 7.97 (1 H, d), 7.71-7.84 (2 H, m), 7.66 (1 H, ddd), 6.94-7.24 (2 H, m), 6.13 (1 H, br. s.), 3.49 (2 H, s), 2.82-3.04 (4 H, m), 2.34 (3 H, d), 1.92 (3 H, s), 1.60-1.78 (4 H, m)<br>ESI+ m/z 568 [M + H]+ | | |
| N-(4-fluoro-3-(2-(3-((2-methyl-6-(pyrrolidin-1-ylmethyl)pyrimidin-4-yl)amino)-1H-pyrazol-5-yl)ethyl)phenyl)-3-(trifluoromethyl)benzamide | | | |
| 29 | 112 | 14 | 68 |
| 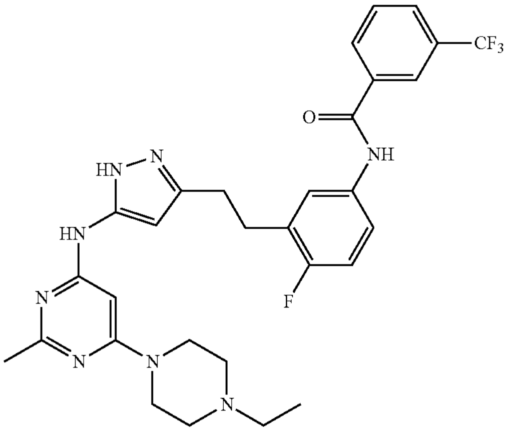 | $^1$H NMR (400 MHz, DMSO-$d_6$) δ ppm 11.93 (1 H, br. s.), 10.46 (1 H, s), 9.07 (1 H, s), 8.19-8.34 (2 H, m), 7.97 (1 H, d), 7.59-7.86 (3 H, m), 7.18 (1 H, t), 6.54 (1 H, br. s.), 5.91 (1 H, s), 3.41-3.52 (4 H, m), 2.80-3.01 (4 H, m), 2.29-2.45 (6 H, m), 2.25 (3 H, s), 1.03 (3 H, t)<br>ESI+ m/z 657 [M + H]+ | | |
| N-(3-(2-(3-((6-(4-ethylpiperazin-1-yl)-2-methylpyrimidin-4-yl)amino)-1H-pyrazol-5-yl)ethyl)-4-fluorophenyl)-3-(trifluoromethyl) benzamide | | | |
| 30 | 112 | 14 | 76 |
| 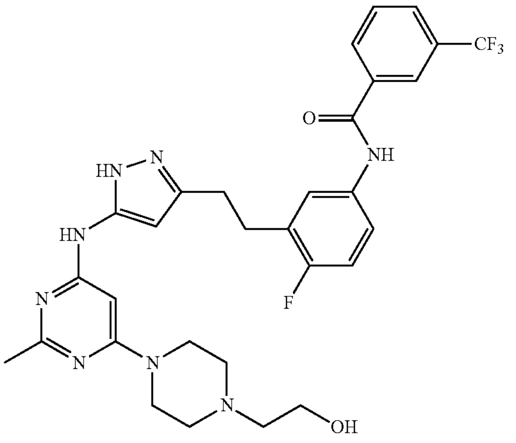 | $^1$H NMR (400 MHz, DMSO-$d_6$) δ ppm 11.91 (1 H, br. s.), 10.46 (1 H, s), 9.07 (1 H, s), 8.20-8.35 (2 H, m), 7.97 (1 H, d), 7.58-7.86 (3 H, m), 7.18 (1 H, t), 6.53 (1 H, br. s.), 5.92 (1 H, s), 4.38 (1 H, br. s.), 3.53 (2 H, t), 3.43-3.48 (4 H, m), 2.82-2.98 (4 H, m), 2.39-2.49 (6 H, m), 2.25 (3 H, s)<br>ESI+ m/z 673 [M + H]+ | | |

TABLE 8-continued

Compounds 1-41

| Compound | Intermediate | Procedure | Yield |
|---|---|---|---|
| N-(4-fluoro-3-(2-(3-((6-(4-(2-hydroxyethyl)piperazin-1-yl)-2-methylpyrimidin-4-yl)amino)-1H-pyrazol-5-yl)ethyl)phenyl)-3-(trifluoromethyl) benzamide | | | |
| 31 | 112 | 14 | 83 |
| 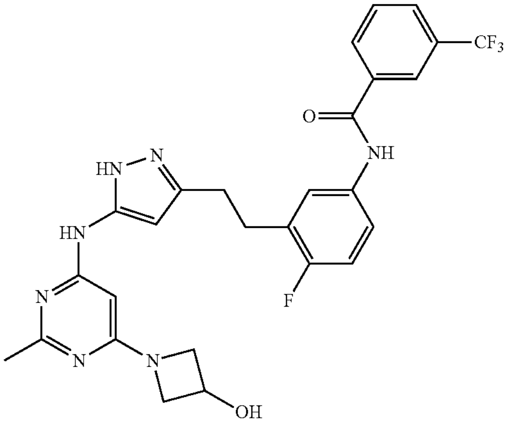 | $^1$H NMR (400 MHz, DMSO-$d_6$) δ ppm 11.89 (1 H, br. s.), 10.46 (1 H, s), 9.05 (1 H, s), 8.19-8.34 (2 H, m), 7.97 (1 H, d), 7.55-7.84 (3 H, m), 7.18 (1 H, t), 6.14 (1 H, br. s.), 5.89 (1 H, s), 5.64 (1 H, br. s.), 4.48-4.61 (1 H, m), 4.04-4.19 (2 H, m), 3.64 (2 H, dd), 2.79-3.00 (4 H, m), 2.23 (3 H,s) ESI+ m/z 616 [M + H]+ | | |
| N-(4-fluoro-3-(2-(3-((6-(3-hydroxyazetidin-1-yl)-2-methylpyrimidin-4-yl)amino)-1H-pyrazol-5-yl) ethyl) phenyl)-3-(trifluoromethyl)benzamide | | | |
| 32 | 112 | 14 | 78 |
| 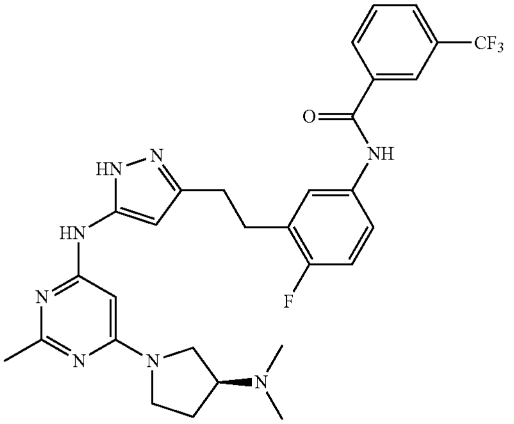 [SMILES: Cc1nc(Nc2cc(CCc3cc(NC(=O)c4cccc(C(F)(F)F)c4)ccc3F)n[nH]2)cc(N2CC[C@H](N(C)C)C2)n1] | $^1$H NMR (400 MHz, DMSO-$d_6$) δ ppm 11.89 (1 H, br. s.), 10.45 (1 H, s), 8.97 (1 H, s), 8.20-8.33 (2 H, m), 7.97 (1 H, d), 7.58-7.85 (3 H, m), 7.18 (1 H, t), 6.23 (1 H, br. s.), 5.90 (1 H, s), 3.65 (1 H, br. s.), 3.50 (1 H, br. s.), 3.02-3.09 (1 H, m), 2.82-2.98 (4 H, m), 2.73 (1 H, br. s.), 2.24 (3 H,s), 2.19 (5 H, s), 2.07-2.15 (1 H, m), 1.71-1.83 (1 H, m) ESI+ m/z 597 [M + H]+ | | |
| (S)-N-(3-(2-(3-((6-(3-(dimethylamino)pyrrolidin-1-yl)-2-methylpyrimidin-4-yl)amino)-1H-pyrazol-5-yl)ethyl)-4-fluorophenyl)-3-(trifluoromethyl)benzamide | | | |
| 33 | 90 | 12 | 57 |
| 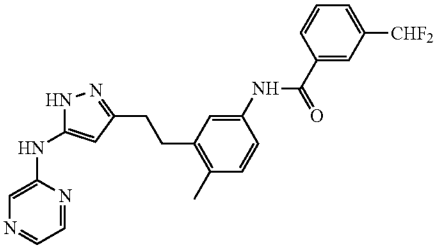 [SMILES: Cc1ccc(NC(=O)c2cccc(C(F)F)c2)cc1CCc1cc(Nc2cnccn2)[nH]n1] | $^1$H NMR (400 MHz, DMSO-$d_6$) δ ppm 11.99-12.13 (1 H, m), 10.25-10.32 (1 H, m), 9.52-9.61 (1 H, m), 8.51-8.59 (1 H, m), 8.05-8.19 (3 H, m), 7.84-7.91 (1 H, m), 7.76-7.81 (1 H, m), 7.66-7.73 (1H, m), 7.62-7.66 (1 H, m), 7.52-7.58 (1 H, m), 7.15 (2 H, s), 6.23-6.34 (1 H, m), 2.78-2.95 (4 H, m), 2.28 (3 H, s) ESI+ m/z 449 [M + H]+ | | |

TABLE 8-continued

Compounds 1-41

| Compound | Intermediate | Procedure | Yield |
|---|---|---|---|
| 3-(difluoromethyl)-N-(4-methyl-3-(2-(5-(pyrazin-2-ylamino)-1H-pyrazol-3-yl)ethyl)phenyl) benzamide | | | |
| 34 | 66 | 13 | 20 |
| 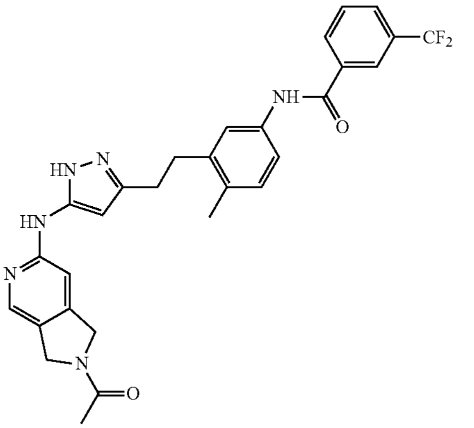 | $^1$H NMR (400 MHz, DMSO-$d_6$) δ ppm 11.88 (br.s., 1H), 10.36 (s, 1H), 9.07 (br. s., 1H), 8.33-8.22 (m, 2H), 8.09 (d, J = 3.9 Hz, 1H), 7.96 (d, J = 7.8 Hz, 1H), 7.79 (t, J = 7.8 Hz, 1H), 7.64 (s, 1H), 7.55 (dd, J = 2.0, 8.3 Hz, 1H), 7.33 (br. s., 1H), 7.16 (d, J = 8.3 Hz, 1H), 6.09 (br. s., 1H), 4.75 (d, J = 18.6 Hz, 2H), 4.53 (d, J = 12.2 Hz, 2H), 2.94-2.75 (m, 4H), 2.28 (s, 3H), 2.08-2.02 (m, 3H) ESI+ m/z 549 [M + H]+ | | |
| N-(3-(2-(5-((2-acetyl-2,3-dihydro-1H-pyrrolo[3,4-c]pyridin-6-yl)amino)-1H-pyrazol-3-yl)ethyl)-4-methylphenyl)-3-(trifluoromethyl) benzamide | | | |
| 35 | 65 | 13 | 29 |
| 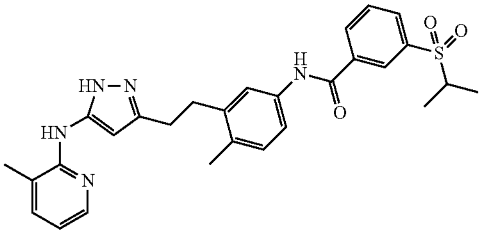 [SMILES: Cc1ccc(NC(=O)c2cccc(S(=O)(=O)C(C)C)c2)cc1CCc1cc(Nc2ncccc2C)[nH]n1] | $^1$H NMR (400 MHz, DMSO-$d_6$) δ ppm 12.07 (1 H, br. s.), 10.41 (1 H, s), 8.42 (1 H, s), 8.29-8.36 (1 H, m), 8.04-8.09 (1 H, m), 7.96-8.02 (1 H, m), 7.84 (1 H, t), 7.61-7.65 (1 H, m), 7.52-7.59 (1 H, m), 7.35-7.43 (1 H, m), 7.16 (1 H, d), 6.62-6.72 (1 H, m), 6.19-6.47 (1 H, m), 3.46-3.58 (1 H, m), 2.86-2.95 (2 H, m), 2.78-2.85 (2 H, m), 2.30 (3 H, s), 2.22 (3 H, s), 1.20 (6 H, d) ESI+ m/z 518 [M + H]+ | | |
| 3-(isopropylsulfonyl)-N-(4-methyl-3-(2-(5-((3-methylpyridin-2-yl)amino)-1H-pyrazol-3-yl)ethyl) phenyl) benzamide | | | |
| 36 | 65 | 13 | 31 |
| 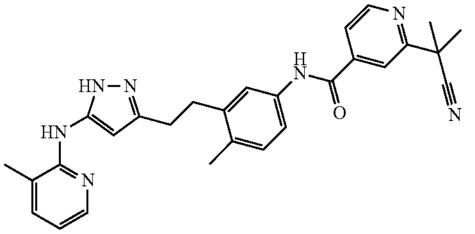 [SMILES: Cc1ccc(NC(=O)c2ccnc(C(C)(C)C#N)c2)cc1CCc1cc(Nc2ncccc2C)[nH]n1] | $^1$H NMR (400 MHz, DMSO-$d_6$) δ ppm 11.89 (1 H, br. s.), 10.45 (1 H, br. s.), 8.80 (1 H, d), 8.05-8.33 (1 H, m), 7.95-8.03 (2 H, m), 7.83-7.90 (1 H, m), 7.59-7.63 (1 H, m), 7.51-7.57 (1 H, m), 7.38 (1 H, d), 7.17 (1 H, d), 6.66 (1 H, dd), 6.29 (1 H, br. s.), 2.86-2.95 (2 H, m), 2.77-2.85 (2 H, m), 2.30 (3 H, s), 2.21 (3 H, s), 1.78 (6 H, s) ESI+ m/z 480 [M + H]+ | | |
| 2-(2-cyanopropan-2-yl)-N-(4-methyl-3-(2-(5-((3-methylpyridin-2-yl)amino)-1H-pyrazol-3-yl)ethyl) phenyl)isonicotinamide | | | |
| 37 | 64 | 13 | 66 |
| 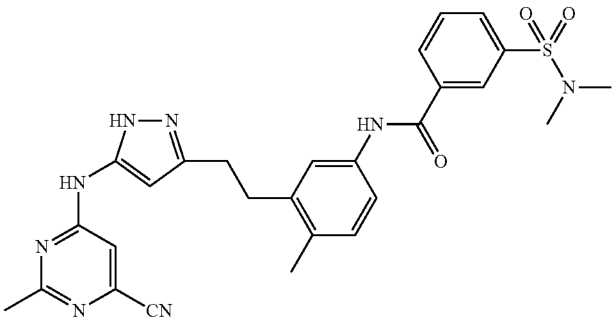 | $^1$H NMR (400 MHz, DMSO-$d_6$) δ ppm 12.32 (1 H, br. s), 10.42 (2 H, br. s), 8.26-8.33 (2 H, m), 7.95 (1 H, d), 7.82 (1 H, t), 7.62-7.66 (1 H, m), 7.51-7.57 (1 H, m), 7.16 (1 H, d), 2.80-2.96 (4 H, m), 2.67 (6 H, s), 2.46 (3 H, s), 2.28 (3 H, s) ESI+ m/z 545 [M + H]+ | | |

TABLE 8-continued

| Compounds 1-41 | | | |
|---|---|---|---|
| Compound | Intermediate | Procedure | Yield |
| N-(3-(2-(5-((6-cyano-2-methylpyrimidin-4-yl)amino)-1H-pyrazol-3-yl)ethyl)-4-methylphenyl)-3-(N,N-dimethylsulfamoyl)benzamide | | | |
| 38 | 64 | 16 | 40 |
| 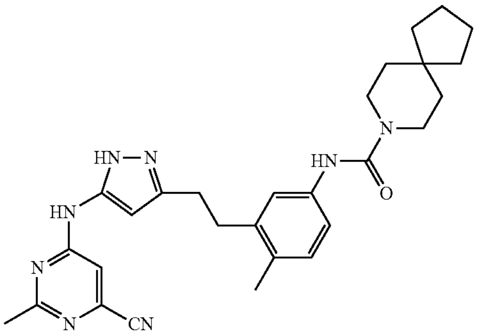 [SMILES: Cc1nc(C#N)cc(Nc2cc(CCc3cc(NC(=O)N4CCC5(CCCC5)CC4)ccc3C)n[nH]2)n1] | $^1H$ NMR (400 MHz, DMSO-$d_6$) δ ppm 12.29 (1 H, br. s.), 10.41 (1 H, br. s.), 8.28 (1 H, s), 7.32 (1 H, d), 7.21 (1 H, dd), 6.99 (1 H, d), 3.35-3.43 (4 H, m), 2.81 (4 H, s), 2.46 (3 H, s), 2.21 (3 H, s), 1.54-1.65 (4 H, m), 1.32-1.48 (8 H, m) ESI+ m/z 499 [M + H]+ | | |
| N-(3-(2-(5-((6-cyano-2-methylpyrimidin-4-yl)amino)-1H-pyrazol-3-yl)ethyl)-4-methylphenyl)-8-azaspiro [4.5] decane-8-carboxamide | | | |
| 39 | 64 | 13 | 36 |
| 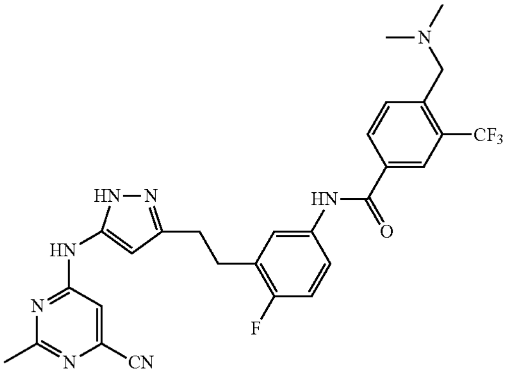 [SMILES: Cc1nc(C#N)cc(Nc2cc(CCc3cc(NC(=O)c4ccc(CN(C)C)c(C(F)(F)F)c4)ccc3F)n[nH]2)n1] | $^1H$ NMR (400 MHz, DMSO-$d_6$) δ ppm 12.18 (1 H, br. s.), 10.34 (1 H, s), 10.21 (1 H, s), 8.18-8.33 (2 H,m), 7.94 (1 H, d), 7.73 (1 H, dd), 7.60-7.69 (1 H, m), 7.46 (1 H, br. s.), 7.16 (1 H, t), 6.19 (1 H, br. s.), 3.79 (2 H, br. s.), 2.88-3.04 (4 H, m), 2.05-2.48 (8 H, m, under the solvent peak). ESI+ m/z 567 [M + H]+ | | |
| N-(3-(2-(5-((6-cyano-2-methylpyrimidin-4-yl)amino)-1H-pyrazol-3-yl)ethyl)-4-fluorophenyl)-4-((dimethylamino) methyl)-3-(trifluoromethyl)benzamide | | | |
| 40 | 74 | 13 | 51 |
| 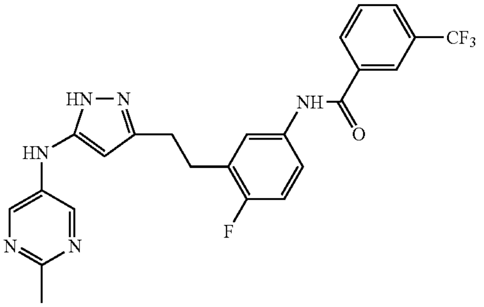 [SMILES: Cc1ncc(Nc2cc(CCc3cc(NC(=O)c4cccc(C(F)(F)F)c4)ccc3F)n[nH]2)cn1] | $^1H$ NMR (400 MHz, DMSO-$d_6$) δ ppm 11.97-11.88 (m, 1H), 10.54-10.37 (m, 1H), 8.73 (s, 2H), 8.65-8.52 (m, 1H), 8.34-8.18 (m, 2H), 8.03-7.89 (m, 1H), 7.84-7.70 (m, 2H), 7.68-7.58 (m, 1H), 7.25-7.11 (m, 1H), 5.64 (s, 1H), 3.01-2.83 (m, 4H), 2.47 (s, 3H) ESI+ m/z 485 [M + H]+ | | |

TABLE 8-continued

| Compounds 1-41 | | | |
|---|---|---|---|
| Compound | Intermediate | Procedure | Yield |
| N-(4-fluoro-3-(2-(5-((2-methylpyrimidin-5-yl)amino)-1H-pyrazol-3-yl)ethyl)phenyl)-3-(trifluoro methyl) benzamide | | | |
| 41 | 108 | 12 | 95 |
| 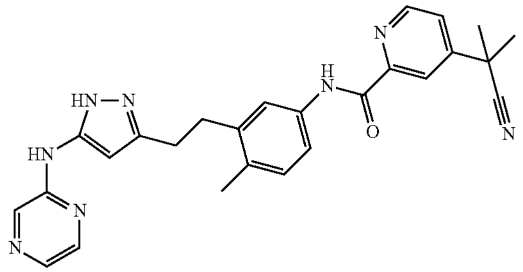 [SMILES: Cc1ccc(NC(=O)c2cc(C(C)(C)C#N)ccn2)cc1CCc1cc(Nc2cnccn2)[nH]n1] | $^1$H NMR (400 MHz, DMSO-$d_6$) δ ppm 12.05 (1 H, s), 10.52 (1 H, s), 9.53-9.65 (1 H, m), 8.79 (1 H, d), 8.48-8.61 (1 H, m), 8.27 (1 H, d), 8.08 (1 H, d), 7.81-7.89 (2 H, m), 7.77 (1 H, d), 7.68 (1 H, dd), 7.16 (1 H, d), 6.22-6.31 (1 H, m), 5.75-5.77 (1 H, m), 2.80-2.98 (4 H, m), 2.28 (3 H, s), 1.90-1.92 (1 H, m), 1.77 (6 H, s) ESI+ m/z 467 [M + H]+ | | |
| 4-(2-cyanopropan-2-yl)-N-(4-methyl-3-(2-(5-(pyrazin-2-ylamino)-1H-pyrazol-3-yl)ethyl)phenyl) picolinamide | | | |

Example 49

Preparation of Compound (I) (Compound 42) of Scheme 1

N-(4-fluoro-3-(2-(3-((6-(1-(2-hydroxyethyl)-1H-pyrazol-4-yl)-2-methylpyrimidin-4-yl) amino)-1H-pyrazol-5-yl)ethyl)phenyl)-3-(trifluoromethyl)benzamide

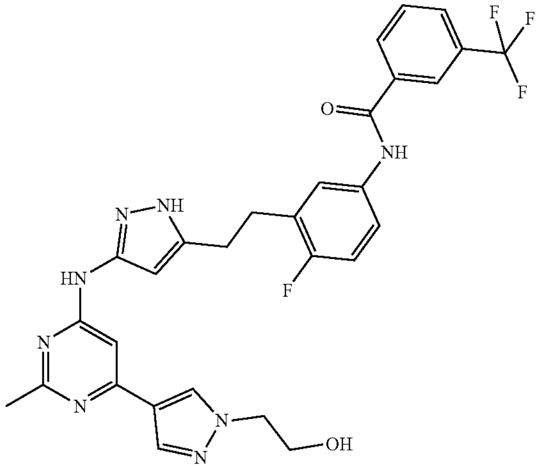 [SMILES: Cc1nc(Nc2cc(CCc3cc(NC(=O)c4cccc(C(F)(F)F)c4)ccc3F)[nH]n2)cc(-c2cnn(CCO)c2)n1]

To intermediate 115 (25 mg, 0.048 mmol) in THF (3.5 ml) was added intermediate 36 (28.7 mg, 0.120 mmol) followed by sodium carbonate (15.32 mg, 0.145 mmol) in water (1 ml). The resulting solution was degassed under vacuum and then placed under a nitrogen atmosphere. To the mixture was then added Bis(triphenylphosphine)palladium(II) dichloride (6.76 mg, 9.64 μmol) and the reaction was then heated to 80° C. for 2 hours then evaporated. To the remaining residue were added water (0.5 ml), acetic acid (0.5 ml) and DMSO (1.5 ml). Purification: reverse phase chromatography (25 g), eluting with $H_2O$—AcOH (0.1%) to $CH_3CN$—AcOH (0.1%) in gradient. Yield 20 mg of title compound (white solid).

$^1$H NMR (400 MHz, DMSO-$d_6$) δ ppm 12.11 (1H, br. s.), 10.47 (1H, s), 9.57 (1H, br. s.), 8.16-8.34 (3H, m), 7.97 (1H, d), 7.87 (1H, s), 7.73-7.82 (2H, m), 7.63-7.69 (1H, m), 7.19 (2H, t), 6.13 (1H, br. s.), 4.91 (1H, br. s.), 4.20 (2H, t), 3.76 (2H, t), 2.86-3.01 (4H, m), 2.42 (3H, s).

ESI+m/z 595 [M+H]

Example 50

General Procedures Used to Prepare Compounds of Inventions (Formula I) of Scheme 2

General Procedure 17:

To Intermediate 118 (0.1 mmol) in dry DMSO (3 ml) were added the corresponding amines (1 mmol). The resulting solution was then heated to 80° C. for 5-8 hours, cooled to RT, acetic acid was added (0.5 ml) and the resulting mixture was purified by reverse phase chromatography (25 g), eluting with $H_2O$—AcOH (0.1(%) to $CH_3CN$—AcOH (0.1%) in gradient.

With reference to the below table 9, following the procedures above indicated (3$^{rd}$ column of the table) by starting from intermediates above prepared (and indicated in the 2$^{nd}$ column of the below table) the compounds 43-46 have been prepared:

TABLE 9

| Compounds 43- 46 | | | |
|---|---|---|---|
| Compound | Intermediate | Procedure | Yield |
| 43 | 115 | 17 | 90 |
| 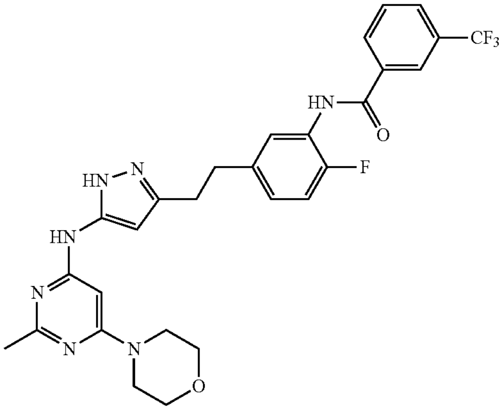 [SMILES: Cc1nc(Nc2cc(CCc3ccc(F)c(NC(=O)c4cccc(C(F)(F)F)c4)c3)n[nH]2)cc(N2CCOCC2)n1] | $^1$H NMR (400 MHz, DMSO-$d_6$) δ ppm 11.95 (1 H, br. s.), 10.36 (1 H, s), 9.12 (1 H, br. s.), 8.20-8.39 (2 H, m), 7.99 (1 H, d), 7.80 (1 H, t), 7.51 (1 H, dd), 7.08-7.30 (2 H, m), 6.61 (1 H, br. s.), 5.93 (1 H, br. s.), 3.59-3.74 (4 H, m), 3.37-3.50 (4 H, m), 2.79-3.00 (4 H, m), 2.27 (3 H, s)<br>ESI+ m/z 570 [M + H]+ | | |
| N-(2-fluoro-5-(2-(5-((2-methyl-6-morpholinopyrimidin-4-yl)amino)-1H-pyrazol-3-yl)ethyl)phenyl)-3-(trifluoromethyl)benzamide | | | |
| 44 | 115 | 17 | 77 |
| 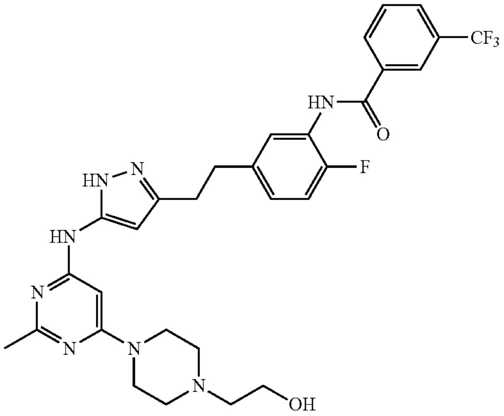 | $^1$H NMR (400 MHz, DMSO-$d_6$) δ ppm 11.82 (1 H, br. s.), 10.35 (1 H, s), 9.06 (1 H, s), 8.22-8.38 (2 H, m), 7.99 (1 H, d), 7.80 (1 H, t), 7.51 (1 H, dd), 7.08-7.29 (2 H, m), 6.55 (1 H, br. s.), 5.91 (1 H, s), 4.39 (1 H, br. s.), 3.53 (2 H, t), 3.42-3.49 (4 H, m), 2.81-2.97 (4 H, m), 2.37-2.49 (6 H, m), 2.25 (3 H, s)<br>ESI+ m/z 673 [M + H]+ | | |
| N-(2-fluoro-5-(2-(3-((6-(4-(2-hydroxyethyl)piperazin-1-yl)-2-methylpyrimidin-4-yl)amino)-1H-pyrazol-5-yl) ethyl)phenyl)-3-(trifluoromethyl)benzamide | | | |
| 45 | 115 | 17 | 79 |
| 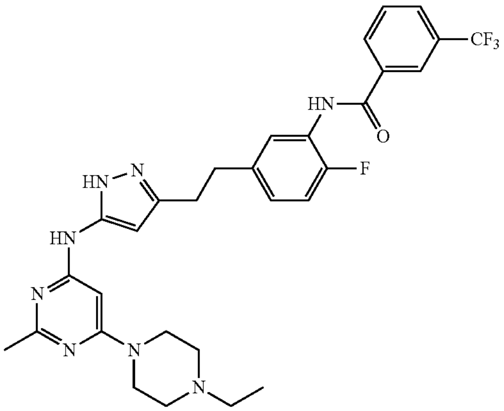 | $^1$H NMR (400 MHz, DMSO-$d_6$) δ ppm 11.86 (1 H, br. s.), 10.35 (1 H, s), 9.06 (1 H, s), 8.22-8.37 (2 H, m), 7.99 (1 H, d), 7.80 (1 H, t), 7.51 (1 H, dd), 7.07-7.29 (2 H, m), 6.55 (1 H, br. s.), 5.90 (1 H, s), 3.43-3.49 (4 H, m), 2.81-2.97 (4 H, m), 2.30-2.45 (6 H, m), 2.25 (3 H, s), 1.03 (3 H, d)<br>ESI+ m/z 657 [M + H]+ | | |

TABLE 9-continued

| Compounds 43- 46 | | | |
|---|---|---|---|
| Compound | Intermediate | Procedure | Yield |
| N-(5-(2-(3-((6-(4-ethylpiperazin-1-yl)-2-methylpyrimidin-4-yl)amino)-1H-pyrazol-5-yl)ethyl)-2-fluorophenyl)-3-(trifluoromethyl) benzamide | | | |
| 46 | 115 | 17 | 81 |
| 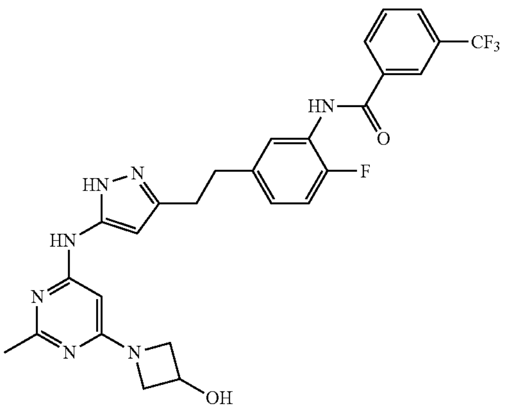 | $^1H$ NMR (400 MHz, DMSO-$d_6$) δ ppm 11.94 (1 H, br. s.), 10.35 (1 H, s), 9.05 (1 H, s), 8.22-8.38 (2 H, m), 7.99 (1 H, d), 7.80 (1 H, t), 7.51 (1 H, dd), 7.09-7.29 (2 H, m), 6.16 (1 H, br. s.), 5.88 (1 H, s), 5.65 (1 H, br. s.), 4.55 (1 H, t), 4.03-4.20 (2 H, m), 3.64 (2 H, dd), 2.79-2.97 (4 H, m), 2.23 (3 H,s) ESI+ m/z 616 [M + H]+ | | |
| N-(2-fluoro-5-(2-(3-((6-(3-hydroxyazetidin-1-yl)-2-methylpyrimidin-4-yl)amino)-1H-pyrazol-5-yl)ethyl) phenyl)-3-(trifluoromethyl)benzamide | | | |

Example 51

Preparation of Compound (I) (Compound 47) of Scheme 3

4-((dimethylamino)methyl)-N-(3-(2-(5-(4-morpholinobenzamido)-1H-pyrazol-3-yl)ethyl) phenyl) benzamide

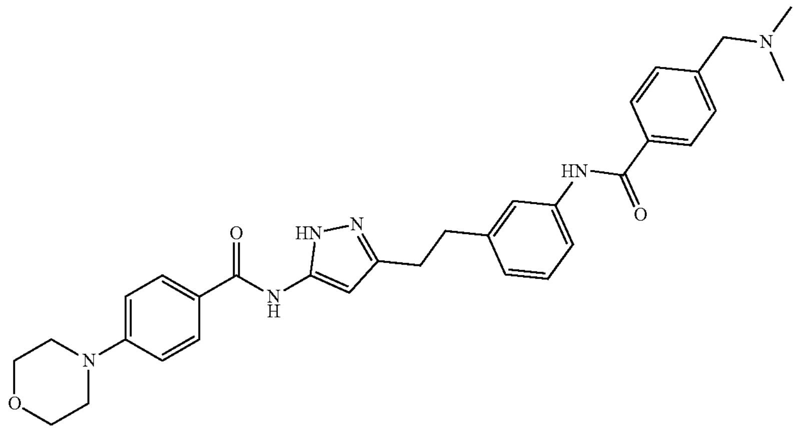 [SMILES: CN(C)Cc1ccc(C(=O)Nc2cccc(CCc3cc(NC(=O)c4ccc(N5CCOCC5)cc4)[nH]n3)c2)cc1]

To intermediate 121 (80 mg; 0.191 mmol) was added formic acid (1.798 ml, 47.7 mmol) and the resulting solution was heated to 100° C. for 1 hour. The formic acid was removed under vacuum and to the remaining residue was added DMSO (1 ml) and acetic acid (0.25 ml). Purification: reverse phase chromatography (15 g), eluting with $H_2O$—AcOH (0.1%) to $CH_3CN$—AcOH (0.1%) in gradient. Yield 28 mg (off white solid).

$^1H$ NMR (400 MHz, DMSO-$d_6$) δ ppm 12.14 (1H, br. s.), 10.37 (1H, br. s.), 10.16 (1H, s), 7.92 (4H, dd), 7.57-7.78 (2H, m), 7.44 (2H, d), 7.27 (1H, t), 6.88-7.06 (3H, m), 6.42 (1H, br. s.), 3.65-3.82 (4H, m), 3.47 (2H, s), 3.18-3.28 (4H, m), 2.81-3.01 (4H, m), 2.17 (6H, s).

ESI+m/z 553 [M+H]

Example 52

General Procedures Used to Prepare Compounds of Inventions (Formula I) of Scheme 4

General Procedure 18:

Carboxylic acids (1.5 mmol), HOBT (1.5 mmol), EDC (1.5 mmol) and DIPEA (3 mmol) were dissolved in DMF (10 ml) under nitrogen. After 15 minutes of activation, this mixture was added to a solution of intermediate (XVIII) (intermediate 123) in DMF (7.5 ml). The resulting mixture was stirred for 5-7 h at RT. The solvent was evaporated and the residue was purified by reverse phase chromatography (50 g), eluting with $H_2O$—AcOH (0.1%) to $CH_3CN$—AcOH (0.1%) in gradient.

With reference to the below table 10, following the procedures above indicated ($3^{rd}$ column of the table) by starting from intermediates above prepared (and indicated in the $2^{nd}$ column of the below table) the compounds 48-50 have been prepared:

TABLE 10

Compounds 48 - 50

| Compound | Intermediate | Procedure | Yield |
|---|---|---|---|
| 48 | 120 | 18 | 60 |
| 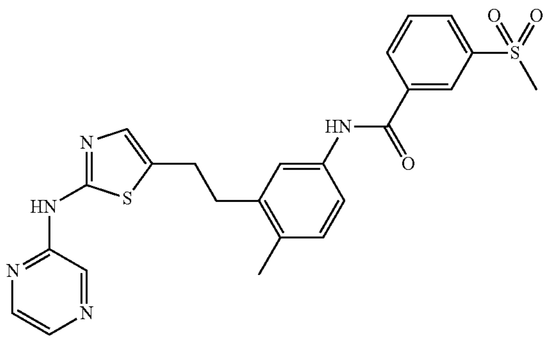 [SMILES: Cc1ccc(NC(=O)c2cccc(S(C)(=O)=O)c2)cc1CCc1cnc(Nc2cnccn2)s1] | $^1$H NMR (400 MHz, DMSO-$d_6$) δ ppm 11.49 (1 H, br. s.), 10.40 (1 H, s), 8.39-8.55 (2 H, m), 8.24-8.33 (2 H, m), 8.05-8.19 (2 H, m), 7.82 (1 H, t), 7.52-7.67 (2 H, m), 7.12-7.23 (2 H, m), 5.76 (1 H, s), 3.30 (3 H, s), 2.93 (4 H, s), 2.28 (3 H, s)<br>ESI+ m/z 494 [M + H]+ | | |
| N-(4-methyl-3-(2-(2-(pyrazin-2-ylamino)thiazol-5-yl)ethyl)phenyl)-3-(methylsulfonyl)benzamide | | | |
| 49 | 120 | 18 | 74 |
| 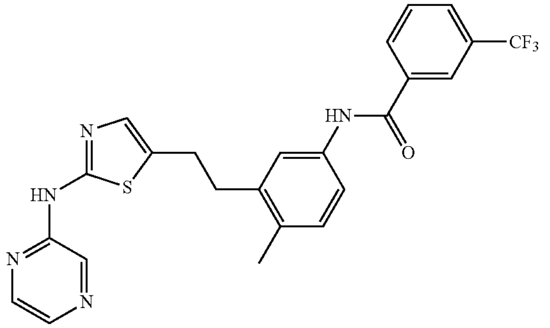 [SMILES: Cc1ccc(NC(=O)c2cccc(C(F)(F)F)c2)cc1CCc1cnc(Nc2cnccn2)s1] | $^1$H NMR (400 MHz, DMSO-$d_6$) δ ppm 11.43-11.56 (1 H, m), 10.35 (1 H, s), 8.43-8.49 (1 H, m), 8.23-8.34 (3 H, m), 8.06- 8.12 (1 H, m), 7.93-8.00 (1 H, m), 7.75-7.84 (1 H, m), 7.54-7.66 (2 H, m), 7.19 (2 H, s), 2.86-3.06 (4 H, m), 2.28 (3 H, s), 2.06-2.10 (1 H, m)<br>ESI+ m/z 484 [M + H]+ | | |
| N-(4-methyl-3-(2-(2-(pyrazin-2-ylamino)thiazol-5-yl)ethyl)phenyl)-3-(trifluoromethyl) benzamide | | | |
| 50 | 120 | 18 | 56 |
| 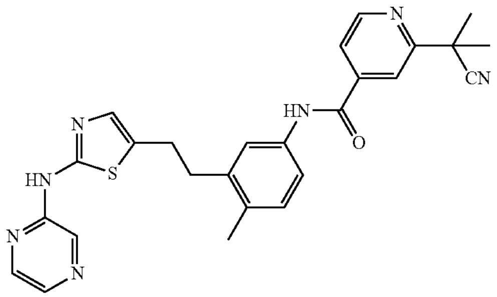 [SMILES: Cc1ccc(NC(=O)c2ccnc(C(C)(C)C#N)c2)cc1CCc1cnc(Nc2cnccn2)s1] | $^1$H NMR (400 MHz, DMSO-$d_6$) δ ppm 11.39-11.58 (1 H, m), 10.44 (1 H, s), 8.80 (1 H, d), 8.45 (1 H, s), 8.28 (1 H, dd), 8.09 (1 H, d), 8.01 (1 H, s), 7.82-7.89 (1 H, m), 7.52-7.65 (2 H, m), 7.13-7.26 (2 H, m), 2.85-3.07 (4 H, m), 2.28 (3 H, s), 1.78 (6 H, s)<br>ESI+ m/z 484 [M + H]+ | | |
| 2-(2-cyanopropan-2-yl)-N-(4-methyl-3-(2-(2-(pyrazin-2-ylamino)thiazol-5-yl)ethyl)phenyl) isonicotinamide | | | |

Pharmacological Evaluation of the Compounds of the Invention

Many compounds of Formula (I), according to the invention, have been studied in vitro in order to establish their potential Fyn kinase and VEGFR2 kinase inhibitory activity and their efficacy in some cellular model, as well as to establish the efficacy of the best compounds, resulting from the screening in vitro, in experiments of induced hyperalgesia and pain behaviour in rats.

The obtained results are summarized in the following Tables 11-16

Example 53: In Vitro Kinase Activity Assay

The Fyn kinase inhibitory activity of representative examples of compounds of Formula (1) was evaluated by Z'-LYTE™ Kinase Assay Platform (Invitrogen). Compounds were evaluated towards active Fyn (full length active, molecular weight 87.1 kDa; Invitrogen). The enzyme (1.2 ng/μl) was incubated in a 384 low-volume microplate with a synthetic peptide-substrate, ATP (50 μM) and different inhibitor concentrations, ranging from $10^{-9}$ M up to $10^{-5}$ M final concentration. Samples representing the 0% inhibition (or total enzymatic activity) were in the presence of compound diluent (1% DMSO final in Reaction Buffer 50 mMHepes, 10 mM MgCl2, 1 mM EGTA, 0.01% Brij-35, pH 7.5). The kinase reaction was carried out in a total volume of 10 μl, for 60 minutes at 25° C. The 0% Phosphorylation (i.e. no ATP) and 100% Phosphorylation Assay Controls, included in each plate, allowed to calculate the percent phosphorylation achieved in the specific reaction well. Results are expressed as percentage of inhibition and the $IC_{50}$ values were calculated by non-linear curve fitting using GraphPad™ Prism software (version 6 for Windows). The Fyn kinase inhibitory activity of representative compounds of Formula (I) is reported in the following table 11.

TABLE 11

FYN KINASE INHIBITION

| Compound | $IC_{50}$(nM) |
|---|---|
| 1 | 36 |
| 2 | 10 |
| 3 | 9 |
| 4 | 21 |
| 5 | 6 |
| 6 | 112 |
| 7 | 63 |
| 8 | 20 |
| 9 | 16 |
| 10 | 4 |
| 11 | 21 |
| 12 | 24 |
| 13 | 26 |
| 14 | 31 |
| 15 | 18 |
| 16 | 24 |
| 17 | 8 |
| 18 | 15 |
| 19 | 69 |
| 20 | 18 |
| 21 | 5 |
| 22 | 7 |
| 23 | 5 |
| 24 | 2 |
| 25 | 3 |
| 26 | 12 |
| 27 | 10 |
| 28 | 17 |
| 29 | 15 |
| 30 | 6 |
| 31 | 10 |
| 32 | 9 |
| 33 | 16 |
| 34 | 6 |
| 35 | 88 |
| 36 | 32 |
| 37 | 24 |
| 38 | 2 |
| 39 | 1 |
| 40 | 99 |
| 41 | 8 |
| 42 | 13 |
| 43 | 19 |
| 44 | 8 |
| 45 | 22 |
| 46 | 18 |
| 47 | 10 |
| 48 | 27 |
| 49 | 143 |
| 50 | 8 |

Results

As Table 11 shows, the compounds of Formula (I) are potent Fyn kinase inhibitors, with $IC_{50}$ values ranging in the low-medium nanomolar range. Only the compounds 6 and 49 resulted to be active in the high nanomolar range (>100 nM).

Example 54: In Vitro Kinase Activity Assay

The VEGFR2 kinase inhibitory activity of representative examples of compounds of Formula (I) assays was evaluated in Eurofins Cerep (France). The concentration range of the inhibitors under investigation was from $10^{-8}$ M up to $10^{-5}$ M final concentration. Some compounds were re-tested in a concentration-range starting from $10^{-9}$ M. The results are expressed as a percent of control activity (in the absence of test compound) and the $IC_{50}$ values were determined by non-linear regression analysis of the inhibition/concentration curves generated with mean replicate values.

The VEGFR2 kinase inhibitory activity of representative compounds of Formula (I) is reported in the following table 12.

TABLE 12

VEGFR2 KINASE INHIBITION

| Compound | $IC_{50}$(nM) |
|---|---|
| 1 | <10 |
| 2 | <10 |
| 3 | 7 |
| 4 | <10 |
| 5 | <10 |
| 6 | <10 |
| 7 | <10 |
| 8 | <10 |
| 9 | <10 |
| 10 | <10 |
| 11 | <10 |
| 12 | <10 |
| 13 | <10 |
| 14 | 10 |
| 15 | <10 |
| 16 | <10 |
| 17 | <10 |
| 18 | 16 |
| 19 | 110 |
| 26 | <10 |
| 27 | 12 |
| 28 | <10 |
| 29 | <10 |
| 30 | <10 |

TABLE 12-continued

| VEGFR2 KINASE INHIBITION | |
|---|---|
| Compound | $IC_{50}$(nM) |
| 31 | 18 |
| 32 | <10 |
| 33 | <10 |
| 34 | <10 |
| 35 | <10 |
| 36 | <10 |
| 37 | 35 |
| 39 | 11 |
| 40 | <10 |
| 41 | <10 |
| 42 | 20 |
| 43 | 10 |
| 44 | <10 |
| 45 | <10 |
| 46 | <10 |
| 47 | 10 |
| 48 | 10 |

Results

As Table 12 shows, the compounds of Formula (I) are good VEGFR2 kinase inhibitors ($IC_{50}$<10 nM), being compounds 1-17, 20-30, 32-36, 38, 40-48 potent VEGFR2 kinase inhibitors.

Example 55: In Vitro Kinase Activity Assay in the Presence of High ATP Concentration The inhibition of Fyn and VEGFR2 kinase activity was evaluated in the presence of a fixed ATP concentration (0.5 mM), near to the millimolar range present in cells. The assay was performed by The ADP-Glo™ Kinase Assay (Promega), monitoring ADP produced in the kinase reaction. Kinase reaction was performed in 10 μl, according to supplier indication, in a white 384-well plate.

Inhibitor solutions in DMSO/Kinase buffer and the kinase (Fyn 2.5 ng/μl and VEGFR2 0.5 ng/μl final concentration in assay) were pre-incubate 15 minutes at room temperature. The range of inhibitor concentrations was from $10^{-10}$ M up to $10^{-5}$ M (final concentration in assay). To start the reaction, a substrate/ATP mix (0.5 mM final concentration, corresponding to 10× ATP KM value) was added to each sample. After 60 minutes incubation at room temperature, ADP-Glo™ Reagent and Kinase Detection Reagent, added and incubated in sequence according to supplier indication, allowed to stop and develop the kinase reaction. The percentage of inhibition, calculated towards the enzymatic activity in the absence of test compound, and the corresponding inhibition curves were analyzed by non-linear curve fitting (GraphPad software, version 7 for Windows), allowing to calculate the $IC_{50}$ value.

Results

Compound 3 inhibited Fyn and VEGFR2 in the presence of high ATP concentrations, in a concentration dependent way with $IC_{50}$ values of 6.8 nM and 58 nM, respectively.

Example 56: Kinase Selectivity

The kinase selectivity of some representative compounds of Formula (I) were analyzed in a standard panel of 46 human kinases, identifying 10 kinases as the more frequently affected.

Therefore Compound 3 was examined for kinase selectivity focusing on these 10 kinases. The assays were performed in Eurofins Cerep (France). The concentration range of the compound under investigation was from $10^{-9}$ M up to $10^{-5}$ M final concentration. The results are summarized in Table 13.

TABLE 13

| KINASE SELECTIVITY $IC_{50}$ (nM) | | | | | | | |
|---|---|---|---|---|---|---|---|
| Lyn-A | Yes | Src | Jak3 | FGFR2 | CDK2 | AurA | AMPKa |
| 59 | 17 | 370 | 1760 | 3000 | IN | IN | IN |

IN: inactive at maximal concentration tested (10 μM)

Results

As already shown in Table 12, Compound 3 exhibits a nanomolar potency in inhibiting Fyn and VEGFR2 kinase activity. Besides the effect for other kinases of the Src family (Src, Yes and Lyn-A), but lower than that showed for Fyn and VEGFR2, Compound 3 is inactive (>1000 nM) for the remaining kinases investigated.

Example 57: Cellular Model for Testing Kinase Inhibition-Gene Reporter (GR) Assay To determine if the compounds of the invention were active also in a cellular model, a gene reporter assay was established in a cell line (JB6 Cl 41-5a (P+)) know to activate Fyn kinase via an inflammatory stimuli (TNFα). GR assay measures the activation of the nuclear transcription factor NF-kB, situated down-stream the Fyn activation pathway. Products active in this analysis has to penetrate in the cell and inhibit the activation pathway of NF-kB.

The murine epithelial cell line JB6 Cl 41-5a (P+) (ATCC® Cat. #CRL-2010) was stably transfected with the pGL4.32[luc2P/NFkB-RE/Hygro] vector (Promega). Clonal selection was achieved by limiting with 80 μg/ml Hygromycin B. The clones were tested for their response to TNFα stimulus.

JB6(P+) NFkB-RE-luc2P transfected cells were used for the analysis of NF-kB activity modulation, after TNFα stimulation, by Fyn-inhibitors.

Cells were pre-treated with the different compounds for 1 h and then stimulated with 2 ng/ml TNFα for 4 h. Each tested condition was analyzed in quadruplicate.

The luciferase analysis was performed with ONE-Glo™+ ToxLuciferase Reporter and Cell Viability Assay kit (Promega). The results obtained at non toxic concentrations, evaluated by CellTiter-Fluor™ Cell Viability Assay, are summarized in the following Table 14.

TABLE 14

| Gene reporter (GR) inhibition | |
|---|---|
| Compound | $IC_{50}$(nM) or % effect at max concentration |
| 1 | 5081 |
| 2 | 312 |
| 3 | 236 |
| 4 | 2233 |
| 5 | 3255 |
| 6 | 2672 |
| 7 | 1158 |
| 8 | 233 |
| 9 | 10 μM 47% |
| 10 | 1999 |
| 11 | 785 |
| 12 | 4514 |

TABLE 14-continued

| Gene reporter (GR) inhibition | |
|---|---|
| Compound | $IC_{50}$(nM) or % effect at max concentration |
| 13 | 308 |
| 14 | 487 |
| 15 | 100 |
| 16 | 321 |
| 17 | 352 |
| 18 | 974 |
| 19 | 883 |
| 20 | 3 μM 45% |
| 21 | 3 μM 37% |
| 22 | 1140 |
| 23 | 1435 |
| 24 | 2327 |
| 25 | 1421 |
| 26 | 3 μM 50% |
| 30 | ne |
| 31 | 10 μM 47% |
| 32 | 3 μM 29% |
| 33 | 363 |
| 34 | 958 |
| 35 | 1306 |
| 36 | 494 |
| 37 | 2261 |
| 38 | 10 μM 25% |
| 39 | 1065 |
| 40 | 515 |
| 41 | 327 |
| 42 | 10 μM 56% |
| 43 | 2439 |
| 47 | ne |
| 48 | 275 |
| 49 | 422 |
| 50 | 3 μM 86% |

ne: no effect

Results

As Table 14 shows, some compounds of the invention demonstrated to be able to penetrate into the cell, and to inhibit at sub-micromolar/micromolar concentration the Fyn kinase activation induced by TNF-α stimulation. In particular compounds 3, 8 and 15 showed an $IC_{50}$ value <250 nM

Example 58: Intracellular Target Engagement Towards Fyn Enzyme in HEK293 Transfected Cells The intracellular target engagement (TE) of Fyn kinase was demonstrated through nanoBRET technology (Promega), allowing to measure the compound binding at selected target proteins within intact cells and to determinate the apparent affinity of test compounds by competitive displacement of the NanoBRET™ tracer, reversibly bound to a NanoLuc® luciferase fusion protein in cells.

The NanoBRET™ TE intracellular kinase assay K-4 (Promega, #N2520) was used to determine the intracellular target engagement of Fyn kinase in HEK293 cells (ATCC®, Cat. CRL-1573) transiently transfected with Fyn-NanoLuc® fusion vector (Promega, #NV1411), therefore expressing the Fyn-NanoLuc© fusion protein. The tracer was used at the final concentration of 0.33 μM, and the treatment of cells with Compounds was performed for 2 hours. Luminescence values were measured at 450 nm and 610 nm (GloMax® Discover, Promega) and raw BRET ratio values for each sample were determined. Compounds that specifically engage the intracellular target protein-NanoLuc® fusion will result in a decrease in BRET signal and in lower BRET ratio values Results Compound 3 showed an $IC_{50}$ binding value of 1.5 μM towards the Fyn-NanoLuc® fusion protein transiently expressed in HEK293 cells.

Example 59: Inhibition of Fynb-Induced Tau(Y18)-Phosphorylation (Cell-Based Assay)

HEK293 cells (Human Embryonic Kidney 293) were seeded at $6\times10^5$ in poly-D-lysine 12 w microplates and grown adherent in medium DMEM/10% FBS at 37° C. with 5% $CO_2$. After 24 h, cells were transfected in order to over-express either constitutively active form of human FynB and Tau protein (isoform 0N4R), through an optimized Lipofectamine®3000 Transfection protocol (Life Technologies™). A non-transfected sample (negative control) was included in every experiment. Twenty-four hours from transfection, treatments of cells were performed by adding fresh medium containing diluent (DMSO 0.1% final concentration) or test compounds. The incubation was carried out for 6 or 24 hours at 37° C. with 5% $CO_2$. At the end of the incubation, the medium was removed and cellular lysates, obtained by adding M-PER lysis/Protease/Phosphatase inhibitors cocktail, were transferred into Eppendorf tubes, sonicated and stored at −80° C. Protein content was measured by Bradford method. Lysates were analyzed either by customized ELISA assays for Tau phosphorylation (Tyrosine 18 residue—Fyn mediated) and Tau-Total amount determination.

Results

After 6 hours of treatment, Compound 3 inhibited FynB-induced Tau(Y18)-phosphorylation in a concentration dependent way ($IC_{50}$ of 0.131 μM). The compound maintained its inhibitory activity after 24 hours of treatment, with a mean percentage of inhibition of 95% at 1p M. Moderate not significant effect on Tau-protein total amount was observed.

Example 60: Inhibition of VEGF-Induced VEGFR (Y1175)-Phosphorylation (Cell-Based Assay)

HUVEC-C cells (Human Umbilical Vein Endothelial Cells from ATCC) were plated at $6\times10^4$ cells/well in 24 w microplates and grown adherent in medium F12K+0.1 mg/ml Heparin+0.05 mg/ml ECGS+10% FBS at 37° C. with 5% $CO_2$. After 24 h, medium was removed and starvation was induced overnight in medium F12K+0.1 mg/ml Heparin+0.5% FBS (medium starvation). At the end of incubation, treatment of cells was performed by medium replacement and by adding fresh medium starvation containing or not diluent (DMSO 0.1% final concentration), or test compound (range $10^{-8}$ M-$10^{-5}$ M). After 1 hour, VEGF stimuli (50 ng/ml final concentration) was added to each sample, with the exception of "basal-no stimulus" sample; plate was then incubated for 5 min at 37° C. with 5% $CO_2$. At the end of the incubation, the medium was removed and cellular lysates, obtained by adding M-PER lysis/Protease/Phosphatase inhibitors cocktail. Then, lysates were transferred into Eppendorf tubes, sonicated and stored at −80° C.

Lysates were analyzed by Western blot for VEGFR phosphorylation (Tyrosine 1175) and total receptor amount determination. Densitometric analysis of sample lanes were performed by ImageQuant TL software (GE Healthcare Life Sciences). Each sample value was normalized by respective actin; resulting data were used to calculate inhibitory effect of compounds with respect to stimuli control (absence of inhibitor). RESULTS Compound 3 showed a complete inhibitory activity on VEGFR-phosphorylation at Y1175 residue starting from the concentration of 0.01 μM.

Example 61: Gene Expression Analysis in Rat Articular Chondrocytes Under Inflammatory Conditions (IL-1β Stimulation)

Rat primary articular chondrocytes were obtained from the inferior and superior limb of Sprague Dawley rats following the protocol used by Berenbaum and colleagues (Berenbaum F, Thomas G, Poiraudeau S, Bereziat G, Corvol M T, Masliah J. Insulin-like growth factors counteract the effect of interleukin 1 beta on type II phospholipase A2 expression and arachidonic acid release by rabbit articular chondrocytes. FEBS Lett 1994; 340:51-55). All studies involving animals were carried out in accordance with the Guide for the Care and Use of Laboratory Animals as adopted and promulgated by the US National Institutes of Health.

Purified chondrocytes were resuspended in DMEM glutaMAX 10% and plated in a 96X well plate for toxicity analysis and in a 6X well plate for gene expression analysis.

For toxicity analysis cells were then treated with the different compounds for 24 and 48 h. At the end of the incubation time, the medium was removed and was substituted with a mixture 10:1 of DMEM glutaMAX 10%—MTT (2 mg/ml) for 1 h at 37° C. in the cell incubator. After this incubation, the precipitated salt was dissolved with 100 μl of DMSO and the plate was read at 540 nm. The toxicity analysis were performed to decide the maximal non toxic concentration of each compound used in the gene expression assay.

For gene expression analysis, 10 days after plating, the medium was changed and substituted with DMEM GlutaMAX I 0.4% to synchronize the cells. The cells were then co-treated in DMEM GlutaMAX I 0.4% with different concentrations of the test compounds and IL-10 at a final concentration of 2 ng/ml for 6 h and 24 h. The test compound concentrations used have been chosen on the basis of the toxicity data.

At the end of the incubation, the supernatant was discarded, the cell were washed with cold PBS1X and scraped with 200 μl of RNA lysis buffer 1X (Nucleic Acid Purification Lysis Solution, Applied Biosystems).

Total RNA was purified using ABI Prism™ 6100 Nucleic Acid PrepStation (Applied Biosystems) following manufacturer's instructions.

Total RNA was retrotranscribed using the High-Capacity cDNA Archive Kit (Applied Biosystems-Thermo Fisher Scientific) following manufacturer's instructions.

The specific probes and primers for RealTime PCR were from Applied Biosystems (Thermo Fisher Scientific) as Assays-on-Demand™, while the probe and primers for the endogenous control 18S was a PDAR (Pre-Developed TaqMan® Assay Reagents—Applied Biosystems-Thermo Fisher Scientific).

The gene expression of the most relevant pro-inflammatory markers and matrix degradative enzyme upregulated in osteoarthrosis was analysed.

The assays were designed to amplify target cDNA without amplifying genomic DNA.

Gene expression analysis for IL-1β, IL-6 and ADAMTS-5 were performed at 6 h incubation, while the gene expression analysis for MMP3, MMP13 and COX2 were performed at 24 h incubation.

For each compound the maximal concentration tested was dependent on the toxicity results obtained on primary rat chondrocytes.

The data analysis, with the normalisation on the amplified values for the 18S was done following the specific instruction of Applied Biosystems for the relative quantification of gene expression.

TABLE 15

Gene expression analysis of the most relevant pro-inflammatory and matrix degradative markers induced after stimulation with IL-1β ($IC_{50}$ μM or percentage of inhibitory effect at the highest non toxic concentration)

| Compound | IL-1β | IL-6 | COX2 | ADAMTS-5 | MMP3 | MMP13 | First toxic concentration at 24 h |
|---|---|---|---|---|---|---|---|
| 1 | 2.1 | 1.6 | 3.1 | 10 μM 38% | ne | 10 μM 38% | >10 μM |
| 2 | 10 μM 100% | 10 μM 100% | 10 μM 100% | 10 μM 94% | 10 μM 92% | 10 μM 99% | >10 μM |
| 3 | 0.002 | 0.018 | 0.187 | 0.034 | 0.323 | 0.477 | 10 μM |
| 4 | 1.7 | 10 μM 93% | 1.4 μM | 3 μM | 10 μM 55% | 10 μM 84% | >10 μM |
| 5 | 10 μM 84% | 10 μM 89% | 10 μM 43% | 5.5 | ne | 10 μM 32% | >10 μM |
| 6 | 1 μM 50% | 0.64 | ne | 1 μM 28% | ne | ne | 3 μM |
| 7 | 0.1 | 0.2 | 1 μM 41% | 1 μM 81% | ne | 1 μM 38% | 3 μM |
| 8 | 0.3 | 1 μM 99% | 1 μM 63% | ne | ne | ne | 3 μM |
| 11 | 10 μM 100% | 10 μM 100% | 10 μM 100% | 10 μM 100% | 2.2 | 2.4 | >10 μM |
| 12 | 3.9 | 2.6 | 10 μM 63% | 10 μM 57% | ne | 10 μM 34% | >10 μM |
| 13 | 1 μM 96% | 1 μM 100% | 1 μM 96% | 1 μM 88% | 0.3 | 1 μM 94% | 3 μM |
| 14 | 3 μM 99% | 3 μM 100% | 3 μM 100% | 3 μM 99% | 3 μM 95% | 3 μM 99% | 10 μM |
| 15 | 3 μM 98% | 3 μM 100% | 3 μM 97% | 3 μM 96% | 3 μM 90% | 3 μM 99% | 10 μM |
| 17 | 10 μM 99% | 10 μM 100% | 10 μM 96% | 10 μM 62% | 10 μM 92% | 10 μM 100% | >10 μM |
| 19 | 0.1 | 3 μM 99% | 0.4 | 0.1 | 0.6 | 0.5 | 10 μM |
| 33 | 3 μM 93% | 3 μM 100% | 3 μM 89% | 3 μM 90% | 3 μM 81% | 3 μM 94% | 10 μM |
| 34 | 3 μM 99% | 3 μM 100% | 3 μM 76% | 3 μM 97% | 3 μM 58% | 3 μM 82% | 10 μM |
| 35 | 10 μM 74% | 10 μM 90% | 10 μM 90% | 3 | 10 μM 44% | 10 μM 88% | >10 μM |
| 37 | 1.6 | 10 μM 97% | 10 μM 97% | 4 | 10 μM 59% | 10 μM 95% | >10 μM |
| 39 | 3 μM 100% | 3 μM 100% | 3 μM 99% | 0.5 | 1.2 μM | 3 μM 90% | 10 μM |
| 40 | 10 μM 100% | 10 μM 100% | 10 μM 100% | 2.3 | 0.5 | 10 μM 100% | >10 μM |
| 48 | 0.6 | 0.2 | ne | 1 μM 70% | ne | ne | 3 μM |
| 49 | 1 μM 91% | 1 μM 100% | 1 μM 93% | 0.2 μM | 0.5 | 0.24 | 3 μM |

ne: no effect

Results

As Table 15 shows, most compounds of the invention, demonstrated to inhibit the gene expression of the pro-inflammatory (IL-1β, IL-6, COX2) and degradative (ADAMTS-5, MMP3, MMP13) markers studied, in particular compound 3 inhibit at sub-micromolar concentration the gene expression induced by IL-1β stimulation.

Example 62: Inhibition of Cartilage Degradation in a Bovine in Vitro Model

Nasal septum cartilage was collected from an eight months-old male bovine in a local slaughterhouse.

Tissue was sprayed with ethanol 70% and immediately put in sterile PBS with Antibiotic-Antimycotic stabilized solution (PBS-AASS). It was cut in order to obtain small punches (diameter 2 mm, 1 mm-thick). washed with sterile PBS-AASS, the slices were transferred in a 96X well plate (one piece per well) in DMEM 10%+AASS. 48 h later the cartilage was stimulated in white DMEM+0.1% BSA+AASS with IL-1α 10 ng/m in the absence or presence of the studied compounds.

The compounds concentration used in this analysis was chosen depending on the toxicity results obtained in rat primary chondrocytes at 48 h of incubation.

After 48 h stimulation, the culture medium was collected and stored at −80° C. The cartilage punches were digested with papain at 65° C. for 2 h in phosphate buffer (0.05M pH 6.5 with 2 mM N-acetil-L-cisteine and 2 mM EDTA).

The glycosaminoglycan (GAG) determination was done by a colorimetric assay with 1,9 dimethyl methylene blue (DMB).

Digested cartilage samples were diluted in PBS-BSA 1%. To 100 μl of diluted samples or standard we added 100 μl DMB 2X. After 5-20 min incubation the samples were read at 590 nm (Titertek Multiscan Plus).

The cartilage degradation induced by IL-1α was expressed as:

GAG (medium)/total GAG (medium+cartilage)×100

TABLE 16

Inhibitory effect on bovine cartilage degradation induced by IL-1α

| Compound | $IC_{50}$(nM) or % inhibitory effect at max concentration) | First toxic concentration at 48 h in rat primary chondrocytes | Compound | $IC_{50}$(nM) or % inhibitory effect at max concentration | First toxic concentration at 48 h in rat primary chondrocytes |
|---|---|---|---|---|---|
| 1 | 3 μM 88% | 10 μM | 19 | 3 μM 83% | 10 μM |
| 2 | 0.8 μM | >10 μM | 33 | 3 μM 91% | 10 μM |
| 3 | 1 μM 100% | 3 μM | 34 | 1 μM 96% | 3 μM |
| 4 | ne | 3 μM | 35 | 1.5 μM | >10 μM |
| 5 | 3 μM 79% | 10 μM | 37 | 10 μM 99% | >10 μM |
| 6 | ne | 3 μM | 40 | 3 μM 49% | 10 μM |
| 11 | 10 μM 89% | >10 μM | 48 | ne | 3 μM |
| 12 | ne | 10 μM | 49 | 1 μM 35% | 3 μM |
| 13 | 1 μM 97% | 3 μM | | | |
| 14 | 3 μM 97% | 10 μM | | | |
| 15 | 1 μM 96% | 3 μM | | | |
| 17 | 10 μM 100% | >10 μM | | | |

ne: no effect

Results

As Table 16 shows, most compounds of the invention, demonstrated to inhibit the cartilage degradation induced by IL-1α, in particular compounds 3, 13, 15 and 34 were able to inhibit completely (inhibitory effect between 95-100%) the GAG release.

Example 63: Description of Pharmacological Activity in "Vivo" of the Compounds of the Invention Compound of formula (I) has been proved to be potent analgesics in a model of inflammatory, acute pain. The efficacy of the compound of Formula (I) has been tested for its analgesic efficacy in the following in vivo animal model of inflammatory pain.

Complete Freund Adjuvant (CFA)-Induced Inflammatory Pain in Rats.

CFA, injected intradermally in the hind paw of rats, induces a long lasting inflammation and hyperalgesia. The compound 3 was injected in the right hind paw of male Wistar rats in the same bolus containing 50 μg of *Mycobacterium tuberculosis* in 100 μL of liquid paraffin (CFA).

Eighteen hours after the challenge, mechanical pain threshold was determined using a Randall-Selitto apparatus, and the values obtained were compared with those obtained before CFA injection. The measure of hyperalgesia was repeated 24, 42 and 48 hours after CFA injection.

Results

Figure 2:
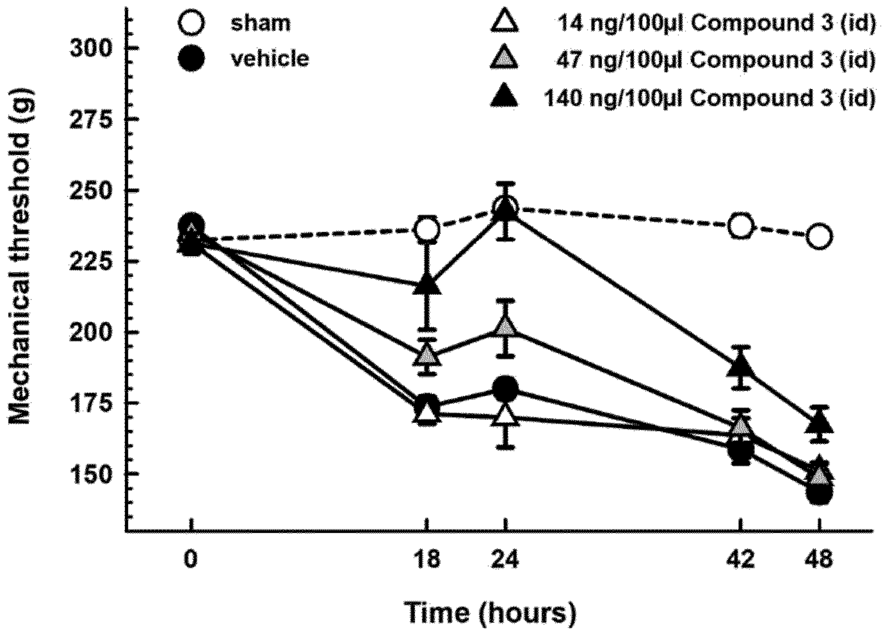
FIG. 2: Dose-response curve of local analgesic efficacy of different doses of compound 3 in the rat CFA assay. The activity is reported as the mechanical threshold (weight borne by the CFA inflamed paw).

FIGS. 1 and 2 show the results obtained in CFA-induced inflammatory pain model, for the Compound 3. The results demonstrated that Compound 3 given by local (intra-dermal, i.d.) administration, was a very potent inhibitor of CFA induced hyperalgesia. The compound, injected at the maximal concentration of 3 μM (i.e. 140 ng/paw) completely reverted the pain behavior in CFA inflamed animals and did not modify the normal nociception in naïve animals that did not received the challenge with CFA.

Example 64: Pharmacokinetics

Compound 3 was characterized by a sub-optimal pharmacokinetic profile when given by systemic routes. From the oral route, its absolute bioavailability is about 12% in mice and 6% in rats. However, the lack of important metabolism in rats and the relevant local analgesic effects already described, render compound 3 particularly suitable for the local treatment of OA, by intra-articular injection.

Compound 3 administered to rats in suspension (Phosphate Buffer 150 mM pH7, 0.5% HPMC, 0.1% Tween 80) into the knee joint, demonstrated a depot-like long-lasting permanence in the synovial fluid and articular tissues (cartilage and synovial fat) for at least 14 days.

The invention claimed is:

1. A N-phenylcarbamoyl compound of Formula (I)

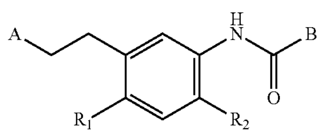

(I)

or a salt thereof wherein

A is selected from the group consisting of

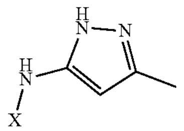

and

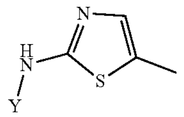

where

X is an optionally substituted group selected from the group consisting of a 5- or 6-membered heteroaryl ring, 2,3-dihydro-1H-pyrrolo[3,4-c]pyridinyl, (5- or 6-membered heteroaryl)CO—, (phenyl)CO— and 5- or 6-membered saturated heterocyclic ring;

Y is an optionally substituted 5- or 6-membered heteroaryl ring;

B is an optionally substituted group selected from the group consisting of a phenyl, a 5- or 6-membered heteroaryl ring, 5- or 6-membered saturated heterocyclic ring, azaspiro($C_7$-$C_{10}$)alkyl and saturated ($C_3$-$C_6$) cycloalkyl-NH—;

$R_1$ and $R_2$ are optionally and not simultaneously present and independently selected from ($C_1$-$C_3$)alkyl and halogen.

2. The N-phenylcarbamoyl compound according to claim 1, wherein the heteroaryl ring of X is pyrazine, pyridine or pyrimidine.

3. The N-phenylcarbamoyl compound according to claim 2, wherein the heteroaryl ring is substituted with one or more substituent selected from the group consisting of ($C_1$-$C_3$) alkyl, (morpholino)methyl, (dimethylmorpholino)methyl, pyrrolidine-1-yl-methyl, 4-ethylpiperazin-1-yl, 4-(2-hydroxyethyl)piperazin-1-yl, 3-hydroxyazetidin-1-yl, 3-(dimethylamino)pyrrolidin-1-yl, (2-hydroxyethyl)-1H-pyrazol-4-yl, morpholine-1-yl and cyano.

4. The N-phenylcarbamoyl compound according to claim 1, wherein X is 2,3-dihydro-1H-pyrrolo[3,4-c]pyridinyl substituted with one or more substituent selected from the group consisting of ($C_1$-$C_3$)alkyl, hydroxy($C_1$-$C_3$)alkyl, ($C_1$-$C_3$) alkyl)CO—.

5. The N-phenylcarbamoyl compound according to claim 1, wherein X is (pyridine)CO— or (pyrimidine)CO—.

6. The N-phenylcarbamoyl compound according to claim 1, wherein X is an optionally substituted (phenyl)CO—.

7. The N-phenylcarbamoyl compound according to claim 1, wherein Y is an unsubstituted pyrazine.

8. The N-phenylcarbamoyl compound according to claim 1, wherein $R_1$ is hydrogen, methyl, fluoro or chloro and, independently from $R_1$, $R_2$ is hydrogen or fluoro.

9. The N-phenylcarbamoyl compound according to claim 1, wherein B is an optionally substituted phenyl.

10. The N-phenylcarbamoyl compound according to claim 9, wherein phenyl is substituted with one or more substituent selected from the group consisting of $CH_3SO_2$—, —$CH_2N(CH_3)_2$, $CH_3$, $CF_3$, $CHF_2$, fluoro, —$SO_2N(CH_3)_2$, (N-ethyl)aminocyclopropyl.

11. The N-phenylcarbamoyl compound according to claim 1, wherein B is an optionally substituted 5- or 6-membered heteroaryl ring selected from pyridine and oxazole.

12. The N-phenylcarbamoyl compound according to claim 1, wherein B is a 5- or 6-membered heteroaryl ring substituted with one or more substituents selected form the group consisting of hydroxy($C_1$-$C_3$)alkyl, $CF_3$, ($C_1$-$C_4$)alkyl, cyano($C_1$-$C_3$)alkyl and ($C_3$-$C_6$)cycloalkyl-$SO_2$—.

13. The N-phenylcarbamoyl compound according to claim 11, wherein B is pyridine or oxazole substituted with one or more substituents selected from the group consisting of 2-cyanopropyl-2-yl, 2-hydroxypropyl-2-yl, $CH_3$, $CF_3$, fluoro, isobutyl or cyclopropylsulphonyl.

14. The N-phenylcarbamoyl compound according to claim 1, wherein B is azaspiro($C_7$-$C_{10}$)alkyl selected from azaspiro[3,4]octane and azaspiro[4,5]decane.

15. The N-phenylcarbamoyl compound according to claim 1, wherein B is pyrrolidine.

16. The N-phenylcarbamoyl compound according to claim 1, wherein B is an optionally substituted saturated ($C_3$-$C_6$)cycloalkyl-NH—.

17. The N-phenylcarbamoyl compound according to claim 1, wherein A is

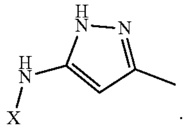

.

18. The N-phenylcarbamoyl compound according to claim 17, wherein X is an optionally substituted 5- or 6-membered heteroaryl ring.

19. The N-phenylcarbamoyl compound according to claim 17, wherein B is an optionally substituted phenyl.

20. The N-phenylcarbamoyl compound according to claim 1 selected from the group consisting of:

1) N-(4-methyl-3-(2-(5-(pyrazin-2-ylamino)-1H-pyrazol-3-yl)ethyl)phenyl)-3-(methyl sulfonyl)benzamide, 2) 2-(2-cyanopropan-2-yl)-N-(4-methyl-3-(2-(5-(pyrazin-2-ylamino)-1H-pyrazol-3-yl) ethyl)phenyl) isonicotinamide, 3) N-(4-methyl-3-(2-(5-(pyrazin-2-ylamino)-1H-pyrazol-3-yl)ethyl)phenyl)-3-(trifluoro methyl)benzamide, 4) 4-(1-(ethylamino)cyclopropyl)-N-(4-methyl-3-(2-(5-(pyrazin-2-ylamino)-1H-pyrazol-3-yl)ethyl)phenyl) benzamide, 5) 2-(2-hydroxypropan-2-yl)-N-(4-methyl-3-(2-(5-(pyrazin-2-ylamino)-1H-pyrazol-3-yl) ethyl)phenyl) isonicotinamide, 6) 2-methyl-N-(4-methyl-3-(2-(5-(pyrazin-2-ylamino)-1H-pyrazol-3-yl)ethyl)phenyl)-5-(trifluoromethyl)oxazole-4-carboxamide, 7) 2-fluoro-N-(4-methyl-3-(2-(5-(pyrazin-2-ylamino)-1H-pyrazol-3-yl)ethyl)phenyl)-5-(trifluoromethyl) benzamide, 8) 4-(cyclopropylsulfonyl)-N-(4-methyl-3-(2-(5-(pyrazin-2-ylamino)-1H-pyrazol-3-yl) ethyl)phenyl)picolinamide, 9) N-(3-(2-fluoro-5-(6-isobutylnicotinamido)phenethyl)-1H-pyrazol-5-yl)pyrimidine-2-carboxamide
10) N-(4-fluoro-3-(2-(5-((2-(2-hydroxyethyl)-2,3-dihydro-1H-pyrrolo[3,4-c]pyridin-6-yl) amino)-1H-pyrazol-3-yl)ethyl)phenyl)-3-(trifluoromethyl)benzamide
11) 2-(2-cyanopropan-2-yl)-N-(4-fluoro-3-(2-(5-(pyrazin-2-ylamino)-1H-pyrazol-3-yl) ethyl)phenyl) isonicotinamide,
12) N-(4-fluoro-3-(2-(5-(pyrazin-2-ylamino)-1H-pyrazol-3-yl)ethyl)phenyl)-3-(methyl sulfonyl)benzamide,
13) N-(4-fluoro-3-(2-(5-(pyrazin-2-ylamino)-1H-pyrazol-3-yl)ethyl)phenyl)-3-(trifluoro methyl)benzamide,
14) N-(3-(2-(5-((3,5-dimethylpyrazin-2-yl)amino)-1H-pyrazol-3-yl)ethyl)-4-fluoro phenyl)-3-(trifluoromethyl) benzamide,
15) N-(4-fluoro-3-(2-(5-((3-methylpyrazin-2-yl)amino)-1H-pyrazol-3-yl)ethyl)phenyl)-3-(trifluoromethyl) benzamide,
16) N-(4-chloro-3-(2-(5-(pyrazin-2-ylamino)-1H-pyrazol-3-yl)ethyl)phenyl)-3-(trifluoro methyl)benzamide,
17) N-(3-(2-(5-((2-ethyl-2,3-dihydro-1H-pyrrolo[3,4-c] pyridin-6-yl)amino)-1H-pyrazol-3-yl)ethyl)-4-methylphenyl)-3-(trifluoromethyl)benzamide,
18) N-(5-(2-methyl-5-(3-(trifluoromethyl)benzamido) phenethyl)-1H-pyrazol-3-yl) picolinamide,
19) N-(3-(2-(3-(4-fluorobenzamido)-1H-pyrazol-5-yl) ethyl)-4-methylphenyl)-3-(trifluoro methyl)benzamide,
20) N-(4-methyl-3-(2-(5-((3-methylpyrazin-2-yl)amino)-1H-pyrazol-3-yl)ethyl)phenyl)-6-azaspiro[3.4]octane-6-carboxamide,
21) 3,3-diethyl-N-(4-methyl-3-(2-(5-((3-methylpyrazin-2-yl)amino)-1H-pyrazol-3-yl) ethyl)phenyl) pyrrolidine-1-carboxamide
22) 3,3-diethyl-N-(4-methyl-3-(2-(5-(pyrazin-2-ylamino)-1H-pyrazol-3-yl)ethyl) phenyl) pyrrolidine-1-carboxamide
23) N-(3-(5-(3-(4,4-dimethylcyclohexyl)ureido)-2-methylphenethyl)-1H-pyrazol-5-yl)-4-((1-isopropylazetidin-3-yl)oxy)benzamide,
24) N-(3-(5-(3-cyclopentylureido)-2-methylphenethyl)-1H-pyrazol-5-yl)-4-(4-methyl piperazin-1-yl)benzamide,
25) N-(3-(5-(3-(4,4-dimethylcyclohexyl)ureido)-2-methylphenethyl)-1H-pyrazol-5-yl)-4-(1-methylpiperidin-4-yl)benzamide,
26) N-(4-fluoro-3-(2-(3-((2-methyl-6-(morpholinomethyl)pyrimidin-4-yl)amino)-1H-pyrazol-5-yl)ethyl) phenyl)-3-(trifluoromethyl)benzamide,
27) N-(3-(2-(3-((6-(((2S,6R)-2,6-dimethylmorpholino) methyl)-2-methylpyrimidin-4-yl) amino)-1H-pyrazol-5-yl)ethyl)-4-fluorophenyl)-3-(trifluoromethyl)benzamide,
28) N-(4-fluoro-3-(2-(3-((2-methyl-6-(pyrrolidin-1-ylmethyl)pyrimidin-4-yl)amino)-1H-pyrazol-5-yl)ethyl) phenyl)-3-(trifluoromethyl)benzamide,
29) N-(3-(2-(3-((6-(4-ethylpiperazin-1-yl)-2-methylpyrimidin-4-yl)amino)-1H-pyrazol-5-yl)ethyl)-4-fluorophenyl)-3-(trifluoromethyl)benzamide,
30) N-(4-fluoro-3-(2-(3-((6-(4-(2-hydroxyethyl)piperazin-1-yl)-2-methylpyrimidin-4-yl) amino)-1H-pyrazol-5-yl)ethyl)phenyl)-3-(trifluoromethyl)benzamide,
31) N-(4-fluoro-3-(2-(3-((6-(3-hydroxyazetidin-1-yl)-2-methylpyrimidin-4-yl)amino)-1H-pyrazol-5-yl)ethyl) phenyl)-3-(trifluoromethyl)benzamide,
32) (S)-N-(3-(2-(3-((6-(3-(dimethylamino)pyrrolidin-1-yl)-2-methylpyrimidin-4-yl)amino)-1H-pyrazol-5-yl) ethyl)-4-fluorophenyl)-3-(trifluoromethyl)benzamide,
33) 3-(difluoromethyl)-N-(4-methyl-3-(2-(5-(pyrazin-2-ylamino)-1H-pyrazol-3-yl) ethyl) phenyl)benzamide,
34) N-(3-(2-(5-((2-acetyl-2,3-dihydro-1H-pyrrolo[3,4-c] pyridin-6-yl)amino)-1H-pyrazol-3-yl)ethyl)-4-methylphenyl)-3-(trifluoromethyl)benzamide,
35) 3-(isopropylsulfonyl)-N-(4-methyl-3-(2-(5-((3-methylpyridin-2-yl)amino)-1H-pyrazol-3-yl)ethyl) phenyl) benzamide,
36) 2-(2-cyanopropan-2-yl)-N-(4-methyl-3-(2-(5-((3-methylpyridin-2-yl)amino)-1H-pyrazol-3-yl)ethyl) phenyl)isonicotinamide,
37) N-(3-(2-(5-((6-cyano-2-methylpyrimidin-4-yl) amino)-1H-pyrazol-3-yl)ethyl)-4-methylphenyl)-3-(N, N-dimethylsulfamoyl)benzamide,
38) N-(3-(2-(5-((6-cyano-2-methylpyrimidin-4-yl) amino)-1H-pyrazol-3-yl)ethyl)-4-methylphenyl)-8-azaspiro [4.5]decane-8-carboxamide,
39) N-(3-(2-(5-((6-cyano-2-methylpyrimidin-4-yl) amino)-1H-pyrazol-3-yl)ethyl)-4-fluorophenyl)-4-((dimethylamino) methyl)-3-(trifluoromethyl)benzamide,
40) N-(4-fluoro-3-(2-(5-((2-methylpyrimidin-5-yl) amino)-1H-pyrazol-3-yl)ethyl)phenyl)-3-(trifluoromethyl) benzamide,
41) 4-(2-cyanopropan-2-yl)-N-(4-methyl-3-(2-(5-(pyrazin-2-ylamino)-1H-pyrazol-3-yl)ethyl)phenyl)picolinamide,
42) N-(4-fluoro-3-(2-(3-((6-(1-(2-hydroxyethyl)-1H-pyrazol-4-yl)-2-methylpyrimidin-4-yl)amino)-1H-pyrazol-5-yl)ethyl)phenyl)-3-(trifluoromethyl)benzamide,
43) N-(2-fluoro-5-(2-(5-((2-methyl-6-morpholinopyrimidin-4-yl)amino)-1H-pyrazol-3-yl)ethyl)phenyl)-3-(trifluoromethyl)benzamide,
44) N-(2-fluoro-5-(2-(3-((6-(4-(2-hydroxyethyl)piperazin-1-yl)-2-methylpyrimidin-4-yl) amino)-1H-pyrazol-5-yl) ethyl)phenyl)-3-(trifluoromethyl)benzamide,
45) N-(5-(2-(3-((6-(4-ethylpiperazin-1-yl)-2-methylpyrimidin-4-yl)amino)-1H-pyrazol-5-yl)ethyl)-2-fluorophenyl)-3-(trifluoromethyl)benzamide,
46) N-(2-fluoro-5-(2-(3-((6-(3-hydroxyazetidin-1-yl)-2-methylpyrimidin-4-yl)amino)-1H-pyrazol-5-yl)ethyl) phenyl)-3-(trifluoromethyl)benzamide,
47) 4-((dimethylamino)methyl)-N-(3-(2-(5-(4-morpholinobenzamido)-1H-pyrazol-3-yl) ethyl) phenyl) benzamide,
48) N-(4-methyl-3-(2-(2-(pyrazin-2-ylamino)thiazol-5-yl)ethyl)phenyl)-3-(methyl sulfonyl)benzamide,
49) N-(4-methyl-3-(2-(2-(pyrazin-2-ylamino)thiazol-5-yl)ethyl)phenyl)-3-(trifluoro methyl)benzamide, and
50) 2-(2-cyanopropan-2-yl)-N-(4-methyl-3-(2-(2-(pyrazin-2-ylamino)thiazol-5-yl)ethyl) phenyl)isonicotinamide.

21. The N-phenylcarbamoyl compound of claim 20 selected from the group consisting of:
3) N-(4-methyl-3-(2-(5-(pyrazin-2-ylamino)-1H-pyrazol-3-yl)ethyl)phenyl)-3-(trifluoro methyl)benzamide,
6) 2-methyl-N-(4-methyl-3-(2-(5-(pyrazin-2-ylamino)-1H-pyrazol-3-yl)ethyl)phenyl)-5-(trifluoromethyl)oxazole-4-carboxamide,
8) 4-(cyclopropylsulfonyl)-N-(4-methyl-3-(2-(5-(pyrazin-2-ylamino)-1H-pyrazol-3-yl) ethyl)phenyl)picolinamide,
13) N-(4-fluoro-3-(2-(5-(pyrazin-2-ylamino)-1H-pyrazol-3-yl)ethyl)phenyl)-3-(trifluoro methyl)benzamide, 15) N-(4-fluoro-3-(2-(5-((3-methylpyrazin-2-yl)amino)-1H-pyrazol-3-yl)ethyl)phenyl)-3-(trifluoromethyl) benzamide, 34) N-(3-(2-(5-((2-acetyl-2,3-dihydro-1H-pyrrolo[3,4-c] pyridin-6-yl)amino)-1H-pyrazol-3-yl)ethyl)-4-methylphenyl)-3-(trifluoromethyl)benzamide, and 49) N-(4-methyl-3-(2-(2-(pyrazin-2-ylamino)thiazol-5-yl)ethyl)phenyl)-3-(trifluoro methyl)benzamide.

22. The N-phenylcarbamoyl compound of claim 21 that is compound 3) N-(4-methyl-3-(2-(5-(pyrazin-2-ylamino)-1H-pyrazol-3-yl)ethyl)phenyl)-3-(trifluoromethyl) benzamide.

23. A pharmaceutical composition comprising the N-phenylcarbamoyl compound of Formula (I) or a pharmaceutically acceptable salt thereof according to claim 1 and pharmaceutically acceptable excipients.

24. A method for the inhibition of at least one of tyrosine kinase selected from Fyn and VEGFR2 in the treatment of diseases and disorders involved with one or both kinases comprising the step of administering to a subject in need thereof a N-phenylcarbamoyl compound of Formula (I) or a pharmaceutically acceptable salt thereof according to claim 1.

25. The method according to claim 24, wherein the inhibition of both kinases Fyn and VEGFR2 is in the treatment of diseases/disorders/pathologies involved with both kinases.

26. The method according to claim 25, wherein the treatment of a disorder/disease/pathology is selected from the group consisting osteoarthritis; eye diseases, skin disorders a acute or chronic pain, lung diseases, and cancer.

27. The N-phenylcarbamoyl compound according to claim 6, wherein X is an optionally substituted (phenyl)CO substituted with one or more substituent selected from the group consisting of halogen, (1-isopropylazetidin-3-yl)oxy, 4-methylpiperazin-1-yl, and 1-methylpiperidin-4-yl.

28. The N-phenylcarbamoyl compound according to claim 9, wherein B is a substituted phenyl substituted with one or more substituent selected from the group consisting of (C1-C3)alkyl, R'SO2-, R'R"N(C1-C3)alkyl, R'NH(C1-C3)alkyl, trifluoromethyl, difluoromethyl, halogen, R'R"NSO2-, (C3-C6)cycloalkyl, (C3-C6)cycloalkyl-NH—, NR'(C3-C6)cycloalkyl- where R' and R" are, independently each other, (C1-C3)alkyl.

29. The N-phenylcarbamoyl compound according to claim 15, wherein B is pyrrolidine substituted with one or more $(C_1-C_3)$alkyl.

30. The N-phenylcarbamoyl compound according to claim 16, wherein B is 4,4-(dimethylciclohexyl)-NH—, cyclopentyl-NH—.

31. The N-phenylcarbamoyl compound according to claim 18, wherein X is an optionally substituted pyrazine.

32. The N-phenylcarbamoyl compound according to claim 19, wherein B is phenyl substituted with $CF_3$.

* * * * *